US011129844B2

(12) United States Patent
Freier et al.

(10) Patent No.: US 11,129,844 B2
(45) Date of Patent: Sep. 28, 2021

(54) COMPOSITIONS AND METHODS FOR MODULATING MECP2 EXPRESSION

(71) Applicants: Ionis Pharmaceuticals, Inc., Carlsbad, CA (US); Baylor College of Medicine, Houston, TX (US)

(72) Inventors: Susan M. Freier, San Diego, CA (US); Huda Y. Zoghbi, Houston, TX (US); Ezequiel Sztainberg, Houston, TX (US)

(73) Assignees: Ionis Pharmaceuticals, Inc., Carlsbad, CA (US); Baylor College of Medicine, Houston, TX (US)

( * ) Notice: Subject to any disclaimer, the term of this patent is extended or adjusted under 35 U.S.C. 154(b) by 11 days.

(21) Appl. No.: 16/535,888

(22) Filed: Aug. 8, 2019

(65) Prior Publication Data

US 2020/0078389 A1  Mar. 12, 2020

Related U.S. Application Data

(63) Continuation-in-part of application No. 15/554,407, filed as application No. PCT/US2016/020610 on Mar. 3, 2016, now abandoned, application No. 16/535,888, which is a continuation-in-part of application No. 15/554,409, filed as application No. PCT/US2016/020771 on Mar. 3, 2016, now abandoned.

(60) Provisional application No. 62/127,693, filed on Mar. 3, 2015, provisional application No. 62/127,682, filed on Mar. 3, 2015.

(51) Int. Cl.
*C12N 15/113* (2010.01)
*A61P 25/22* (2006.01)
*A61K 31/712* (2006.01)

(52) U.S. Cl.
CPC ............ *A61K 31/712* (2013.01); *A61P 25/22* (2018.01); *C12N 15/113* (2013.01); *C12N 2310/11* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |

(Continued)

FOREIGN PATENT DOCUMENTS

| | | |
|---|---|---|
| WO | WO 2016/141145 | 9/1916 |
| WO | WO 2016/141236 | 9/1916 |

(Continued)

OTHER PUBLICATIONS

Bennett et al., "Antisense oligonucleotides as a tool for gene functionalization and target validation" Biochim Biophys Acta (1999) 1489(1): 19-30.

Branch et al., "A good antisense molecule is hard to find," TIBS (1998) 23:45-50.

Chahrour et al., "MeCP2, a key contributor to neurological disease, activates and represses transcription" Science (2008) 320: 1224-1229.

(Continued)

*Primary Examiner* — Sean McGarry
(74) *Attorney, Agent, or Firm* — McNeill Baur PLLC

(57) ABSTRACT

Disclosed herein are compounds and methods for decreasing MECP2 mRNA and protein expression. Such compounds and methods are useful to treat, prevent, or ameliorate MECP2 associated disorders and syndromes. Such MECP2 associated disorders include MECP2 duplication syndrome.

29 Claims, 1 Drawing Sheet

Specification includes a Sequence Listing.

(56) References Cited

U.S. PATENT DOCUMENTS

| | | |
|---|---|---|
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2007/0134697 A1 | 6/2007 | Khvorova et al. |
| 2008/0039618 A1 | 2/2008 | Allerson et al. |
| 2009/0082297 A1 | 3/2009 | Lioy et al. |
| 2010/0190837 A1 | 7/2010 | Migawa et al. |
| 2010/0197762 A1 | 8/2010 | Swayze et al. |
| 2010/0247543 A1 | 9/2010 | Maes et al. |
| 2012/0171279 A1 | 7/2012 | Karelson et al. |
| 2013/0116301 A1 | 5/2013 | Freier et al. |
| 2013/0130378 A1 | 5/2013 | Manoharan et al. |
| 2013/0296400 A1 | 11/2013 | Monia et al. |
| 2014/0107330 A1 | 4/2014 | Freier et al. |
| 2015/0018540 A1 | 1/2015 | Prakash et al. |
| 2015/0099791 A1 | 4/2015 | Krieg et al. |
| 2015/0152410 A1 | 6/2015 | Krieg et al. |

(56) References Cited

U.S. PATENT DOCUMENTS

| | | | |
|---|---|---|---|
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |
| 2018/0036335 | A1 | 2/2018 | Freier |
| 2018/0044673 | A1 | 2/2018 | Zoghbi et al. |

FOREIGN PATENT DOCUMENTS

| | | |
|---|---|---|
| WO | WO 2016/149455 | 9/1916 |
| WO | WO 2005/116204 | 12/2005 |
| WO | WO 2009/027349 | 3/2009 |
| WO | WO 2010/105096 | 9/2010 |
| WO | WO 2011/071232 | 6/2011 |
| WO | WO 2013/173608 | 11/2013 |
| WO | WO 2014/052393 | 4/2014 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Collins et al., "Mild overexpression of MeCP2 causes a progressive neurological disorder in mice" Hum Mol Genet (2004) 13: 2679-2689.
Crooke et al., "Basic Principles of Antisense Therapeutics" Antisense Research and Application (1998) Chapter 1:1-50.
Crooke, St., et al., "Antisense Drug Technology" Second Edition, CRC Press (2008) Chapters 1-28.
Dastidar et al. "Isoform-specific toxicity of Mecp2 in postmitotic neurons: Suppression of neurotoxicity of neurotoxcity by FoxG1" J Neurosci. (2012) 32(8): 2846-2855.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Gautschi et al., "Activity of a novel bc1-2/bc1-xLbispecific antisense oligonucleotide against tumors of diverse histologic origins" J. Natl. Cancer Inst. (2001) 93:463-471.
Gould et al., "The Open Field Test" Mood and Anxiety Related Phenotypes in Mice (2009) 1-20.
Jin et al., "RNAi-induced down-regulation of Mecp2 expression in the rat brain" Int J Dev Neurosci (2008) 26(5): 457-465.
Jones et al., "Methylated DNA and MeCP2 recruit histone deacetylase to repress transcription" Nat Genet. (1998) 19: 187-191.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Na et al., "GABAA receptor antagonism ameliorates behavioral and synaptic impairments associated with MeCP2 overexpression" Neuropsychopharmacology (2014) 39(8): 1946-1954.
Nan et al., "Transcriptional repression by the methyl-CpG-binding protein MeCP2 involves a histone deacetylase complex" Nature (1998) 393: 386-389.
New England Biolabs 1998/99 Catalog (cover page and pp. 121 and 284).
Pandey et al. "Identification and Characterization of Modified Antisense Oligonucleotides Targeting DMPK in Mice and Nonhuman Primates for the Treatment of Myotonic Dysrophy Type 1" J Pharmacol Exp Ther. (2015) 355(2):329-340.
Ramocki et al., "The MECP2 duplication syndrome" Am J Med Genet A (2010) 152A: 1079-10188.
Reynolds et al., "Rational siRNA design for RNA interference" Nature Biotechnology (2004) 22(3):326-330.
Samaco et al., "Crh and Oprm1 mediate anxiety-related behavior and social approach in a mouse model of MECP2 duplication syndrome" Nat Genet (2012) 44(2): 206-211.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sztainbergt et al. "Reversal of phenotypes in MECP2 duplication mice using genetic rescue or antisense oligonucleotides" Nature (2015) 528:123-126.
Walf et al., "The use of the elevated plus maze as an assay of anxiety-related behavior in rodents" Nat Protoc (2007) 2(2): 322-328.
Weaving et al., "Rett syndrome: clinical review and genetic update" J Med Genet (2005) 42: 1-7.
Woolf et al., "Specificity of antisense oligonucleotides in vivo" PNAS (1992) 89: 7305-7309.
Extended European Search Report for 16759471.2 dated Jul. 26, 2018.
International Search Report for PCT/US16/20610 dated May 20, 2016.
International Search Report for PCT/US2016/020771 dated Aug. 5, 2016.
Partial Search Report for 16759530.5 dated Oct. 1, 2018.
Shao et al., "Antisense oligonucleotide therapy for MECP2 duplication syndrome" Poster Presentation for BCM Graduate Symposium 2017 (Oct. 24, 2017), 1 page.
Shao et al., "Antisense oligonucleotide therapy for MECP2 duplication syndrome" Poster Presentation for Society for Neuroscience Annual Meeting 2019 (Oct. 19, 2019) Chicago, IL, 1 page.
Shao et al., "Antisense oligonucleotide therapy in a humanized mouse model of MECP2 duplication syndrome" Sci Transl Med (2021) 13: 1-11.
Shao et al., "Optimizing antisense oligonucleotide therapy in a mouse model that exclusively express two copies of human MECP2" Abstract for Systems Biology: Global Regulation of Gene Expression (CSHL) 2017 (Feb. 26, 2017), 1 page.
Shao et al., "Testing the safety boundaries of MECP2 expression using Antisense Oligonucleotides" Poster Presentation for RNA & Oligocnucleotide Therapeutics (CSHL) 2017 (Mar. 29, 2017), 1 page.
Sztainberg et al., "Optimization of an antisense oligonucleotide therapy in a novel MECP2 duplication mouse model" Poster Presentation for Society for Neuroscience Annual Meeting 2016 (Nov. 12, 2016) San Diego, CA, 1 page.

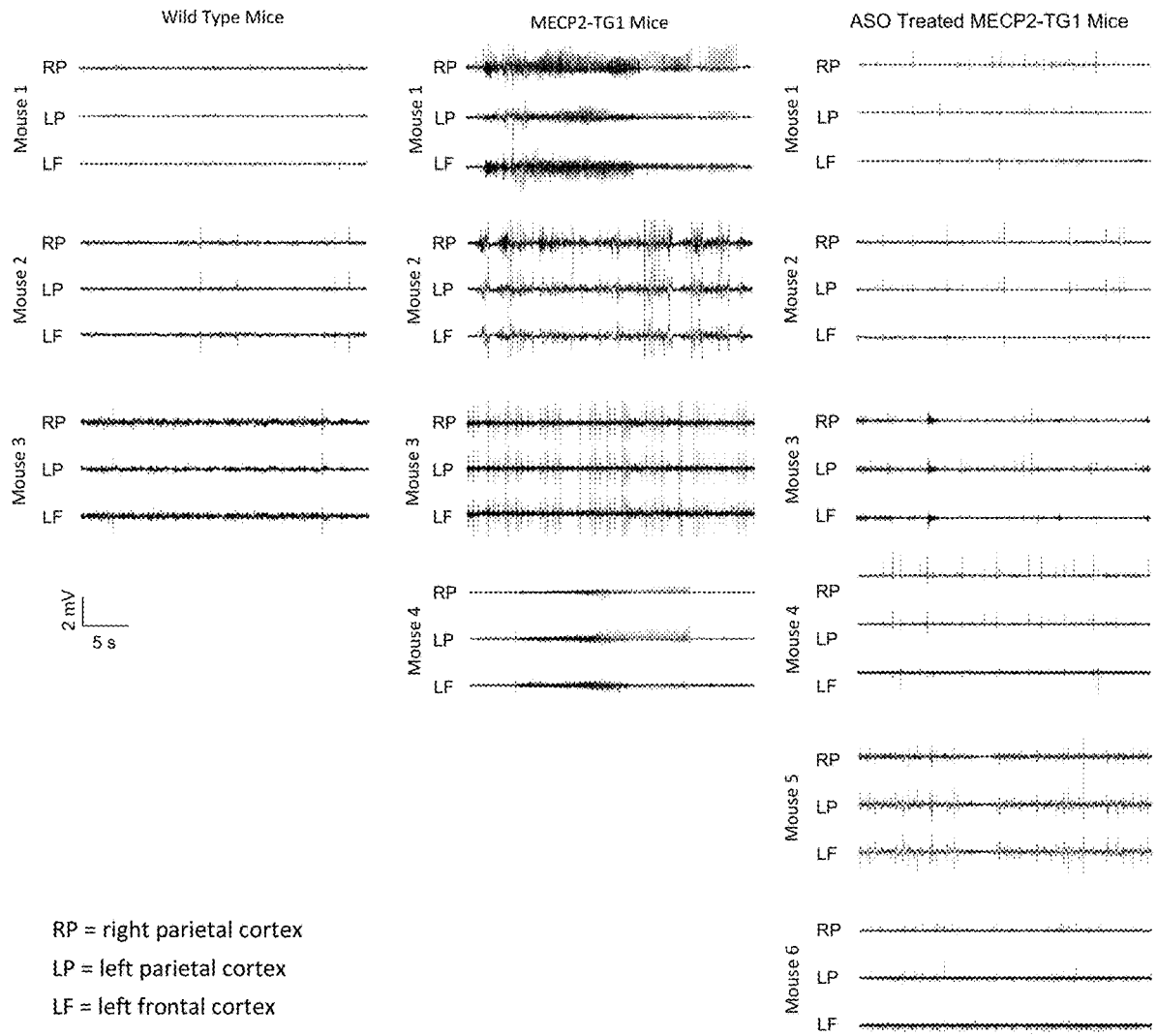

SEQUENCE LISTING

```
<160> NUMBER OF SEQ ID NOS: 328

<210> SEQ ID NO 1
<211> LENGTH: 80001
<212> TYPE: DNA
<213> ORGANISM: Homo sapiens

<400> SEQUENCE: 1
gctaccatca actctttctc ctagactgtt ccagggcctt gcaactagcc ttgtgctgta     60
gttttgtttc atcacgtcca gttctccact ctacacctgc aacatagatc agacagctcc    120
tggctcaaaa tcctctgagg gcttctcatc ttagaataaa ctctcggttc tggccgggtg    180
cggtggctta cgcctgtagt cccagcactt gggagtccg aggcgggcgg atcacttgaa    240
ctcaggagtt tgagaccagc ctgggcaaca tggtgaactc ccatctctat caaaaataca    300
aaaacttagc caggcgtggt ggttcgcatc tgtggtccca gctacttagg acgctgagga    360
gggaggatcg cttgagctca gggtggacgt tgcagtgagc caagattgcg ccactgcact    420
gcagcctggg tgacagaatg agaccccatc cccacccccc ccaaaaaaga atgaactccc    480
agttctcata gtggcccag ctgcctttcc aatcacattc cctaccactc tccagcaaca    540
ctgacttcct cgttagtccc caacatgcca ggcatagtct ctcctcatgt cctttgaact    600
tgcctggaat gttctttccc cagatattca tatgagggag taaatgagg gtgaaaacca    660 gcagatatct aaatagcacc cccttcactt agtttatctt tctcaaagcc cttatcacta    720
tgtgaaatga tatattatac ttatttgtat gctagtatga atcttcccgg caagaatgtt    780
agtttgctgt ctgttcagta ccgtgcatcc agagcctgga agagtgcctg gcacatagca    840
ggtagtcaat aaatgaatgg gggcaagcag ccaaatcaga atcaggtttt cttgctaagc    900
atagaactaa cagaaggatc attgaatgga ttggataatg actggcatca gggtaaggtc    960
cccttaacaa acactcctgt cctgaacacc tggttagcta acagttttct catactctta   1020
ttttcccaaa acacaattgc tggatctcag ctccaaatca actcttctag gaaagtgaaa   1080
```

```
aattgctgga tctcagctcc caaatcatat cttccaggca gagctaacat tgccccttat   1140
tcacacctcc accaaaccat ctgatccaac agtgacaggt gtcacgaggc cttggcatgc   1200
actctcttcc cccgccagag ttctgcgaaa gccagggttg cgatttgttg tcagtttatt   1260
ccccgcctct atgagagtgt gagcactggg caggctcgga tgaaataatg cattgagtag   1320
gcctctgaaa ccaaggcccc tcagctgggg caacgtcagg ctccagggtg ggcaactttg   1380
ctgcttctgc cgaagatagt gatattgaga aaatgtgggt gcaatgaaac gcttattgca   1440
gcgcactcgg tgcatctgtg acagagggt caatcgcccc tcagagcagc gcaaacaggc   1500
gtcccaagcc taggccttca cttgcccag catccgcaag ggtccattaa tccttaacat   1560
tcaaattccg cccactaaac cagtccctcc gcgcccaagc cgcctctttt ccccaaacga   1620
cggccgaaag cagccaatca acagctgag gggtccgccc ccttttccct ggccgaaatg   1680
gacaggaaat ctcgccaatt gacggcatcg ccgctgagac ctccccctc cccgtcctc    1740
cccgtcccag cccggccatc acagccaatg acgggcgggc tcgcagcggc gccgagggcg   1800
gggcgcgggc gcgcaggtgc agcagcgcgc gggccggcca agaggcgggg gcgcgacgtc   1860
ggccgtgcgg ggtcccggcg tcggcggcgc gcgcgctccc tcctctcgga gagagggctg   1920
tggtaaaagc cgtccggaaa atggccgccg ccgccgccgc cgcgccgagc ggaggaggag   1980
gaggaggcga ggaggagaga ctgtgagtgg gaccgccgtg gccgcgggcg gggacccttg   2040
ccggggggcg ggggtcaggg gcgggacgtg gcgcgggagg ggcccgcggg gtcggacgac   2100
acggctggcg gatggcgtcc ctcctctcta ccctccccct cccgccgccg ccggtggcga   2160
ctctcccctc ggcccgtcac ccgtgctcgc gggtgaccgt cctcggcgcg gcctccctgg   2220
agccgccttc gcctgacgcc cctcttcctc ccgccctcga cgcgcatccc ggccccggc    2280
cccgcgggcg ccctgtcgc cggggttcgc ctgtcggggc tgcgcgcgct cctgcccttc    2340
tcggggcttt gggccgcggc gccgtcgcgc gcccgcggcc ccggcctctc cctggatcgc   2400
gctctccccc tccctccctc gcgcgccccc tctcccgtta tcggcccccc caccggcgc    2460
gcgtgcgcac ttcgcctccc gtcgggagag tgcgccacaa gggctcctga gctctcaccc   2520
ccatctctgg gctttgcctc cccctccttc tcgcccattc catgaatttc tgccccccgc   2580
tacccccccg cgagcgagta ggtccaccgg ctccttccc catctagcag gaacaagtag   2640
gtggggatta ttatccacaa aagggactag acattgtgtt ctgggtccca caactcatca   2700
taaagaggtg gttatagttc ccatcaggag ccgtgggtag gggactgtgc gtccagcagc   2760
acccgaggct cttcggcgcc agaggctcta aggtgcgagc gtgtccccag ggtgctcaga   2820
ggttctttgg agtgctgtgg cctcggaatg tgagcaccct cccatcctac cctccccttc   2880
gccggcgatc ttccagttac ataagtggag tgggacatag taggtaacgg gctctcatcg   2940
ccctggagcg ctcgggatca ccggtaccag atggggcaag ttcatcgcga cgctgtggct   3000
cctgttaatt gtgcctgaaa ggttatcctc tgttcagttt ggtcatgacc gaatcaccca   3060
aactgaaact cagatgactt ttatatggca gtggcaatgt ttctgtggtt ttgcactaaa   3120
gacttaaggt cattatgaag agtgtaaaag gattgctgtc gcaggggaga ccgtttatga   3180
cattgctaag tatggacccc gagggggaaa aagctcattc tggaattgct ctgtggcggt   3240
tgcttctgtt gcgagtgtgt tcgggtgtgg gttggtcaca gcagaaatgg gctccaccac   3300
aaaattgata ttcctgactc atggtcaggc agatgtgtgc ttctggttat ttttccagga   3360
acaggaatgg gctctgccga gccttttcaca cgttgtgtct ctgctgtgcg ggatcagtac   3420
cccagactgt gagataacag gatcgaattc agggggttggt tggtgatcca ggaaccatac   3480
```

```
ctacttggat gtgatactga gtggcctaga cgttgtagga ctctcataag ttttagacat    3540
tttgttatac tgtaaaaatg aagcatatac ggcctcagta gtaacattgc actaataggt    3600
aattattact ctagagaatt tgggttcca tggctggaat gttcatcagt atctcagcaa    3660
tttcagttaa taaccagatt aagctgacct cttgagtctt ttgaaatctg ctgggtccct    3720
ataataagac agggtctgga ttttttaatc ttttgggaat ttccaccaag gatttaggga    3780
aataggcttt tatgggcttt tcaggatttc tatttcaaat cccaatgagg aagtctagga    3840
aacacttgct tttatttct tgcctgaata tgtcagaacc ttaaatcacc caatcaatct     3900
agaagtacta cagttgatta aagtaagtca ccacaggtca cccattcgtg gcaggtcagc    3960
taggtggctg atcactggaa tacagtcata tccccaggca tacacacgag cctcacttga    4020
cgatcccaaa gtttgtacat ctgagcttga gacgtgacaa gttgaggtct ctgctttgtt    4080
cttcatagtt ggcagtttgt ctcctcgggt gcccctccgg ttagctgttt atcatacgtc    4140 tagcccatc aacagtgcag gcagcttcca gagtatagtt ttctctgcaa agtgcctggt     4200
ggaggggtac ctccttttcc attgtcctaa tggctccact gggcttccat accagccctt    4260
tccagtgtct taacagctca aagaaaccca tctgtggctt tcttgttagc actgccctat    4320
cacaccttcc tattgcctgt taactaaaat tttgcctgga atgctttaag cttagagtac    4380
tgggtctttg tttcacccga ttgataggag agtgtcatgc agtcagccga actccgactt    4440
ctgtgctgtt taaatcctta ggtaggtctg gggcaaggca caaaccactg tgtattcaaa    4500
gggttatggt gcttgcattc tgtgtgtata tgtttgtaat ttccaaccag agtcgtttcc    4560
cgtgcctgcc ctgcctctgt gcaatctagt ctagtagggt agggaggcaa gctgtggagt    4620
ttgaaaaaaa aaaaaaaagc tagatgagtt taataggctg ttaccccctc cagaacattc    4680
ctcccatgtg gagatgaaac gagaagttca tttctttaac ctaaaataaa gaacaacaga    4740
gataaaattg ttagttcctt attggagcct ggtttccatt gctaatgtac ctgcttggga    4800
ctctgcatga taaatgacgt gtcctggaac ctgaaatctt ttataaaggt taatatcagc    4860
agaaatcttt taattagcta agagcagctt gttctcaagc tgcccgagtt atcttggagg    4920
agagaatcac aggaaatgtt tgatatttct agtaaccagt gttttcagtg cgtggggtaa    4980
agcacactcc tagactggcc agtcccaaag agtgtggcag gacacctgct tgttttccct    5040
gccctctgct atggtgacat ccttgcagac cagtcttgcg tggctggcag acgcaatctt    5100 ttttcttgg gtagagcatt atcaccgctg cgatggaagg accttgtcct cggtgcctcc     5160
ataccagccc tttccagtga aactactgct gtcccggcaa gcccctgtgc gtgtgcatca    5220
ttccgggtag gacaagatgt gaacaggtcc ctcttctttg ggcttaagta gaagttgtgc    5280
tcttctgctt ttacctgtgt gctcttctgc ttttacctgt tctcttctgc ctttctcttg    5340
caagaaacct gtcgaaagct tgctttgcat gccattgctt aaatactttg atggtatgta    5400
tggtatgtgg gataactgag tgggagccgg aattgggggg tggcagggc atccccaccc     5460 ccaccccac atcaaagggg gaatgaccat ttcgttagag aataaagcct gagtcttata     5520
acttcttcaa gcacatgtat gctgggtctc ctggcgtgtg aatgtgttcc cgctgtgctg    5580
tgtggctgtt ttgcagttac tgtagacact gtagtctggg ctctcattat tgcctctgaa    5640
gttgacagga ccaagcctta gtaaggatgc acttgtcttc ctagcccaag agctagggt     5700 gttttatata tatattaact ttcttttta gatttcataa actgctctca ttttctcttt    5760
tctttctttc tttttttttt tttttttttg agacagtctc actctgtcac ccatgctgga    5820
```

```
gtgcagtggc acgatctcag ctcactgcaa cctctgcctc ccgggctcaa gcagttctct   5880
gcctcagcct cccaagtagc tgggattaca ggcacctgcc accacgcctg gctaattttt   5940 gtatttttt tttttttttt tttttttttt tagtcgagac ggggtttcac catcttggcc   6000
acgctggtct tgaactcctg acctcgtgat ccaccgctt cagcctccca aagtgcaggg   6060
attacaggcg tgagccaccg cacccagcct ctggctcttt tcttttgac atgaaatctt   6120 aagttaatta tcttaaactt taagaactag aaggattctt agtccagcac catcagttta   6180
caaacaaaaa aaacttgtgt ccctgagaag ttgtgacttt tccagggcct cctagccagg   6240
ataccagttt ggttttatt atatagctag ccgagtaata ctattaactt gacttctggg   6300
atttcaaagt attctatgac ttgactgttt aagggaatta tgaggcctca ctgaacctca   6360
aaagataatt ttaggtacca tcctggtagc tgtagagcag caacagacca gtaaaagact   6420
tggttggtgt tgcccttctt ctgggtttga ttacatgagt aattgtgtga atagtctcta   6480
agttgtatgc tctgagcttt cgttttagc ttataaaagt gctactcttg ggccagcata   6540
gtatcagaaa ttagctaatt catatggggc agtttaggct ttaactagga aatgatggtt   6600
atcttaatga caaaaaggt actgacaaaa gtcctttttt gaacatgtgt tcaaagaaa   6660 aagagaaact atcaaactaa taactgagtt tgttgaacat cgagattgac tgatctgaga   6720
ggcttaaaac tgattgccct gaaatagact tgcatgtttt ggatgatggc tttgggtctc   6780
ccagagcact tggtttccct tggtgctgat tttttctctc aggattaaag ccccttatg   6840 tgatgttgtt acagcagctt attgcaactt cattcagctg cttgaaaaag aagggagact   6900
gcctctaggt tccatgtgtt ctttcaggga tggtattttg atgttgcgta ttctcttgaa   6960
catgtattct tccctgagaa tttctgtgtg ccgtggtaga agaaatactt gccagaaatc   7020
gccactcatg gtatgctttt gtagtgtcga agtgtcccct agaggtgaca aggcttgtga   7080
tagtgttgat tctaacaagc atgaatcttt cctttattt agcactgtgt gttacgtgcc   7140
agtaatttgc agcttatcct ttgtttctag ctaggtaagc tgggaaatag cctagtactt   7200
tgtctatgtg tttatcttca aaatgtccca aatagccctg ggaaaaaggt cgtgcagctc   7260
aatgggggct ttcaacttac aattttcttt gttttaggct ccataaaaat acagactcac   7320
cagttcctgc tttgatgtga catgtgactc cccagaatac accttgcttc tgtagaccag   7380
ctccaacagg attccatggt agctgggatg ttagggctca ggtaagtaac cttcctttt   7440 tttttttag tatatgtcct ggtttggcca tctgtttttt ttttttaa aaaaaaaaa   7500 aaaaggaaaa gaggaaaaaa atatactact cttggacagt ataaaagtac cccaaagact   7560
aaagacataa ctgtgccaaa ctgtgccata taataaaaaa aagtcacttc cctgagccct   7620
gaaaggtcag tgtgtgtagg gttacttggt cgccacagcg tgatctgggg gcgggcgtca   7680
gattagagcc ggaactggtg atctgcaact tcagttcacc ttgaagcagg tcagctgagc   7740
tgagagcgct tgcactgagc ccttttgcgc tgctgctgtt gccttagcgg tcttcagcat   7800
gtgtttgctt tggtttgggg taaatggctt agtggtcaac attagtgagc agtggtaatg   7860
cattttcaga tatgggaact ggtatgtggt tggttcccta aaggacacc ctcctgaaag   7920 ctgtctcaga acaccggggg ccatggctaa tgtcatgtgc ttgctacact cctcccatgg   7980
taactaaaga gagtacccag atatacatct ggttcttggg actctagagg aggatgagta   8040
ctttgtaaaa acctggggc cccagtcatt ctaggtctga cactcaggtg ctgtatcagc   8100
tgcagtttga actacttggc accattgtgt ggacttagt tttgtaaaaa tgaatggttc   8160 cttaattct caaccttcag gctcaacatc tcaagctgtt tgttgttgtt gttgttgttg   8220
```

```
ttgttttgtt ttgtcttttt gattagtggt cactccgcat ttgatgtttt gacatgtgga    8280
tttcagaact tctgtgtggt aaagcagaat gttccaattg aatttttccca ttttttttcc   8340 cctaagcaaa aatgtgagtt ttcacttatg cggccattgt gattccgact gagaccctaa    8400
gtcgttcttt gttgtctctc tagtggtttc tgacacctca gtgtgaagct gttgtagaca    8460
tccataagaa atagcctgct tagggattat gtgagggcaa ggtttggctg aaggagaata    8520
gaaggtgtgg aaggaagcgg aagaccagaa gagcatcaca ctgcctcaag tcccaaattt    8580
gattctgctc ctgatcctgt gactcaaatt gtcattctct tttactgctg tggggtgtgc    8640
tctgggccca gctgacagga cattcttgt actccacgta tttatgctgg tgggagttgt     8700
atggctagtg ctttgtgctt tgtctcagaa attgtgtgga ctaaatgtaa tatgggcagt    8760
gaatgggttt cttctggaag atgttaggcc tggaggtgg tttgggtttt tacgagtctt     8820
tttctcagat tacagattac gaatggatgt tataaaacag gcagtgttga caccatacag    8880
tttctcctaa gaaatgtaca gagagttcaa cctgaggaag ctaattgaaa ataaactttt    8940
aaaaagaaat gtagaaagag gaaatttaaa aagtatctta tgaatgggaa agatgtagcc    9000
atttgagctt caaagaactt ttgagggaat tctcaaagga cagtacccgt ctttagtaga    9060
taaatgcttg atatctattt ttcttctttt acttttttaaa gaattactaa aataatacat   9120
ggatttatag aaaaatcaaa ccacttaaaa attgatcagg tggctgggca aggtggctca    9180
tgcctgtaat cacagcgctt tgggaggcct aggcgggtgg atcacctgaa gtcaggagtt    9240
cgagaccagc ctggctaaca cggcgaaacc ccatctctat taaaaataca aaaattagct    9300
ggccatggtg gcttgagcgt gtagtcccag ctactcggaa ggctgaggca ggagaatcac    9360
ttgaacctgg gaggcggagg ttgcagtgag ccaagatcac accactgcac tcctgcctgg    9420
gtgacagagt gagactcggt ctcaaaaaaa aaaaaaaaa aaagtatcag gtaaaaaaat     9480
gaaagctccc cgcttaatct ctgctcccac tacccagaat aactgctgtt aatagcttaa    9540
tgtagatcct tctaagtctt ctaagactaa actgtgtact ttttgtgttg taattaacag    9600
gagggttttt gttttgtttt gtttttttctt ttttgagat ggagtcttgc tctgtcatcc    9660
aggctggagt acagtggcac aatcttggct cactgcaacc tccacctcct gggttcaagt    9720
gattctcctg cctcagcctc ctgagtagct gggattacag gcgcctgcca ccacacccag    9780
ctaatttttg tatttttagt agagatgggg ttcaccatgt tggccaggct ggtgtcgaac    9840
tcctgacctc aggcgatcca cctgccttgg cctcccaaag tgctgggatt acaggcgtga    9900
gccaccgtgc ctgcctcag gatggtgtta tatatacata ttctgcattt ttccatctca    9960
tatattcatc tctgcctcat ttcttttaaa tagcagtgta gtccagggct gacttaccgt    10020
catgcatttc gttgtctctc tatgttatta aaaatgctac aggattgaaa ttcctcatgt    10080
gccagtcatt ttgaagaatg gctgcctaga cttggaattt ctggtggata ccaccacatc    10140
actgtccaaa atggctatcc cagttcccac aacagtctga gaaagtgcca ttttcccata    10200
tcgtcccaga attggatata catcttttaa attggtgccg cttggattat tactgaggct    10260
aaacctcaat aatcattgtc atagctctta atgtattaaa gatgttaact ctttgtcatg    10320
cagatatttt cctgttttgt cttacgtctt gattcttgtc tttctgatat ataaaattta    10380
tgttatgatt tattcttttg ctttcatact taggaaatcc tttttttactc ttttttttttt   10440 tttttttttt tttttttgag acggagtctc gctctgtcgc ccaggttgga gtgcaatggc    10500
gtgatcttgg ctcactgcaa gctccatctc ccgggttcat tccattctcc tgcctcagcc    10560
```

-continued

```
tcccgagtag ctgggactac aggcgcccgc caccacgcct ggctaatttt tttgtatttt   10620
tagtagagac agggtttcac catgttagcc aggctggtct cgatctcctg accttgtgat   10680
ccgcccgtct ctgcctccca aagtgctggg attacaggcg tgagccaccg cgccccgcca   10740
ggaaatcctt tcctactctt aacaacagat caatagtcat ctatattttc ttcctaaaaa   10800
acctgatgat gtattatatt catacatacg tatttaatac atacaaaagg gccagatgcg   10860
gtggctcatg cctgtaatcc cagcactttg ggaggctgag gcgggtggat cacctgaggt   10920
caagagttca agaccagcct ggccaagatg gtgaaatccc gtctctacta aaaatacaaa   10980
aattagccag gcgtggtggc gggcacctgt aatctcaact actggggtga ctgaggcagg   11040
agaatcgctt gaacccagga ggcagaagtt tcggtgagcc aagatcacgc cactgcactc   11100
ctgcctgggc gatagagtga ggctctgtct caaaaataaa aaataaaaat aataatttta   11160
tagttaagtt gccctgtgtt tttcctgtga ttaaaaaaaa aaatacctgt tttgtattta   11220
actttggggt gggataaggt atagcccact tagtcagttg tgtctaagcc acttgatgaa   11280
ccagtcaatc cagtcttcac ctttaacaaa tgctgatttc ttcaagtgag caaaatatct   11340
cttaaacttt ttcctatttt ctctataaag ttgctttttt ctgaattttt tctttatgag   11400
gcttgatggg cagccctatc agcagacaat cattcattca cccaacaaat atttgagtat   11460
ctgcttcaag ccaggggcag tgctaagccc tggaagtggt atcttctcct tatccgggag   11520
tggggctaca gtgttcattc cagaagactc aagaaaatag cagatcatca caaaagtagg   11580
ttttacataa atgaggagga atccacaggg ttgtgtatat gtgtgtgtat tttaaattct   11640
gacataagtt ggagctttag ggtagactgt gacataagag tagtttgttt tccaactcat   11700
gtaattgccg gctgattttt gtcttgaatt atgataatgg taacttctgt tgaaacaatt   11760
ctgtattcat cttagcttgg ttgggatgca ataaagtttt tgtactggta aaatgataaa   11820
ttttcttcca tgatgatttt gaagcttttc tgtaacacct gataaaaata gaggggccag   11880
gcatggtggc tcatgcctgt agtcccagct actcgggagg atgaggtgag aggatcccat   11940
gagcccagga gttttaggct acagtgagcc atcatcacac cactgtactc ctgtactcta   12000
gcctgggcag cctcgttctt tagagtaaga cactgtctct ttaaaaaaaa aaaaaagaa   12060
aaagaaaaa aagaaaaggc ttttagtgaa tatatttta gggtagcaag tgtaattttt   12120
ataaattgca ttatttgaat ctaataaata ccctcaaagc tgaagtcgaa ttctgatttt   12180
gattgaaaat attttttact taaaggaaga gggatagaat aaatgacacg attaaggaaa   12240
agacttcttg tataaggccg gggtttttta aatgattttt tgaatagtta gatggacaat   12300
acggaattaa aaaggtggtg taaaaagtta tacggggctg gcacagtgga ctcacgcctg   12360
caatcccagt actttgggag gccgaggtgg gtggatcacc tgaggtcagg agttcgagac   12420
cagcctagcc aacatgacga aacatcattt ctactaaaaa tacaaaaatt agctgggctt   12480
ggtggtatgc acctgtaatc cagctactcg ggaggctgag gcagaagaat cgtttgaacc   12540
caggaggcag aggttgcagt gagccaagat cgtgccattg cactccagcc tgggcgacag   12600
agtgagactc catctcagaa aaataataat agaaaaaagt tatatggggc tgggcatggt   12660
ggctcatgcc tgtaatccca gcagtttggg aggctgaggc agcttgatca cttgaggtca   12720
ggaattcgag actagcctgg ccaacatggt gaaactccgt ctccactaaa aatacaaaaa   12780
ttagccaagc gtggtggtgc gtgcctgtag tcccagctac ttgggaagct gaggcaggag   12840
aatcgcctga acctgggagg cagaggttgc agtgagccaa gatcatgccg ttgcactcca   12900
gcctggacga caagagcgga actccgtctc aaaaaaaaaa aaaaagagt tatattgtaa   12960
```

```
agtatctctg ctaccctgcc ccaaacattc atttctttcc ctggaggcag ccactattac    13020
ctgtttcttt aaaaaaaaaa aaaaattgtg gccgggcacg gtggctcacg cctgtaatcc    13080
tagcactttg ggaggtggag gtgggtggat catgaggtca agagatcgag accatcttgg    13140
ccaacatggt aaaaccccat ctctactaaa aatacaaaaa attagccggg catggtggcg    13200
ggcacctgta gtcccagcta ctcgggaggc tgaggcagga gaatcgcttg aacctgggag    13260
gcagaggttg cagtgaactg agatcacgcc gctgcactcc agcctggcaa cagaatgaga    13320
ctccatctca aaaaaaaag cgtgtgtgta cccgtgtgtt aaattttat tataaaatat       13380 atataacagg ctgggcgtgg tggctcacgc ctgtaatccc agcactttgg gaggccgagg    13440
caggctgatc acgaggtcag gagatcgaga ccatcctggc gagcacggtg aaacctcgtc    13500
tttactaaaa atacaaaaaa ttagccgggc atggtggcgg cgcctgtag tcccagctac     13560 tctgagagcc tgaggcagga gaatggcgtg aacccaggag gcggagcttg cagtgagccg    13620
agatcgcgtc actgcactcc agcctgggcg acagaccgag actccgtctc aaaaaatata    13680
tatcgatata tataacaatt tacagtttta atcatcttaa ctgtacagtt cagtggcact    13740
gagtacattc acattgttgt acagccatta ctaccatcca tctctacaac ctttcgtctt    13800
gcaaaactga aatttcatac ctattaaaca ctaactccca cttctcccct ttccccacc     13860 ccaccctctg gcaactacta ttctactctt tgtctctatt ggacatattt ttgtgtgttt    13920
aggtttgtgt atatatttta catgtgtgta taaatacaca agggtatgtg ggcgttgtgt    13980
ttttacacat actataaaat attgtgcaca tttgtttatt ttaatgtatc ctgtagatta    14040
tttagaatcg gttcatacag agccgtatca ttccttttaa gggttgggtt taaatagtct    14100
gttatggatg taccacaatt tatttaacca gttttaaat ttttttactta ttttttttaa    14160 tgttttttta gagacaggat cccactccat cacccagact ggagtgcaac agcatgatca    14220
tagcttactg cagccttgaa ctccggggct gatgtgatcc tcccacctca ggctctcttg    14280
tagctgggac tacagggatg tgccgccatg cctggctaaa ttttttattt ttattttat    14340 ttttattttt ggtagacacg gggtttcact gtgttgccca ggctggtctt gaactccttg    14400
ggcttgagta atcctcctgc cttggcctcc caaagtgccg agattacaac catgagccat    14460
ggagcccgac aagagtagcc ttttatttgc agaccattag agaaaaagtt gcgtgtaagt    14520
agataagcat acgaatttat cactgcaata ctgtttgtag agatcacaga gctgttaggc    14580
taggaagaag ttttttagcag ttagcactag aaagcaaaac tttggaaact tccatttcat   14640
caaaagtgac ctcatctgag tagggcatgt gagggaagga ccttttttact cgacaagggg    14700 aacttgccag ttcttgtttg tgaaccttga agaaagtgga gcattttat tttgggacca     14760 ttctaggttg tggtagttcc ttggtactcg gggttggaga atctccctct gctgctggac    14820
cttctgcctc ctcatgctgt aatatgcata agaggtgtcc tagaagtatt caggaacagg    14880
ctgtggttgc tttgttgttc tgtgactgtt gaactcttta tatagcagta ctttttttaag   14940 ctgtactaat tgagcattta ttatgtgtca gttactgtgc tagctgctgg aaactatcct    15000
accctcagca gtcttctggt ctaatgggag gtacagacag gcaaatgggc tatgactta     15060 caagaggcta acttctgtga tggagagaag ttccagccac taagggagca cataaaaatc    15120
agaggagatc ctaccaagaa ttgggaggta ggtcagggag gagacttctt tgaaaaatgg    15180
catctaagac ctgaacagca aggaaacatt agctaggtca aggacaaagc atcagtgggg    15240
agagatgcat gagtcttttg gaaggaccag catgtgtaga ggctctgaca ggagagaatc    15300
```

```
tctcaggccc attcagagag tccactgtgt gaagacgagg catgaacaac cagccaggac     15360
atgtggagag gagcattttt cttttttttct tttttctttc ttttttttt tttttttttt     15420 ttgagacgtc tttctctgtc acccaggctg gagtgcaatg gcatgatctc ggctcactgc     15480 aaccccact tccagggttc aagcaattct tctgccttag cctcccaagc agctaggatt      15540
acaggcaccc gccaccatgc ccggttaatt tttgtatttt tagtagagac ggagtttcac     15600
catgttggcc tcaaactcct gaccttaggt gatccacccg tctcggcctc ccagagtgct     15660
gggattacag gtgagagccc ccacgcccgg ccaggctcgg ctttctttcc aggccccgtc     15720
acactcttag atgttccctg ggccccagaa ggcagcgtga ggtgctctgc ccatctatgc     15780
tgtccttttc caccccaccc tatccactgg gcccctgggg ctcccactcc actccaggtc     15840
tcttcatgga cccttctttc ccttcacttc tgtcccagga gacctgggag actcatggga     15900
acaggcatca tcttctccag cacagttcat tgtctaatgc acgaaagtgc tgggctgtga     15960
gaaggtcagg agcttacatg gaatgggagt cagctgtggt acaaagtacg ctgcttagtt     16020
ctactgattt tttattttt attttacat aagactttga tggtaaagga agcagtgtgt      16080
gagcaagctg actcctgtct tgtcaagtac caggtccact ctgatgagcc cctgtggaca     16140
gcactgctgt aactccccaa gcctgggctc aggaggtggg ccctaagcgc tgttcccagc     16200
tcttcctcca tgctgtcagc tcttccacca ttcttcctgg cgtcattcta aggtcctgtc     16260
ttcccccgcc ctcttccttc ctggcttcta cgctcagctc aagtagtagc tgtttgggta     16320
cttttcaccc agacttagga aatgttatca gttggtcgta ttcctgtcag ccctcttact     16380
atggaactca aataggacag attcagctga attcccagcc ctgtggttgc actctttgtc     16440
tgccctgctt ccccaaggta gcctgctccc taaaggtcac cgagatactc cccatgcaag     16500 gttttgttg tattacacat gacaacatgg aataaagtgt tttgcaaatt tactggatga     16560
tatcctacta tgtggaacat cctacaactt actcttttca ctcaacattt gacttttgaa     16620
cctggtctgt attgctccgt gcagaccaat gttcattcat ttgatatgtc tccttgtgcc     16680
atagaaatag ttttacaata gaagcctgtc cagagccatg agggagaagg ggattgtaga     16740
gaaacaagga ttggcatctg gtttatgttt acatcccttta gtcctgttaa ccgagaagaa     16800
gatattttta tttccatgtt tgcgaaagct ttccacaaaa aaaagcatcc attttctaga     16860
cttattaata gggcagtcca aaggttttat tttagatttt gaaagaaagc aaagtaggct     16920
tctgagatat gcacatttcc ctgtgtccct gtctcttttg caacattcca cattgctgct     16980
aaaacttgaa catgagcact ttcaagcatg tgcttacttt ctatgtatga ctcatttttt     17040
aaaacattaa agcattttcg gccgggtgtg gtggctcacg cctatattcc tagcactttta    17100 gaaggccgag gcgggtagat cacttgaggt caggagttca agaccagcct agccaatata     17160
gtgaaacccc atctccacta aaaatacaaa aattagccgg gcatggtggc gggcgcctgt     17220
aatcccagct actcgggagg ctgaggcagg agaattgctt gaacccagga ggtggaggtt     17280
gcagtgagca gagatcgagc cactgcactc tagcctaggt gacagagcga gactctgtct     17340
caaaaaaata aaaataaagc attaaagcac tttgtctggt ggtatgtaag ttttggcatt     17400
acttagataa gttgtatttt aagtcttcct acacacaata acttatttt aaaatacaag      17460 tttctgtgta cttccgggtt ttgtgttttt gtaaacagca gaaggtatta gtccatatta     17520
agtactaatt tgttctaata ttttcagctg tttttggaat tacacttggc aaaaaaatag     17580
acaaatgtct gcagttgtga cagtttgttt ttttgttctt tttaactcca gaataaataa     17640
ttctagtgag tttttttctt ggcttgtaag aacatgggaa tgattagagt catcataaca     17700
```

```
cttaagtagt tatagaaggt tgaacatctg tagtcagttg tataaaattt cctagtcatc   17760
cttccaggtt gtttaagaca aacaaataca tagtattat taagctctta taaattttaa   17820
ttgtaaaaca tcattgtaca aaactttgaa aatgcgtata ggtacaaaga taaaaaatta   17880
ggccaggcat gccatggctc acgcctgtaa tcccagcact tgggaggcc aaggtgggag    17940 gatcttttga gcccaggagt tcaagaccag cctgagcaac atattgagac cctatctcta   18000 caaaatatc ataaaacaaa atagaatcac tctggcgatt ccactatcca aaaaaaaaa    18060 aaactgctgt taatatttgg tatgtatctt tctagaccaa ggcctccaac tttggttgag   18120
aattcagccg ggtctgtgac cttggatggg aaaaacattc actctttatt ttcactaatg   18180
tctctgaaaa cccagatttt tagctgggca tggtggctcg tgcctgtaat cccagtgctt   18240
tggaagcccg tggagggcag atcacttgag cccaggagtt tgagaccagc ctgggcaaca   18300
tagcaagacc ctgtctttta aaaaaaaaaa aaatccagcc gggtgtggtg gctcatgcct   18360
gtaatcccag cactttgaga ggctgaggca ggcagatcac ctgaggtcag gagtttgaga   18420
ccagcctgac caacatggtg aaatcctgtc tctactaaaa atacaaaaat cagccgggca   18480
tggtggtggg cgcctgtaat cccagctact ccggaggctg aggcaggaga tcacttgaa    18540 cccggaaggt agaggttgca gtgagccaag atcacaccat tgcactccag cctgggcgac   18600
agagcgagac tctgtctcaa aaaaaaaaaa aaaatccac attttcttca atgacaattg    18660
taagcaacag atcatggtag tattagaata gcagtgactg tcaccagtag agatcaaaga   18720
tactttcata tcatattata gttgttacag atattttgaa atatatatgt ccatcactgc   18780
ttcaaactta aggtaattat tagacccatc tctagatctg gttatttaat gatttactga   18840
agaagcacat attatttgag aacgaactct tgaaatatgt tgttaatttc tgtgcatttt   18900
acacatttca aaacattctt ctgaggaggg gtccagaagg ccaaagggt ccatggcaga    18960 aaaaggttaa gaacacctgt tctgtacttt gtaccatgtg gctacaaata taaaaacaga   19020
cgttaagccg ggtatggtga tgcacacctg tagttccacc tacttgggag ctgaggtgg    19080 gaaaatcact tgagcccagg agtttgaggc cagcctgggc aacagagcaa gaccccatct   19140
cttaaaaacc agtcagcact tgactagtca gttagtgggg gaaaacacag gtacagtaaa   19200
aggagtcaaa attacactta aacttaggtc atcttattat atcaaacatt tattaacatg   19260
tttagtgttt tgtgtatatt atgcaaagtg taatgcaact aaaactgttt aacacttctc   19320
gatatcacat aaatttgttg gtgcataata gcctaaaagt tacttttgct gttggcattt   19380
tattttatta cttacttatt tatttattta tttatttatt ttgagacaga gtcacactgt   19440
cgccaggctg gagtgcagtg gtgcgatctc agctcactgc aacctctgcc tccctggttc   19500
aagcgattct cccgcctcag cctcctgact agctgggact acaggtgcgc gccaccatgc   19560
ccagctaatt tttgtatttt tagtagagat agggtttcgc catgttggcc aggatggtct   19620
tcatctcttg accttgtgat ctgcccacct cggcctccca agtgctagg attacaggca    19680 tgagccacca cgctgggcct gctgttggca ttttaaacat ccttctagag tctttcttat   19740
ttgcctgtaa gcacgtacac atgttgttgt tgttttgaga caaggtctgt cgcccaagct   19800
ggagcacagt ggtgcaatca cagctcacta cagcttcgac ctcttgggtg caagtgatcc   19860
tcccaatcag cctcccaagt aggtgggact acaggtgtcc gctaccatgc ccagctaatt   19920
tttgtatttt ttttgtagag acggagtttc accatgttgc ccagactggt ctcaaactcc   19980
tttgctcaaa cgatccttcc gcctcggcct cccaaagtgc cgggattaca agtgtgcacc   20040
```

```
tctgtgcctg gcccacatat tgttttagat gaatgagatc atatatgtac ttttgtaact    20100
tgctaccttt cctcaacaaa atgttgtaaa tatccatgtc cataaaaata gacgtatatc    20160 ttcactttc cctaaaatga aaataactta acttgcattt tctttttgt ttttgttttt      20220 gttttgagac aggctcttgc tctgttgctc aggctggagt gcagtgatgt cacagctcac    20280
tacagcctcc acctccagtt tcaagtattc cacctacctc agcctccaag atagctaaga    20340
ctacaggcac atgtcacgac gcctggctaa tttttaaaat attttttgca gaaatgggat    20400
ttcactatgt tgcccaggct ggcctcaaac tgctggcctc aagtgatctt cctgccttgg    20460
cctcccaaag tgctgggatt acagtcgtga gccactgtgc ccagcctgca ttttcttatt    20520 ataaagtaa tacatgttca atggacaaaa aattttcaga aaatatgcaa agatgaaaag     20580
taaaaattgt ccataaatct gtcatctaca gataaagata acttctggat aatgttttc     20640 taccatcatt tttagtaatc acataacatt tcgttgtatg tctatgcctt catttaatta    20700
agaggcattt ccattatttc tgcatgttca tgactctgaa tgatgatatg tctgcctgct    20760
gatggctaca accctgtttc tgcatttcaa acctctctct tgagctccag atttgatggc    20820
ctcgtcagca tttacttgag ttgctcataa gtgtctcaaa tttaacaagt cccagtcttg    20880 attttttcc cccttcaaac ctattcctca tgttgtctct atttcagtaa acaatatcaa     20940
catccaccca gttactcagt ccaaaattct aggagtcatc cttgattctg ctctttcttt    21000
tttttttttt ttttgagacg gagtctcgct ctgtcgccca ggccggactg cggactgcag    21060
tggcgcgatc tcggctcact gcaagctccg cttcccgggt tcacgccatt ctcctgcctc    21120
agcctcccga gtagctggga ctacaggcgc ccgccaccgc gcccggctaa ttttttgtat    21180
ttttagtaga cggggttt caccttgtta gccaggatgg tctcgatctc ctgacctcat      21240
gatccacccg cctcggcctc ccaaagtgct gggattacag gcgtgagcca ccgcgcccgg    21300
cctctttttt ttttttgata cggagtctca ttctcgtcat ccaggctgga gtgcagtggt    21360
gcaatcttgg ctcactgcaa cctccgcctc ccggggttcaa gcaattcttc tgccccaacc   21420
tcctgagtag ctgggcctgg ctaatttttt gtatttttag tagagatggg gtttcaccat    21480
gttggccagg ctggtcctga actcctgacc ttgtgatccg cccacctcag cctcccaaag    21540
tgctgggatt acaggcgtga gccactgcac ccgccctgat tctgctcttt ctctcatcat    21600
ccctgatctg tcagcaagtc ctgttaggcc aaccacttct cagcatctgc actgccagta    21660
tgctagtcca agccacaaaa cacctctcag aggtacgcaa caggactttg ttgttgttgt    21720
gtgtgtgtgt gttttttttt ttttacggt agaattattt tataacttga agtgtaggga     21780
tgaccttcct tttaaatttt tatttatttt cttaattttt tattcccata gattttaggg    21840
gaacaggtgg tatttggtga catgagtaag ttctttaatg gtgatttctg agattttggt    21900
gcacccatca cccgagcagt gtacactgaa cccaatttgt agtctttat ccctcaccc      21960 ctcccaccct ttccctcaag tccccaaagt ccattgtatc attctgatgc ctttgcatcc    22020
tcatagctta gctcccactt atgagtgaga acatacggtg tttggttttc cattcctgag    22080
ttacttcact tagaataata gtctctagtt ccatccaggt tgctgtgaat gccattaagt    22140
cattcctttt tatggctgag tagtattcct ttgtatatat atgccacaat ttctctattc    22200
actttctgat tgatgggcat ttgggctggt tctatatttt tgtaattgtg aattgtgctg    22260
ctataagcat gcgtgtgcaa gtatcattat gcaacgggac ttcggatgac atattgaaca    22320
acttcctcac tgatatcctt gtgaaacgct acatatttca tgggtctgtt tgttataccaa    22380 acactcaatt ctgaatgatg gaattatttc acatttagtc tctttttcat ctagccatta    22440
```

```
tagtttagtt taaacaccaa gttccattcc tgctgcatgc tgaaggattt gcagtacatc   22500
aggctatagt ccatcaattc attccacaat tgagtaagta aggtatctat agtacctcag   22560
gccctgtgtt aggcagggat ggggtaacct agacagattt ggtacctgtc ctcatggagc   22620
ttgactttag cggcagagac agatcttaga taattgtacc agtacttaag tgttcagaag   22680
gacaagtatg gaggtgggag ccactccagt cctctacagt cacgtgctgc acaacaacgt   22740
ttcaaccgac aacagagcac acatacagtg gtgttcccat aagattagaa tgccatattt   22800
ttactgtacc ttttctatgt ttagatatac aaatacttac cattgtgttc cagtgatcta   22860
cagtattcag tatagtacca tgctgtacag ttttatagcc caggagcaat aggctatata   22920
ccgtatagcc taggtgtgta gtatgctaca ccatctagat ttgtgtaaga acactctctg   22980
atgttagcac aaataaatcg cccaatgaca catttctcag aacatatccc tgttgttgag   23040
cgactcatga ctgtacaatg ggggaacagc tcagcctgcc ttccccaagg aggcaacgcc   23100
gatgcaggga accgagggtt gaacagaagt gggcaaggtg cagagaggaa aaaggctttc   23160
cagatggaga agagcatgtg tgaaggccct cagtctggca agagcttagt cctgtgtggc   23220
aggagctgaa cgaggggtta ggggagagtg gcaaagggtc cgggccatca gagaggtcaa   23280
caggggctgg atcatgcagg attttgaatg ttaacatcag agcgatagaa aacatgaagg   23340
gtaaggtggt ttgggttttg aattttttatc aaaatattgc aactactcgg caacaagtta   23400
gatataacaa aagaggtcat cgtaaaaaca gcagtctacc ccttcccctt cccttccctg   23460
actcagacat gacagctttt aactgtttct gattttagtt cctttgatgg ttacctccaa   23520
aattaaatca tatgcttata catctttctt gatttgccaa ctttagggaa ctgtgttaac   23580
tccctgaaat gaaagagaat gacttagctt acgttacctc cccatgttga aattcatatt   23640
cacatttctc tgtaatttttt tttttgagat ggagtctcac tctgtcgccc aggctggagt   23700
gcagtgatgt gatctcggct cactgaaacc tctgcctccc gggttcaagc aattctcgtg   23760
cctcagcctc ctgagtagct gggactacag gcgcacacca gtgcactggg ctaattttttg   23820 tattttttagt agaggcgggg tttcaccatg ttggccaggc tggtcttaaa ctcctgacct   23880
caggtgatct gcctgccttg gcctcccaaa gtgctgggat tacaggtgtg agctaccatg   23940
ccaagcccac atttctctgt aaattttaaa cagtatttta gtccatatgt cagttcccct   24000
ctttttaaga taaggatatt aataacccta cttttccttc cactttccct ccttaacttc   24060
tgcgtcttaa aagctgtact tgaccatacc cattcttgca tttgttaaca tgtgtgttct   24120
gccctgcaac cacagccaag ttgtagctta attctaaagt cgaaaataac attatttaca   24180
ttattacaca tgtgagtatt gttcttggcg agaccaaata atgaatgtgc ccaggattac   24240
atttccttct ttacagatct ggaccactca aaggagaatg accaatcaag gtcaaatgga   24300
ttcccttttc ttagactctg tcacctgctt aaaatccttg ctaggattta atctacttca   24360
tattcaaacc ttggcttgct tatatagctc tttgttttgc ccaccatttc tagttgcctt   24420
tttattttgt ttactattcc tccttgatta tgttgtaaaa tgctattagc agtgctgttt   24480
atttcgtacg attcggcttt tcccccactg aagacctttc tcttggaagg cctctgccct   24540
tctgcaatct gggcaagtat ctgctctttg atttaaggtt gcatatacag ctgtacctgg   24600
accttctcct cactgggctc ttgggttgga gcccgtgtct taaaacccat atcttccttt   24660
cacatggttt actccctcgt tttctggact gcatccttaa ataatgtgct cagatagagt   24720
gcatggggag taaactgtag tggataccgt tgtcacctac cccatatcca tttcttcttt   24780
```

```
gcccattcct aacagaatcc tgatattatt cacctttcta ccttattccc aacttcagaa    24840
aggatcctta agtcattcca cacattgcat tcctttggca actgttactg gtcaaggatg    24900
gacatacgat ctaagttggt tcactcagac tgaagggaag gacttccatg gcacgttcag    24960
ggaagacttt ctcttttttct ctcactggag taagtgagaa aggtgttgct gggggctctt    25020
ctgtaacctc agactgaggg acaaagcctg aggataaagc ctgctcacca aggaaggcgg    25080
agcagagaaa cgggaagaac ctgggtcttg atgccgttgc ttagctggtg attgcactgt    25140
ggctggggcc tgtcctacct gagctaggga ctcagatagg atggactttc ttactgaatg    25200
agccagcttc agttttctttt tctgttactt gtaaccaaaa gcattgtaac agataggtct    25260
tctgagtcac tgcatgcctg aaatacccttt cttctactct tacacttgat tggctgagta    25320
tagggttcca agttgaaaat cattttttct cctaacttttg gaggcatctc ttctagtatg    25380
cagagtaaca aatgcaacaa atgcctgatg ccaatcttat tatggttctt ttgtaggtgc    25440
ccttcttttc tcttccttcc ctggaagttt ttaggattttc gtctccttat ttttagtgtc    25500
ctgaaatctc atgagaatat gtctagagtt gtgtcttgtt cactcgttgt actgtggtca    25560
ttcaatctga atactttttgt caactctttt ttttaaaaaa aaattactaa tttacatgct    25620
ttcattttct ctatggggac tactgtttaa cttttggaccct cttatattgg tcttctgtct    25680
tctctcatat ttttcattta ttgggcggtg ggggtgctc tgaattttgg aagatctcct    25740
gcatttatt tcttttttcct tttttctttt ttttgaggc agagtcttgc tctgtcaccc    25800
aggctggagt gcagtagcct gatctcggct cactgcaacc tctgccttcc aggttcaagc    25860
aattctgcct ctgcctccca cgtagctggg attacagacc tgcaccacca cgcccggcta    25920
attttttgtat ttttaataga gatggggttt caccatgttg ccaggctggt ctcgaactcc    25980
tgacctcaag tgatccgccc gcctcagcct cccaaagtgg tgtgagccac cgcacccagc    26040
ctcctgactt tatttttctat cccttctgtt aaattctttta tttcagccaa acctttttttt    26100
tttttttttt aacttactgt gaagcctgtg tgcctactgc ctagattaga caattgttaa    26160
cattttggcg tattttcctg gtctgtatag atagggtgca tttttatacc tttttgctca    26220
ccatttaaaa ggaactcaca gatgtcacga catttcacccc ctaagtactt cagtatacat    26280
ctcctaaaaa taaggacatt ttccaatata agcacaatac cccgatcaca tctttaaaag    26340
ttaacaataa ttctctaatg ttatcaggca cccactttaa attcagatttt cctccaaatg    26400
tctcttatcg ctgttgaggg gctccaaagc aattaagatt tatacattgc atttgaatat    26460
gcttcctttg tctcttattt atttatttat tttattttga acagagtct cgctgtctcc    26520
caggctggag tgcagtggtg tgatctcagc tcactgcaac ctccgccttc aggttcaag    26580
cgattctcct gcctcagcct cccaaatagc tgggattaca ggtacgcacc accacgccca    26640
gctaactttt ttgtattttt agtagagaca gggtttctac taaaccatgt tggccaggct    26700
ggttttgaac tcctgacctc aagtgatctg cccgcctcgg cctcccaaag ttctaggatt    26760
ataggcgtga gccaccatgc ccagccccttt tgtctctttt aacaagaaca gcctacccac    26820
ctctccttca cttgtgatac tgacttttttg aagcagtcag cccaattgtc atctagaagg    26880
gcccacattt taagatacat atttttagag atggcgtgtc actatgttgc ctaggctggc    26940
cttgaactcc tggcctcaag taatcctcct gcctcagcct cccaggtagc tgggactaca    27000
ggcttgtgcc accacgacta gctggcccac attttagatg tctctctttt cttgtgatat    27060
aatttaactt gtttgtccat atatattact tgtagacaag aagttaggtc tacaggcatg    27120
ttcaggttaa acatttttggg caagaatatt tcataggcag tactgtgtac ttcatatagc    27180
```

```
atcagctcac caggcactta atggttggtt accctgtggt ttgtgatgct acgttttaac   27240
acttgattaa agaaggaggt gactgccaaa tctccccatt gtagacatac agttttcctg   27300
tggtaattga tatataatct gtgatgtgat gctttggcac catacaaata tcctattgcc   27360
caacagccat ttgcataatt attttagcat tcattgatcc ttgcctgaaa ccattattac   27420
attgggggtt gcaaaatgat agttttttta attgtcacct cttctacatt tagtactgtc   27480
attcctctgt aatgaatttt ccctcatcaa ataaggaggc attatatttc ctcctaaaaa   27540
gacagtatag atgcttaatc tttgccttta ttacatttca gagtaaggag ttggtagaat   27600
aatcacctca aatggtggca aaatatttgc tgttgtgttt cctttctct ttcatgtcaa    27660
tatggactca tagggattta tttattaaat gttttacaat tcaaattggg tcaacaagag   27720
tcccttcatg ttggttccta tattctcctg cataccctc attaattagt ctttgagcaa    27780
tttcttgttt tctggcacaa gatattccat cccaatatgt gcttttcgtg tcctagaact   27840
gattccaagg agctctggtt ccttatagtg gcaacggtat ttagaatcca acatgtgggt   27900
actaaatgtg ctgattctta ctggggtaac attatatcta ggcactttca gaggacatcg   27960
ctagaaaata tattcagttt ttattttta tttttaattt ttttgtagag acaaggtctc    28020
actatgttgc ccaagctggt ttcgaactga gctcaagcga tcctcccacc tcagcctccc   28080
aaagtgctgg gattacatct gtcagggcaa actgctggta aatattttca caaagaaaa    28140
ataaaaaaac caaagtgctg ggattacaga tgtgagccac tgtgccctcc attttttttt   28200
taagtcataa atacataatg atgtcttcta tggcaattta acattacagg gttcttcctt   28260
aacttttttt tttttttttc ttttttttga ggcagggtct tgctctattg cccaggctgg   28320
agtggtgcag tggtacaatc ctaattcact gcagcttcaa atgcctaggc ttcaaacaat   28380
cctcctccct cagcctcccg agtagctaag actacaggtg catatcacca tgcccagcta   28440
attttttaaaa attttttgta gagatggggg gtctcgttgc gttgcccagg ctggtctcga   28500
actcctggcc tcaagtgatc ctcccatctc gatttcccaa agtgctggga ttacaggtgt   28560
gagccaccat gcctggccaa cttttatttg atctgtatat atctttcct tacactgaaa    28620
atgttgggtc ttactaatgt taacatagtt acttatttgc tttatcttgt aatagacata   28680
aaattacaaa attataatac caatattacg ataaatagct gggcatggcg gcgctcgcct   28740
gtagtcccag ctactcagga agctgaggtg gagggactgc ttgaacctaa gagtttgaag   28800
ctgcagtgag ctgtggttgt gccactgtac tcctacccgg acaacagagt gagtgggggg   28860
aaaaaaaaga aataatggaa gatccagaga aagcccaaa tatttaaaaa ttaaacaata    28920
cactttgcag cttcctcacc tctctcagcc ttcatagaat tgaagagagt tagggccttg   28980
cactagatta ggctttgcct taaggaaatg ttgtgtttga tttgatcttt tatccagacc   29040
attaaaactt ccttaacgtt tattagtaat aaggctattt cactttcata tcatttgtgt   29100
gttcactgga gtagcacttt tagtttcctt caagaacttt gattcacaac ttggctaact   29160
ttggtacaag aggcctagct tttggcttct cggctttcaa catgcctctc actaagcctg   29220
atcatttggt ttttggttta aagagaaaga catatgactc ttccttttac ttgaatgctt   29280
agaggccatt gtagggttat taattggcct aatttcagta ctgtcttgtc caagggaata   29340
gggaggccca aggagagaga gagagatggg ggaacagctg attggtggag tagtcagaat   29400
atacacattt atcacttaag ttttgccatc ttttctttt cttttctttt ttttttttg     29460
agacagtctt gctctgtcac ccaggctggc atgcagtggc atgatctcag ttcactgcaa   29520
```

```
cctctgcctc ctgggctcaa gcaattctcc tgcctcaacc tcccgagtag ctggtattac   29580
aagcgtgcgc caccataccc agctaatttt tatattttt  agtagagaca gggtttgcca   29640
tgttggccag gctggtctcg aattcctgac ctcaagtgat ccacccgcct tggcctccca   29700
aagtgcgggg attacaggcg taagccactg ccgcctggcc aagtttgcca cctttttat    29760 ttttttatt  ttttgagatg gagtctcact ccatcaccca ggctggagtg cagtgatgca   29820
atctcggctc actgcagtct ctgcctcctg gattcaagcg attctcctgc ctcagcctcc   29880
cgagtagctg ggactacagg catgtgccag cacgcccagc ttgttttttg tattttagt    29940 agagacgggg tttcaccatg ttggccaggc tggtctccaa ctcctgacct caggtgatct   30000
gcccggctca gcctcccaaa gtgctgggat tacaggcgtg agccaccccg cccggccaag   30060
tttgccatct tttatgggtg cagtttgtgg tgccgcaaaa tgatgatagt agtaacatca   30120
gagagcattg atcacagatc accataacaa atataataat gagaaatttg aaacattgtg   30180
aaaattacca aaatgtgaca gagacatgaa gtaagcacat gctattggaa aaatggcact   30240
ggtaaacttg cttgatgcag ggttgccaca caccttcaat ttgttaaaaa ctcagtatct   30300
gcgaagtaca gtaaagcaaa gcacaatcaa atgaggtgcg cctgcatatt acaaccaaga   30360
ggcttttcgc agaaacacga gtgtgcttca acattcaaaa atcagttggt gtaattcacc   30420
acattaagat aataaaggag gccgggtgcg gtggctcaca cctgtaatcc cagcactttc   30480
agaagccgag gtggacagat cacttgaggc caggagtttg agagcagcct ggccaacata   30540
gtgaaatcct gtctctacta aaaatagaaa aattagccgg gcagggtggc acgcacctt    30600 agtcccagct attcgggagg ctgaggcagg tgaatccttg aaaccaagag gcggaggttg   30660
cagtaagctg agatcacgcc aatgcattct agcctgggca acagtgagac ccagtatcca   30720 aaaaaaaaa  aaaaaaaaa  aaagataata aaggagaaaa accatatagt ctattcaata   30780
aatacagaaa acgcatctga caaaattcag tgccctttca tgataaaaat tcagcagatt   30840
agaaatagag gaagtgcatg tatgaaagag ctacagatag attgtactta attgtgaaat   30900
attgaacatg ttaccccgaa atcaggaaaa aaggcaaaga tgtccactct aaccacttct   30960
attcaacatt atactagagg tcatagccag tataatgagg caagaaaaaa cataagaggc   31020
attaatattt aaaggaagta aaactgtttc tatttgtagg taatgtcgaa aatgtgaaag   31080
aaactatcag aacctgctag aactaaaaag tgaattcagc aaggtctcag ggtacgagat   31140
cattcaaaaa ctaatcagaa atgaaatttc aaatgcaata tcgttaggaa taatttaata   31200
agaaatgtac aagatttaca cgctgaaact gaaaatgttg ctgaaagaaa ttaaagacct   31260
aaataaatgg aatgttgtac catgttcatc agctgaaaga ctaagtgtct ttacagtgtc   31320
agttctccct tcattgaact gtagattcat aaccccagtc ataactgcag gttttttt    31380 gtagaaattg attgtaaaat gtatatggaa gctgggcacg gtggcttatg cctgtaaacc   31440
agcactttgg gaggctgagg cagacagatg acttgaggtc aggaatttga gaccagcctg   31500
gctaacatga cgaaacccc  tctctacaaa aaatacaaaa attagccaga catggtggca   31560
cacacctgta atcccagcta cttgggaggc tgaggcatga gaatcacttg aacccggagg   31620
tggaggttgc agtgagccaa gatcatgcca ctgcacgccc gcctgggcaa cagagtgaga   31680
ctttgcctca aataaataaa taaataaaac gtatatggaa atgcaaagga cctagaacat   31740
ccaaagtaaa cttgaaagag aacaaaatta aggggcttat gtgatgtgac tttatagtca   31800
tttgattttt aacagaggca ccagaacagt ccggtgcggg aaaggaaagt cttttagcac   31860
gtgccggatg atggcaaatg acatccatac cagacaaaaa tgaaccttga ccttacccta   31920
```

```
aatattagtt tcttagagtt gccacaaact aggtggctta aaaccacaga aatttggctg   31980
ggtgcggtgg ctgacgcctg taatcccggc ctttgggagg ccgagtcggg cagatcacct   32040
gaggtcagga gtgcaagact agcctggcca acgtggtgaa actttgtctc tactaaaaat   32100
acaaaaaact tagtcaggtg tagtggtgca cacatataat cccagctagc caggaggctg   32160
aggcaggaga attgcatgaa cctgggaggt tgcactgagc caagattgca ccactgcact   32220
ccagcctggg tgacagagtg agactccgtc tcaaaacaaa accacagaaa tttgctgtct   32280
cataattcca gagtctagaa gtccaaaatc aactgtcatc agggccatgg tctctgtgaa   32340
acctgtaggg gagtccttcc ttgcctcttc ctagcttcca gtggttggca acctttggca   32400
ttctttgatt tgcagctgca ttacttcaat atctgtcttc ctcatcacac agcattctcc   32460
atgtatgtct ctgtctttac atggcctcct tcttgtaaga acaacagtaa tattggattg   32520
gggcctgccc tactccagtg tgacctcacc ttaactaatt acacctgcaa caacgctgtt   32580
tccaactaag gtctcagtgt gaggtactga gggttaggac ttcaacatat ctttttggg    32640 ggacatagtc caacccatga cactacttca caccatacat aaaaattaat tcatgagaga   32700
ttatagacct aaatgtttta aaagctaaaa atataaagct tctgcaagaa acataggag    32760 aatatctgtg cagtccaaag aataaggttt tttttaaaca caatttcact ctgttgccca   32820
ggctggagtg cagtggtgcg atctcagctc actgcaacct ctgcctcccg agttcaagcg   32880
attcccatgc ctcagccttc caagtagctg ggattacagg tgtgcgccac catgcctggc   32940 taattttgt attttagta gaggcagggt tttgccatgt tggccaggct ggtctcaaac     33000
tcctgacctc aagtgatctg cctgcctcgg cctcccaaag tgctgggatt acaggtatga   33060
gccaccgtgc caggccaaaa aaagatttat taggatacat gaagcaatag ctattaaaag   33120
aaaaaataaa ttggacttca ttaaaattta aaactttgg tcctcaaaag ataccattaa    33180
gaaaatgaaa agacagagct gggcgtggtg aggcttgcct gtagtcacta ctgggtactt   33240
gagaggctga ggcaggagga tcacttgagc ccaggagttc taggccaaca taggcaatat   33300
agtgagacag tgtctcttaa aaaaaaaaag aaaaagaaaa aacaaaagaa aataggctga   33360
gagctgtggc tcatgcttgt aatcccagca ctttgggagt acaaggcaga tggattgctt   33420
gagctcagga gttcaagacc agcctgggca acagtgaaat cccatctcta caaaagatac   33480
aaaaaattag ccaaccatgg tggcgtgcac ccgtagtcca tagtcccagc tactcggaa    33540 gcagaggcag gaggattgct tgatcccaag gaggtcaagg ctgcagtgag ctgaggtcgc   33600
gccaccgcac cccagcctgg gtgactgagt gagaccctgt ctcaaagaaa atgaaaagac   33660
aagtccacca agaaaacagt tgagaccagt catagaaaaa atagaaagtc atatctgaca   33720
aaggatttgt attcagaaga attcctataa ctcggtaata aaaagacaac ctgattttta   33780
aagggtgaaa atatttaat ggatactttt tttttttttt ttgagacaga gtctcactgt    33840
gtcacctagg ctggagtgca gtggtgccat catacatagc tcactgcaga ctcgaactcc   33900
tgggctcaag tggtcttcct gcctcagcct cctgcgtagc taggactaca agcacgtgcc   33960
actatgcctg gctaattttt aaattttttg tagacatggg ctggtgtgtg tctgtgttgt   34020
ctaggctggt cttgaactcc tgggctcaag tgatcctccc acctctgccc cccaaagtgc   34080
tgggccacca cgcctggtgt ggtgtcacca gagatgagcc accatgccct gcctgatact   34140
tttcttttat catctgttta tttcttgttt atgggtgttt ctgttctgat tttatgacta   34200
ttctgtattc taagatttct ctgagaatat tatttgtttc ctctaaggac agacttggtc   34260
```

```
tctcttccat ggggctggtt cttgagccgc cagggatggg gggaggacct gggtagctgc   34320
tgcgctgccc cttctctgct gtggtggagt ggcccgttgc ctgcgggtc tgtctctgaa    34380 gggtggtttg gagaagttct gtggaggcga ggcagggtc agctcttgcc ccatggaccc    34440
tcagagactg ggaaaaggta ggcatcacct gggctgctgc cagccacatc aagagccttt   34500
ggggtgggtg gggtgggggc cggggaaggg aaggttctag ctgttgattt agaaaagacc   34560
cattgatttc ttgcctgagg gaagaagtgg caccttgcca ctccaagttt gctctgctca   34620
ccagccccaa cagcatcagc ctcacctggg agcttattga aggtgccctg ccccaaagct   34680
tgtgggtcgg gatctggcag tcagcagccc ccaggtgttg cacacatgac agcactgctt   34740
gcccctcctc tcgtctggtc tggtctggtc tggtctggtc tggtctgaga gcttctttgg   34800
ggctctgaca ggtatacagg ctctcatctg ctctacagct ctcttgtagt acattcctct   34860
ctgttccatt agtcaacatg ttcttgccta cttccagcat ctagaaattt gctgagtgta   34920
tcttatccgt tcagaggtcc tctcctgcta ttgcctctgt tagaaatttc ttcccttttca  34980 tatgtctgta cttcggtttc tttgaggttt gaagggtcaa gtggcaatta catgtaggca   35040
gttggccatc ctctggtgaa ggctttaaag cccaggaata caagatcca ttatgtctaa    35100 aactagcaaa aaccctacct gtcacatggt gaactgaatt agaggtgatg gggacagaag   35160
ccagattgga gtgagtggaa ggtgagggag tggagattgg gtatagacaa ctctctttaa   35220
gaagttttgt tgtgatggtg accagaaaaa taggagtggg gtagaggggg atgagggtgt   35280
ttttcacgtg ggtgaatatg agagcatgtt tacatccttc tgggaatggc ccaggagaga   35340
ggggagcgtg agaaggagga aatggggacc tggaggagca gactccttgt gtggaggggg   35400
gaagcggcat ctagagctgt tgcaggaggt gggctttgag taaatgcttc ctctttggta   35460
aagacgggga acgggaacgg tagaagttgc acggacccctt tgttaaagct cagaagctga   35520
gcgagaatta gagcttaagt ttatggagta gtcagaataa agtaccccta actgtattct   35580
tgcacagtgc aggaagccag gggtctgaaa tcaagatgtt gcagggctcc attcccccca   35640
gagcctctag catggatcct tccttgcctc ttccagcttt tggtggctgc ctggcagtcc   35700
tagactttcc ttggcttgca gttgcattgc tccattctct gcttgtgtct tcacatggcc   35760
ttctctgtgt ccccgtattc ttctctggat gcttgtcact gtattaggcc caccctaaat   35820
ccaggatgat ctcatatcaa gatccttcac ttaattacag aagcaaagac cttccaaata   35880
aggtcagagc cacagggtct gggggttaag acatacacct aactattcgg ggctaccatc   35940 gaaccctgt agaagcctgt ccatttccag gatagcagag cccaaggaag ggccagaagt    36000 cccccccaaaa cagttgtttg cattcaccag attctaagct ataagcagat gggcagtggc   36060
agtcggtcct aatccatata ccattggcaa caatagttta gttcactgta gacataatga   36120
gatgcttatc ttctgctaag tagtcctcat ggtaacagcc atattactcc tggctttgag   36180
tgacagcgct gtgctcttgt ctggtgccca tatacttcag cagctggaaa caagacagtg   36240
ctcatgattc accggaaagt ttctgtagtt aaaatcaagt gatcccttga gtctattcta   36300
atatttgtct gtaccatgtt ctgtgacgag acatggaaac aaaacattaa gaagtgaaag   36360
tatctttgat tatgctcttg aagacaactt tttgtttgtt tgttttgttt gagacggagt   36420
ttcactcttg ttgcccaggc tggagtgcaa tggtgtgatc tcggctcact gcaacctccg   36480
cattcccggg ttcaagcgat tctcctgcct cagcctccca agtagccagg attacaggca   36540
tgcaccacca cgcctggcta attttttttta ttttagtaga cgggggtttt caccatgcta   36600
gtcagactgg tctcaaactc ctgacctcag gtgatccgcc tgcctctgcc tcccaaagtg   36660
```

```
ccgggattac aggtgtgagc caccgtgcct ggccgaagac aacttttttaa agatgcatat   36720
gctctgggct gggtgtggtg gctcacacct gtaatcccag cactttggga ggccaaggcg   36780
ggcagatcac ctgaggtcag gggttcaaga ccagcctggc caacatggtg aaacaccgtc   36840
tctactaaaa gtataaaaat tagccgggtg tggtggcggg tgcctgtaat cacagctact   36900
caggaggctg aggcaggaga atcgcttgaa ccccagaggc ggaggttgca gtgaattgag   36960
actgtgccac tgcactccag cctgggcgac agagtgagac ttggtctcaa taaataaaat   37020
aaaataaaga tgcatatatg ctctgaaggc tggctacatt ttattttttc tcaaacaact   37080
tttacagtgg atagtgctgt aaaagttgtt tagctctggt cattttatct ttttgtgat   37140
ctgcaaaagg agatcctttt cctttttcact gcctctaata cccaactcca atactccttt   37200
gacctcacag gcacttagaa tccatcagtg gctccatctt ttctcagact tcacctcctt   37260
cgtatcctta ttcctctcct tgtagcttc agtgccagtc agacgtcgtt actccctggc   37320
acactacctc agcccttcgg cacttttcttg ctttgttata ttcagtcgac aaagccccag   37380
cctcatgaaa ttcagtcatg tctgccccat gcctgctccg tcctgaagct gaatgtgact   37440
ccttcattga ttccccctttt aagttcatgt ctacccagg taaacttctt gccgccaagc   37500
ccacctgcat actgcagttc cccggtctct cctagcccct cccaccctcc tcatcagctg   37560
tcacacctcc ttgcagctga tatcttagtt cccagagagc acagaagcaa gctcaagaga   37620
gtgtctacag gccagcgtct actccttcgc tctgcctccc tcatgctgtc acggagcgcc   37680
tgtcccaggc cctcactcct gttctaaggc atctctccag tcctctactg cactctcccc   37740
catcagagat tcctccctcg cctgccctag aaacttgttg ctacttctcc caccttgaca   37800
aaagctgctc ccaaccccccc acctgtctag catctctgtt ttcctttacc agcaagactc   37860
cagtccctgt ctccacaccc tcttcaacct tctccagttg ttccttttgct gccacagctc   37920
tgccaagctg ctccatgagg tctccagtga tgaccttcat gttgttaaat ctgggagctg   37980
cttgtcactt ctttttcccag agctgtcgtc gtcagttaac cccaatacccc atacgagaca   38040
atcctttccc tcccttgagt ctctgcactg atgtgcacct tctcagtgca aaccacagct   38100
tttgtctctt tctagctgaa tacatgactg actgtgctta tcttagctgt caccctgct   38160
ggagcagaag ctccacagga caggattgtc tccttgattc acagatgtag ctcaagctcc   38220
tagaacagtg cctggtgtct gtgggtcctc aggaagtcct aggtgagtgt gtgaatgtct   38280
gtcctcctcg gtcttttctg tttcgcatgt gatgttggaa ggcctcaggt tcaggctttt   38340
cttctccacc ctcactcccg aagtgattcc gtccagcctc atggctccca aatttatgtc   38400
tccaggctga ctgggtcacg ggaactcctt atcctcccta gaccttctct ttccctggtc   38460
ttctcctttc cagtaaacag caactccaac tcctgctcct caggccagaa acctggcgct   38520
ggttacctca tttgttcaca aatactgtta ctccacctgc aagatggata caaaatctca   38580
tgagttcccc tgcctccatg gccccacccc tggtccaggt gtccagcttc cctgcctctg   38640
cccttgcccc ctggttcttt gtttagtcct gcaatattgt gctcttctgt tcagaaccct   38700
ccagtgggtc cctgcttgct cagagtcaca gcccaacagg atcacctctc ttgccactct   38760
cccaccactc atgcactgcg gcctcactgg cctcctggct cctccctgga cctccaagt   38820
atgcccctgc ctcaaggcct tgacctctcc tctgccctct gtcccaggta tcacacatgt   38880
ctgctcaagt gtcaccttcc caatgtggcc ttccccgagc acaccatgt ctgtaagtca   38940
ggcagcctgc ctctgcccca ccagttcccc ctgcctagca taggacttgt caccatctgc   39000
```

```
cacaagctgt gttactgctt ggttttgttt gtgctctccc actcccttcc cctccctccc    39060
tctccccacc cctatagaat ctgagtccca tgaggacaga gatttttttt tttgcctctt    39120
cctcaatata tccccagtgc ctagaatcat gcatatttta atttattgag tgaattaaca    39180
aataaattct gcagtgggac attgctctaa ggttttgtct tataagaggg acagaagaac    39240
atgcagcctg ctctgctgtt ggctccttag cttctccatg gctaacagga acaatattgt    39300
ttatgagata atcaaagcca tagtcatgag ttagaaggta catataaagg caaatatgtg    39360
gagattgagt tactttggcg ggggcggagg ggtgtgtagt tatctgaaaa catggaacaa    39420
atcaatgaga gtctaaatag cacccacata tttgcccctc ttttaaaaca tacctccttt    39480
atgagtgtag aatttaacag cacagtttcc cagtgcagct ttgcgaaaca agagaaatga    39540
atttttaaagg ctgtcaggtg cctttgcaat ctgtggctta gtatttgtgt aacaacattt    39600
gtgttttgcc aacagatgta ctgcttaaag tacccatgag aatggcctct gtggttttct    39660
actttctcgg atggaacctt aggaactgat tattgagaag aggctgatac tgcccacctc    39720
agctcccagg caggcttcag ggccttggtt actactcctt tgggccctca ctgacccttg    39780
cagacgtctt ttgcaacctc tgtagccaga agagacaact gctttctggc atgttgctct    39840
ttccctaatg gctttatgag cttcttgaac accaaagcat gtgtgacttc ctcacgcctt    39900
cccctgtata gtatagcacc cctaactgta tgtgtaagga gaaggagtga gcaattgatg    39960
gcgtccccct ggatctccaa gggaatggga aggggcaggg tttctggatt cagtcatgtg    40020
gaatctggtc gttggtgtct aaatgtgcct gttacttgtg cccaatgtcc aggttcacca    40080
ggaggcttag cctgctcatt tccctgctag tagctatatt ttgggagagc atttttttatg   40140
ctctaattga actttgtggg tctcagcaat ttgaacaatg ttttgttttt cttctggtca    40200
ggttacaaag gaaagaaaag gaatctggtg ttgtaggagg tggtgtgttg tgtaattact    40260
tgttttttt ttttaagttt ttttatattt ttgcaacaag gcaagttttc tttgaataaa    40320
taatgctggg agcttatcac atagaaggca tatgtgttgt actcagtaca ttctgaatta    40380
tctgggttta ttttttatctc ttgaattcac ttataaacaa ttcaaaggct gctttttttag  40440
ctaacagaaa taggaagaga atctcagaat ctgttttgtc atttttttcaa tgggttgagt   40500
tatagtgatt atgctaactc ggtggaaaag cagtgtagtg agtaaacccc acatacggca    40560
tatcatgaac atttttgttgc ttttttggct tctgaccatc ttcatacctt ttttttgtgtt  40620
aaaagtctcc ccattgtgta tatcttagta agaggcaggt ggaccctagt ttctacctaa    40680
gaaaacctga agatgggtt gggggcctgt ggtgtacttc cttctcatgc tgtccatgac    40740
cactgcagtg gctttgtaag gatccaggac ccagggcccc tcagtgggtg tcttccatt   40800
ctcaagattg cctcttggtt gtgagatgac ggttgctgct ctagtcattg catccactcc    40860
tccaggtagg aagaaagagg tcatagggga aaggcaaaat ggcacttgac atcttaactt    40920
ctaggcccat tcaatatttc catttccatc ttcacaccca tcatcttgtc ctagggaaca    40980
aacagcacca gcagctcagt agctataaca gcaattatta tttctcacac atgggtctgg    41040
gtcagctgca agatgggatt cagatctgtt ctcaagcctg tcgttccagg acccaggagg    41100
gagaagcagc tgccagggga agtctcttcg taggcggagg tcaggagtcc aagaggagtg    41160
agcagagtca cagaagcctc ttaaagcctc ttcttccccc atcccatcaa cacgtgagca    41220
agcccagagt cagtgggtgg gaggtgtgct ccgcccatag tcagtagaac aagagcaagc    41280
ttgaaagaga acgatgaaca ggagtgcact cggccactgt ctccttagcc ataacgtagt    41340
cccatggtct gctgggaagc ggggaataac tctccttagc tgagcgcagg gtctcattag    41400
```

```
taaggcagat ggagaacatg gatgttgggg gacaactggc agtgcctgcc acagggaat    41460 ggatatattc cctcccctcg ctctctggaa actaggggag ggcgatgaag cctaggtttg    41520
gccaaaccca ttctgccttc agggactttg actcttgagg gacagtgagg gattagtcat    41580
ggtggtggca gttgagtcac aaaaccagca gtggtggcta atgtccagtg atgacatgca    41640
acagtgccca gggtgggtgt cccaaccagc aggtccctgc agtataacct tggctgtgtt    41700
tgcagtggtg cagcctctat tcctgctgct tttctgagcc tagttctcta gttctctctc    41760
catttccaga tctgctgccc aagaactcct ttgtgattga atttaaccag agttgatttc    41820
tgttgcttga aactcaggac cttgatgcag tgtgcagggt ctgggcaagg taaaaacaca    41880 cttctcatgat ttcgcctcaa gtatagtaga tgagcttagg cttttgtagc caggtagcct    41940
tgggattaat tctcagctct tgcacctagc aggtgacctc agcaatcaag tcacttgccc    42000
tccttgagcc tcagtgttgc cctcagttaa acattgctct cgtgtgttgc tgagcattca    42060
gtgagattgt atataaagtg atcattgtga aggtattggg acataatttg ggaaagcgtc    42120
ctggtctaag cttttgattg gctctccatc atttgggtaa tgggatagtg atttaggagt    42180
atcatagcag ctcaagggc ccttctggaa agggtatgag gaaggtcagg acaagtctg    42240 aaatgaatca tcctaggctt aatgcctgtg actgggcagt gggtacaatt atctcaggct    42300
agtcagtagt catttattgt gagaatacat gggcagattt tttaatttcc ttctcagtct    42360
agacttgaat gcaaacagtt cttattgcta acttaccact agtcaccact aatgaacaaa    42420
gactatgaac aggaaattca taaaagaaga gatacagatg gccaatgaag ataggaaaag    42480
agttctgcct gctggtaatc aaagagatgc aaacgagaac aaaaatgatg ccttttcacc    42540
taccaaattt gtcaagatta aaagaaaagc aaagagccag cgtcagctga tgttcatacc    42600
tgcacctgct cggtagcttg ctaatgttct gcctgctcca cacgccaggc cagcctccac    42660
ggcgcagcca ggtgaggcct ttccttgtat acaggcacgt ttggattcac tgttgcataa    42720
gtgagacatg tgcatgcttc acaattcagg aagtgcaaac tccagagtga tgcaaggtct    42780
gagtgtccct gctgccctgg tctcccagct gcctaggcct ctcttcaggg aacggctgca    42840
tccagggtct tgtctgtgtc ttttgaggtg ttctatgtac acgcagacac atctaaacct    42900
atttttattt tccctgcacc tgcttgggct actgtaagct gttaaatttt tttttctagg    42960
aatttgtcca ttttgtctga ctagcataaa gttgttcatg ttatagttta tacatttgca    43020
acatctgtaa ttatgtctgc ttttcattc ctagtgtttg ttgtttactt gtaccttctc    43080
ccgtttttcc ttgtcttggt aaaagctcat taggttcatt ggtcttacaa gaagcagaca    43140
tgtaggcatt attgccctgt attactctgt gtctcttttc tagttcatta aattctgctt    43200
ttgcttttat ctttattatt ttttctatgg tcttagagta cattctctgt gttttgttgt    43260
tgttgttgtt gttgtttgtt ttttgttttg agagagagag tcttgctctg tcgcccaggc    43320
tggagtgcag tagtgcaatc tcagctcact gcaacctcca cctcctgggt tcaagtgatt    43380
ctcgtgcctc aacctcccga gtagctgaga tttacaggca tttgcccccac acccggcaaa    43440 ttttttgtat ttttagtaga gatggggttt tggcatgttg accaggcggg tctcgaactg    43500
ctgacgccag gtgctccacc cgccttggcc tcccaaagtg ctgggattac aggcatgagc    43560
caccacgcct ggccctaact tcttaagtta taaatttggt tcattgattt ttctacccctt    43620 tttcaaatg taaacatttc aggctaaccc tctggaacta cttcaactgt atctagcaag    43680
ttctgatagt attgtcactt taagttagcc caaagatatt ttaaatttct tttgtttctt    43740
```

```
cctttgactc acatattatt ttaaaatgtg tttttcaatt tccaagcaca tggctttggg   43800
tttgttttt tttttttccta gttgctctag aaaaaaaaat tgactgcatg aggtggctca   43860
tgcctgtaat cccagcactt tgggaggccg aggcgggcag atcacctgag gtcaggagtt   43920
cgagaccagc ctggccaaca tgccaaaacc tcgtctctac taaaaataca aaattagccg   43980
ggcatggtgg cacacacctg tagttccagc tactcgggag gctgaggcag gagaatcact   44040
tgaaccggga ggcagtggtc acagtgagcc aagattgtgc cagtgtactc cagcctgggc   44100
aacaagagca atactccgtc tcaaaaaaaa aaagaaaaa aagaaaaaat caacttctaa   44160
ctaaatggca ctgtgatcaa agaacttggt ctgtgtgaca ccagttcttg cagttggttg   44220
agaagtgctc catgacacat tatccacaac cagtggacag aatatgtcac caccaagcat   44280
gggtgcagga ttctacatat attcattacc tctgtcttat ccgtttgttg tgaaagtatt   44340
ttctcttctt actgtcattt tgtttacttg atttatcaac tgatggaata cgtgttaaaa   44400
cctactgtgg tgatggacac atcagtttct ccacagagtt tggtcatttt catttatta    44460
tttattttga ggccacattt tcagttttag atacagtttc acattcctgg tgtattgaac   44520
cctttggtat tatgaagcga ccatactaat atgttatttt tttttaaatt attatttatt   44580
ttatttattt ttctttcttt tttttttttt tgagacaggg tctccctctg tcacccagtc   44640
tggagtgcag tggtgcaatc tcagctcact gcaacctccg cctcctgggc tcaagtggtc   44700
ctcccacctc agcctcctga gtagctggga ttacaggctt gcaccagcgc gcctggctaa   44760
gttttttgtat ttttagtaga cagggtttt tgccatgttg cccagactgg tctcaaactc   44820
ctgggctcaa gcagttcacc agccttggcc tctaaaagtg ttgggattac aggtgtgagc   44880
caccacgccc ggccatccca gttttttatt ttcctccttt ctgtgtcttt atgcatcagt   44940
gaggtggagc ttttgaaaat gtcagatagc tagattttt tttttttgaga cggagttttg   45000
ctcttgttgc ccaggctgga gtgcaatggc gtgatctcgg ctcactgcaa cctccacctc   45060
ccaggttcaa acaattctc ctgccgcagc ctcctgagta gctgggacta caggcacgtg   45120
ccaccacacc cggctaattt tgtatttta gtagagatgt ggtttcacca tgttggccag   45180
gctggtctca aactcctcac ctcagctgat caccccgcctc agcctcccaa agtgttggaa   45240
ttacagacgt gagccaccat gcccagctga tagctagatt tttttttttt tttttttttt   45300
gagacggagt cttgctctgt cgcccaggct ggagtgcggt ggcgcgatct cggctcactg   45360
caagctccgc ccccgggtt catgccattc tcctgcttca gcctccagag tagctgggac   45420
tacaggtgcc cgccaccacg cgtggctgat tttttttt tttttttttt tgtattttta   45480
gtagagacgg ggtttcaccg tgtcagccag gatggtctcg atctcctgac ctcgtgatcc   45540
gcccgcctca gcctcccaaa gtgctgggat tacaggcgtg agccaccgca cccggcctcg   45600
agattttta aaaaatccat tgtctgtttc gtcctttaac atctatttga tttctgatgt   45660
atttagattc atttatagca tatttgtgca ttctatttt ccatatttc tgttctttta    45720
aattttcctt ctcctttctt gccttctctt agactttta aaaaattgta gtaaaataca   45780
catcacctaa aatttaccat ttttaaatgt acagttcagt ggcattaaat acaaattgga   45840
ggccaggcat ggtggctcat gcctggaatc ccagcacttt gagaggctga ggtgggagga   45900
ttgcttgaac ctggaggtcg aggttgcagt gaggtgtgat cacactactg ctatagccca   45960
ggcaacagag tgagaaccta tctaaaaaaa caaacaaaca aacaaacaaa cagattggca   46020
tcacacagtg tgtgtgctgc tgtgctgtgc tgttatcatt taacattaaa acataaacat   46080
cagcactgtt atggactgaa tgtttgtgtc ccccaaaatt ccagtgttga agctcaaacc   46140
```

```
tccaatgtga tgttatttgg agatggggta tttgagaggt ggttaggttt agatgaaatc    46200
aggagggagg gtgggtttcg catgatgaga ttagtgtcct tataacaaga gacagcagag    46260
agcttgcttt ctccaccatg tgagtatgca atgagaaggc agccatctcc aagtcagaaa    46320
gagagccctc accaggggct gaatgtgctg acaccttgat cttggacttc tagcctccag    46380
aactgtgaga aatttcagtt gaataggccc cccagtctgt actattttgt tatagcttga    46440
gcagactaat acaccatgt tatgaaaagc tataaacatc cctttaaagg ccacctaacg     46500
cgtcgtatta cctcatgcat cttctctgct gagctttcca aaagagtggc ttaggctggg    46560
cctggtggct catgcctgta atcccagcac tttgggaggc caaggcaggt ggatcacctg    46620
aggtcaggag ttcaagacca gcctgaccaa catggagaaa tcccgtccct actaaaaata    46680
caaaattagc tgggcgtggt ggcgcatgcc tgtaatccca gctacttggg aggctgagcc    46740
aggagaatca cttgaacctg ggagatggag ggtgcagtga gccgagatcg tgccattgca    46800
ttccagcccg gccaacaaga gcgaaactcc atctcaaaaa aaaagagtgg ctggccgggc    46860
gcagtggctc acgcctgtaa tccccgcact gtgggaggcc gaggtgggtg gatcacgagg    46920
tcaggagttc aaaaccagcc tggccgagat ggtgaaaccc cgtctctact aaaaatagaa    46980
aaactagcca ggcgcagtgg caggcgcctg taatcccagc acttgggtg gctgaggcag     47040 gagaatcgct tgaacctggg gggcggaggt tgcagtgagc caagatggtg ccactgcact    47100
ccagcctggg tgacacagtg agaccccgtc tcaaaaaaaa aaaaaaaaa aaaaaagtg      47160 gcgtatgttc ccggtctcca cctctcattc gccagcccct gtgaccaaac ccctgggatt    47220
agatctccat cgggtccctc ccctcaccct aacctcacat gcagtggttc ctgagaagct    47280
gctgtttatc tgatcacggg atccagcagg atctgagggc tcattcactg aatctgtact    47340
acccaacaag gcaggcttgt ccttacccac acttttcagg tgaaaactta atcagattca    47400
agcgtttatc ttagtggcct cttcgtggtg tgtgatttcc ttcttgcagc tctttactgg    47460
ctaaaactct tcactgggag ttaaaccagg tgtggtcctt gaccctcatc attttgtccc    47520
atctcctatg ctgggctctg tatccttgtc tccaagcagt ctcgtgtgac agggaagtta    47580
cctattattg tatggtcccc tcttcttgtc acctctggtg tggcacttgt tccatttctt    47640
gttcaatgaa tgtgatttgt gaatgtgcca catctgtggg aggaaggcag ttcgcagcaa    47700
gagttgtagt tcccttgctt tgccctgagg gccaggactt tacactagat ttttttgttg    47760
cattcctgca ctcataaagt acacgtaaac ttagaggtgg tgtgttaaat gctagaactt    47820
aaaactgagt tcagctaggc tcaagtgccc cacaattttt gtcccaccag acaatttcat    47880
gaatatctac agattgttcc ctcaatatgc ctcaatattg aggcatattg atttggggag    47940
cacagacaag tcaaggttga tgtgcatccg ctgaacatga tcttaagttg ttgaagtagg    48000
tattattaat gaacgaacgt ctattttagc tccaagagcc cctggtcttc cagaagagac    48060
tcccaatgat cttccagaag cagctgggct tcttttggtc ctcccccacc caggtgcagt    48120
cccgttctcc ctgcctgggt gagtttgatt cctctgccgt ggaataggct aggctgctac    48180
ctcttgagcc tcttccacca ggccatccat taggtggcga cagagagcac taaaaggaac    48240
tactatggaa ataaaacttg ttttgcttct tgggggaaa aaaaagaaa aaggcttgtg     48300 gggcgtgtgt gcattttagt cagatttac tgtgcaaaac atttgagaga tttctgccct     48360
ctttctccct tccattcttc tcaacccact gggcgcccta ccacccctgt ctccttcaag    48420
ataaggtaga tcagaagacc aaatagacaa atgccatgtc cactgttttc tgtcacagtt    48480
```

```
gatagccata ccagtcaccc aagctggaaa cccaacaggc ccctgccctt cactgcccac    48540
atccaaggga gccaccaagt cccacaaatt gttcctttaa ctgtttgtcc ctcttttgtc    48600
ttctgtcatc ccttctaccg ctgtcctggt tcaatccctc atcttgctct gggactccca    48660
tgataactta tgatctttcc tccacctctc tatcttccac acaatcccta tcatcaatct    48720
cattcccctg ctttaaaccc aagagtggca ccctgtgttt gagtgacatc agggcccctc    48780
atgtggctcc tgcttctctt tgtggcccct tctgttgctg ctgcttttct tatggacata    48840
gccctcagca gtccaggact gcttgtagtt cctcccaggt accatgtttc ttgcactcct    48900
ggcctttgtc attggctccc ctgcccaagt ccccttctct tctcctttcc ttccctgtg     48960 gccttgcctt gtcgtgctta tccttgaaga ccctgtcagg tatctcttcc ccaaagagcc    49020
ctgcctaacc accgccccc tccccccgc gacacacaca cctgggttag gccctgcctc      49080
tccacgcctg tgcctcctgc caagtcctca gaggtctctg atcccatgtg cctccaggca    49140 tggcatagg ggactgtgac acagcctctc ggcccacaga ccctgattg tgggcttgct      49200 cactgcccca gtcagtcctc ttattgagga ttccgtgcca gttcctgact ccagcacaca    49260
cacgcatgta ggccgccctc ctagtgcctg gctccttccc tgtctcttct gccactcatt    49320
cccatggtcg tatcctggag ttggtcatct ctggaactcc acccacggag ttctaactta    49380
gctctgccta tgatgaggac ttactgtctt cccagcttgc agtgtcaacc actgtttgat    49440
gcccctggga ctccattggt cttccctcct cttgtgaact gtgcccatca ccagacgaac    49500 ttgtttaga atttaccatc gtaactgagc tcccttcagc gcatacctcc ttggctcctg     49560
ctcagtctct gtttctcctt ttagccaaac tctctaagag ttctctccac tcatgggccc    49620
tcttccttgc ctgctgctcc ttgctcagct tgctccatga acacttgctt ttccacattc    49680
catgaaataa tcttaacagt catcagtggc tgtcactcct tctcagccct ttccttgtgt    49740
ctcttctggt acctcatact ctccaggtgg ccatctcacc tcacatcttg aaccctctgg    49800
gtttgggaga attctcacct cacgagttga tgggaggcct ggcgacctct gattgtagtc    49860
actgcaaatg ccagatgctt atttgcctag cttccctttc ggtcagggca gcagttggca    49920
aacggtatct caagggccaa gtccggccca ctgcctgttt tcgtaaatga agctttacca    49980
ggacccagtt ccaccccgtc cttgtgcat tgtccaagac tgctctcctg tacaacagca     50040
ggtgggctgg ttgtgacaga tactgtctgg cccacaaggt ggaaaatact atctggcccc    50100
ttacagaaag aaattacctg agttctacac gagggtgtag gtatgtaccc tggcctctgc    50160
cagtcagact cacatgctag gaggagcagg gccaggcagg agagccgtgt ctcctggcat    50220
tggggctgca ggaaagacga gctcctaggc cacagtgcca gtggccagtg ctgctgcctt    50280
gcagggtcgc acaggcagtg ctggctgttt ggactggctt ggcagaagga tttgaagtat    50340
tgttcctagc caactggact caaacctgtt cctccaaccc tctagggatt ctcttatcac    50400
ccagtagcct tttcccccta gttttaaaaa ttgcagtaaa atacacaaaa gataaaatgt    50460
actgccttaa ccatttttaa gtgtacaatt ctgtggtatt gagcacattt atattgtgca    50520
accatcacca catgcatctt caatagcttt tcatcagtcc ttgtctgcat aaatcagcta    50580
gagttggttt ctattgattg ccaccaataa tcttgacaga tatgtctgat cttccttctc    50640
tgcactgact cctctttctc tgtctcctct gctgattctt tctcctcatc acaactccaa    50700
atagcagggg gagggttgtt tacacttata ttcagcacgc cctcacgcac tcgcctggct    50760
cttcagacct ctcccctgaa ctccagattc atacatccag ctgcccttta ggcctctaga    50820
aagctaaata cctcagtatc aaaaacatga gaaacggaag ccagagtcct ggatctctcg    50880
```

```
cccttttcgct gtcccggtgc ccatgccctt cagggatggc acctagacca gctccctgca   50940
tccctgccta gactctgcag tagtctcacg tggcagaccc ggaggtcact ctcctctctg   51000
gatgccctgc ggacactccg gttagcctca gctgcaagag cctcctcacc caaggtcacg   51060
ccatttccag gacagcaccc tggtgactga gcgaggtaag ggtacaaggc ccttataggg   51120
ccttctcttt gacttcttcc cacctcccct tatggatgtc agttcctgat gaacatctta   51180
cacctcaaac cgtgacccaa catctgcttc tgcagagccc cctgtggca tcttgtgccc     51240 tcctgcccca ctccctctac tctatatctt cccatagtta aatgggcttt ttttttttt   51300 tttttgagat aaggtctccc tttgtcaccc aggctggaat gcaatggcac agtcacgact   51360
cactgcagcc tcaacctcct gggctcaagc agtcctccca cctcagcctc caagtagct    51420 gagactacag gtatgcacca ccacacctgg ctaattttta tattttttgt agagactggg   51480
gtctccctat gttgcccggg ctggtctcga actcccaggc tcaagcaatc ctcccgcctt   51540
ggcctcccaa aatgcaggat tacaggcgtg taccagtgtg cccagcctca gatgggctct   51600
ttgaaaaatg tttattagat caggttactc ccttgagaaa aaccctctca gaataaaacc   51660
cgaagtccat tacttgaaag cagagccagc ttcatgggcc tttgtaactg cccatgggct   51720
tgctggaacc caggcttggt ttaatactct actctcacca tctcaaaatt cttaattttt   51780
gaacaagagg ccctgcattt tcattttgca ccaggctcca caaattgtgt aactgggcct   51840
gcctcagcag ccacatggaa catgatccct ccttgcctat ttgagctcat tctctaccat   51900
tctctccctt gctcacctgg ctcccactgc tcttgctctt cctggaactt gccataatgt   51960
tgctagagtc agagccttgg ctcttgctgc tcctcattgg ctggacccct ctttacttga   52020
cctgctccct caccactcac ttccttcaga tctgtgttca gatttcgtct tctcagagag   52080
gcttttggcc cctgtccatc tctctgaatt tacctctgac ctctccccca ccaccactgc   52140
gctaagctgc ctcagaactt tgtagacatt ctgtctggtc ttctgatgtt tccccttgg   52200 aagaatccca aggtgcctga agaatgcttt ctttatcctt gaagttgagt aggttgacta   52260
gagtctggct tgctattgag cattctttat caaattgtcc tgggaacatg gtgtattctt   52320
tcagtctgca gatgtagtcg ttgctgtttc aggtcagctc tcttatggat ctttgacagc   52380
atcttctgtt ccattgttg agttctgtac ttcagggaca caaattcctc atgttggatt   52440
gtctttgtct ctcttccaat gctattagct ttgccgtaat tggtttagct tttgtctttt   52500
tcatctgcat tcactttgtc taatttgatt ttcagctatg tatattctgt ttctggctgt   52560
ttttcaatgt atttattagt ttcataatga tgtgttttgg tctgcagttt gtttctctag   52620
gttggaaatt tgtcttttca tcttattctg ttttatcatc ccatctttga actcttttat   52680
tgggaacatg ttcttatgaa gttgtgggga atttttttcc cttccttgtg tattctcttc   52740
ttggtgggag actttgcctt tctcgtgcca tctccctccc tgggcctctt ttttttcttc   52800
tggccataat atgtttgcct agttaccatg tcacttcttt tcgtcttggc tcaggcttgg   52860
atggctctgc atagtcgttc tgtttgcttt gagacagtgg aggaattctt ggctctctct   52920
tcccagtttc ttggcatctt ctcttgctgt tttcccctct gagctatcgc gtgcaggctt   52980
gttatcttgt atccggagag aatttgcacg ctggagggag ctgcagccat gtagtcttca   53040
gccctatctg gattcttctc tttgttctaa gaactgtgtt ggatgtctta ctaaggctca   53100
ctctagctgc acgagggatg tgtgtgcat ttccatgggg ataggggca cctcagtctc     53160 tgggtggttc cataatctgt gtatacctaa gagcagttgc ttcccacaga gctgggctgg   53220
```

```
ctcactgggc actttgccat ttctcctgca cctcccagct ggagtttctg ggtctaaaag   53280
gaaaaagtga aggactccca cttggttgct tctctccagc ttactgactg caaattccca   53340
gggcgttgcc cgctccctag ggtggtttct gggggacggg gcaggagcct ggctttgctg   53400
ctgctttgtc ctctggagtc ttttctcaga ctgctttgaa ttacacccct ttcctttgtg   53460
tgctgaaatc ttcccttcac actctccttc cctgcctttc ttttgtgtct tatcttacta   53520
ggactggaag agggcagttg tgcaggaggt ctgcatctaa ttccctaatc catgtgagag   53580
tgctcctgtt gtgtgctttg tgacatgatg gtgagaaata ctccctagag cagtggctac   53640
cagaaggaag ccatcccccc ccctgcacac acacacacac acacacacac acacacacac   53700
acacacacac actccttctg gctgtcctca gatgcctatt ctaggtaaat gtcagattcc   53760
aaagaaaatc cagttgagat cttttttctt tttttgagac gagagtcttg ctgtgttgcc   53820
caggctggag tgcagtggca caatctcggc tcactgtaac ctccgcctcc tgggttcaag   53880
cgattctcct gcctcagcct cccaagtagc tgggactaca ggcgcgcacc accacaccag   53940
gctaaaattt ttttgtattt ttagtagaga cagggtttca ctgtgttggc caggctggtc   54000
tcgaactcct gacctcgtgt tctgcccgcc tcagcctccc agagtgctgg gattacaggc   54060
ttgagccatc gcgcccggcc tccagttggg atcttgactg gaatgactgg tgttcaatca   54120
ttatagtttc cacctaattt gtatttgtac acaggacagt tactaatttg ttggtacttg   54180
tttgatcccc agtccctaga gttgtttatg gggtggagct tcagtccctg ctgcttcccc   54240
tgtggcagca gctggagtca gggtggggac ccagggtgct gctggcagat tcttgagaca   54300
ggtagaatct cctctatatt ggtgtctctc tctgtcccag cagtgcccag gaaaacctgg   54360
ccagcctgtc actgacctct ccacctaggg cactggtggt tcaggtcctt ctatttgcca   54420
ccggcaaacc gtacttctgc cagtctggct cttaggccca gtttctctga tcttgcagat   54480
tttcttgggc tctgctacgg aatcctcata cctccggcag gtccctcctt tgcccatgtg   54540
tttaactgtg gtggaatcgt gtgagagctg cttctctcgc atggatccca gccacaccac   54600
attctacagc ggttcctctg aaggcattga tagagatatt tcctcctgtt ttgcatttcg   54660
ttggtcattt cagtagaatc agggtgaaat aaacatgggg gctcagatgt cagcattacg   54720
aaccaagtac gtcaggcagg ctgatgtgga ctgacctaca ctagtgagac gcaagatgac   54780
gaaaacaagg gcactcactc caagttactg atgagatgtt tggatcaaat gagccagtcc   54840
ttaagcagag ttctctagta aaagagatct cctttctgcc ctttcttgtt ccccaaaatg   54900
tgttgccttc atggtgaaaa tttatttttgg cagattttct cttctttgat aaaagcagcc   54960
aacactttgt taaagtctg tgaaacttat ttacatgaag tatgtaaagg taagaaaaaa   55020
acattatcaa caagaaatgg agaaagccag cagctgagga cagaaaagtc atgcacagtg   55080
tcagtgtcta tggaaacagg ccacttggac cttgaggact aggtatttgg aattggaggt   55140
gagcttggcc tggtgagtct ctaaccactt gtgtgtagga tcagtgtgag accctgctca   55200
gaatatagtg gcagagatgc aagggaaat cattggagaa gttaccaggg aatgatgagc   55260
taatctgaaa aaaatacatg tttctaagtt gggcgtggta gctcatctgt agtcccagct   55320
acttgagagc ctgaggcagg aggatcgctt gagcccagcc tgggcagcac agcgagaccc   55380
tatctcccta aaaaaaactt tttcgttgtt tagttttggg attttttttt ttcctggtct   55440
tttttccccc ttttttgtgaa taacgggatc tcactatgtt gcccaggcag atctcgaact   55500
cctgggccca agcaatcctc ctgcctctgc cttcctaaga ttacaggtat gagccactgt   55560
gttaagcaaa aaaactttt taaatgaaaa tcatttttta aaagacaggc tttccagggg   55620
```

```
agggtattat tccacttata tgaagtgtca acagtaggca gatttgtgga gacaaataga    55680
ttagtggtta ccaggggctg agaggagtgg gagtggggag caactgctta atgggtaaag    55740
ggttgtcttt ggaactagag agtagtgatg gtcgcatgac attgtgaatg tactaaatgc    55800
tattaatgat aaattttatg ttatgtgtat tttaccacaa ttaaaaaaaa aagatcaaat    55860
gtcctcagaa tagccaacaa ccttccactt ggctaaatgc ctactcatta aacttcttga    55920
actaaattcc tttctgattg tcatggttat tgtgtcctgg gcttcagagt ttcacattca    55980
ggttggcttg gtccagtctg tcatgtatca ctataggtcc ccacattggc ctcttcctca    56040
gacggacagc ccatctatct gccggggctc tgtgccacag ccagatagac ttgctctgag    56100
acagctgtgt gggctctgag cactggccag gcatcacaaa acctatcttt atgatttaga    56160
ataattggtg gtcagctgct gttttaatgt tgttgttttt tttaatttag atataattca    56220
cataccatga aatttactca tttaaagtgt acaattcatt cttcagtata attcataggc    56280
tcacagaaaa aattgtttaa aaataaaatg tgcaattcag tgtctttag tacattcaca    56340 gagttgtgca accatcgcct ctgtgtcatt ccagaacact ttcagcaccc aaaagaaacc    56400
ccagacacag gagcagtcac ctcttattac ccgcagcccc tggcaacaac tcatccactt    56460
cctgtctcta tggatttgcc tattctggac atttcctata aatggaatta tgcactattt    56520
ggccttttgt gtctggcctc tttcactgag cgtaatgtcc tcaaggttca tctgcattgt    56580
agcatgtgtc agaatttctt tccttttga ggctgaatga tattatatcc tatagataat    56640
gaggttttga ttatccaccc atcccttggg aatgcatatt tgggttgccc ccaccatttg    56700
gctgttgtaa actgtgctgc catgaacact ggtgtacgga tatctgtttg gttactggtt    56760
ttggtttttt gtttgtttgt tttggttttt tgagacaagg tcttgctctg tcgcccaggc    56820
tggattacag tggcacgatc tctgctcact gcaacctcca cctcccaggt tcaagcaatt    56880
ctcctgcctc agtctcctga gtagctggga ctacaggtag cactcaccac catgcccggc    56940 taaattttt tgtattttta gtagagacaa ggtttcgcca tattggccag gctggtctca    57000
aactcctgac ctcaggtgat ccacccacct cagcctccca aagtgctggg attacagacg    57060
tgagccaccg cacccggcat agttgtggct ttttgagagt gtatggctag gagtaaaatt    57120
gccaggtcat atggtaactc catgtttaac atttgagaaa ctgccaaact gttctccaca    57180
gcaggaattt tttaacctgt atgtggtggg cttgtgtttc ggttttcatt ttacacatct    57240
ataaagatga gatttgctgt atggcactgg ttgcctgtat ttggggaggg ttctgctttt    57300
ggttggcaag aactgcattt tatttaagct tagcaaaaca taactggttt ctcgcatctt    57360
ctcaaaagtg gaggattaag aaatggactg cgaattcaga gcagggcagc tgaacctcag    57420
gctccaccct tgtagccttc aagctgaacc tcattctctc ttgctccctg gagaccactg    57480
agacactctg cctgtgccag tttgatttct cacatttta aagggccaaa gcttgtgtct    57540
caaagtgcta tagcctttat tgattcatgc agagaagcct ccttgattcc gtaattctgc    57600
agctaatact ggaagtagaa agaattggaa acaccatctg gatgacactt tagggtggaa    57660
gcagccagta caaggggggg ctcattattt cctctggtcc cagactgttc acctggagct    57720
gtagccacca ccctgccctt aggttaactg cctcgagtgg tagtttagct cttgtgctgt    57780
tgccgaggga taactggaag tgaaggtgc tgagaaatgc catctcctga aagtggcgag    57840
catgagtgaa tttacgaaag gttgggatat tgctggggct ctggaagttt ctctggagct    57900
cactccaggg gacagggagg gggctggatt ccaattcaag tgaaaaatac ctttcatctg    57960
```

```
ccttgttcac ctggctttt tgcctttttg taaaatctga aaacctcagg gattgagtag    58020
tctttcctta actgcagttg cctgtctggc cacacctgcc agctgttgct tgtaccctg    58080
taatttgcac ggccttccgg gcctttctca caagatcact gcaggtcaca ttcatgagga    58140
aaatgcaggc agttcctgcc atcagacccc tcaggatgtc atggtttggc ctgaaaacaa    58200
gattcctgca actctaattt cctttgcta gatcaaatga aggatttgat ctaatgtttg    58260
cattctagca gcaaaatcat tgaatatttt atttcttaag agccttactt catattttgt    58320
aggtatttta agattttgta aaggcctttc tgcttcaacg tgtgatgtgt gcattcttag    58380
aaaaagatct tgtgttctgt aaatcacaca ataaaaacat gagttcgtgc aggaaaaact    58440
ggggcggggt ggatcactcc aaacttgtgt ggtgtggtaa ctggagctca ctgatgaaac    58500
catgaacagt tctggctgaa agaacccccac agtacactga ggtctgttgg catcgccgcc    58560
agcaccgccc cggtcccttt gtgcgcgcca ccacacctgg ctaattttt attttagta    58620
gagaggggt tcaccatgt tggtcaggat ggcctcgaac tgacctcgtg atccgcccac    58680
ctcagcctcc caaagtgctg ggattacagg tgtgagcctc cgtgcccagc cttcagcttt    58740
ttttcttaat gtctttgtgt aatatgaagg cattctcttt aattgttaaa aagcttgcct    58800
accactgctt caaaatatta ctgtcagttg gcatagcttc tgattatatt gatgtcatct    58860
cccttctttt aaacatgtta ccatattggc actgtatttc ccctagccca ttgatcactt    58920
gagagttagt catagtcctc gtgctgtttc actcctaaac gtttaagcat gccttttccta    58980
agagcagaca gtacagttaa gacactcagg aagtttagca atgagctaac acagaaccctt    59040
acatttctcc acatacccca taaatgcctt ttttagagcc tttgagcctg gaatgcagag    59100
tccaggactg tgtgttgtat tcgattgtgt catcccttca gtctcctta tcagaaatgt    59160
tcccccaccc ccttgttttc tctcatcatc ttgagtccag accgtggttg catggcacgc    59220
cctctctgga ctcttcctgc tgtctcctca cggtaagctt cagtctccta ctcgtgatgc    59280
tggttcatct cagcagcact gaggggcctg agctcagttt ggtcgtgtgt taaggtggtg    59340
cctgccagat ttctccacag aaaagggccc cgtacttta tttgctcttc agcctgtgta    59400
ttccttcctt tcttgccagc ttgtgggtgg cttctctagc agcttctgta agatactcag    59460
tttggcagtt gtagttgttt cagcaggaga ggtgtctgca tacctgacca ccacatggct    59520
agaagtcgat ccatcctctg gcgtaaccat cctccatgct actgtccctg ggcactgag    59580
gccctcctca gtgacttcct ccacctcatc ttccgccatc tccaagccac cagtgtccaa    59640
cggactactg atatgtccca aactcatcat ttgtttattc accaattcag agcccaccttt    59700
tttttcagca ctgagctagc ctctccttgc tagaagctta cggtcgaagg tctccagcca    59760
tcagaagaag cacgtggagc gctgcgtccg tgttgtggtt attcatccag catgtgttga    59820
gtaagggttg cacctgtgcc tggcattatg cattgagcgg ggagatgggg gttggcacgc    59880
acagtggggt gttctaagta cactgagggc tcgggtgccc tggctcatag agcagggagg    59940
gaggcaggag cagggaaggt gtctcagaag tgccatctttt ttttttttt ttttgggaag    60000
tggaatcttg ttctatcgcc tggtctggag tgcaatggca ctatctcaac tcactgcagc    60060
ctccgcctcc caggttcaag cgattctcat gcctcagtcc cgagtagct gggaccacag    60120
gcgcacacca ccacacccgg caaatatttt gtattttag tagaggcgga gttttgccat    60180
gttggccagg ctggtcttaa actcctggcc tcaagtgatc tgctcacctc ggcctcctaa    60240
ggtgttggga ttacaggcat gagccactgc gcccggtcta gaagtgccat cctaactgaa    60300
cctgaaagat gaaagttctc cagatgaacc tgaaagttct ccaaatgaaa aggtgggagg    60360
```

```
gggtgacagg gttaggccca gagcctctgg tgacacaggg tgggcatcat tggtcacttt     60420
ttcctcgagg gagggggcgtc acacgggtga tagggtggga gctataacca tgttgatagt     60480
gccgcctctg cccatctggc ctggcatgcc ctgagccctc tgtcccacct gtggaactca     60540
taagccctga cagcccactc actcctgatt cattatccac acccctgtgc ttccgctgtg     60600
cctggagcaa gctttcttca gggggaaggg aggctggaac tatgttgtag ttacctattt     60660
gtcctccctt ccaaactgtg agttcttgga ggtggaagga tgctgcagga tctggctcag     60720
gacgaaggca gttggtgaac agacacgtgt gttttgact cacggtgatc tcagacaagt     60780
tcctctgtct agtcgaactt cttttttcc atctgtaaca ctcaggagtt gaataggtgg     60840
tttttctgag gatacttcaa ctgtaaaatg tatgaacttg tgaactagct atttagttct     60900
cctcataatc aagattgtgt gtgtgtgggg ggttctgatt agaggagga tgaagagagg     60960 tgtatggggt ttttttttgtt ttgttttctg tttgtttgtt tgttttgag atggagtctc     61020 actctgtcac ccaggctgga gtgcagtggc acgatttcgg ttcactgcaa cctctgcctc     61080
ctgggttcaa gtgattctcc tgcctcagcc tcctgagtaa ctgggattac aggcatgcac     61140
caccatgccc agctaattt tgtatttta atagagatgg ggttttcgcc atgttggcca     61200
ggctggtctc gaactcctga cctcaggtga tccacctgcc tcggcctccc aaagtgctgg     61260
gattataggc atgagccacc acacctggca ggtttctttg aaaaagtttg tgtttcggca     61320
aacaccataa acccctgggg ggacagcctt ggggagtcac ctggcaccct agcccagcct     61380
ccctcccttg ggtcctgcag tgaaggctta gtgagggtgt gcaaatgccc aggtcaccct     61440
gggactgggc aggccctctg ggctaagggt aaactcattt ggaatacctg tttctatca     61500 ttgttttta tttgttaaat ttaaagggta caagtgcagt tttgttgcgt ggatatattg     61560
tatagtagtg aagtctgagc tttcagtgta accatcacct gaatagtgga cattgtaccc     61620
gttaagtaat gtctcatccc tcacccctc ccacccttcc cagtctctcc agtgtctgcc     61680
attcctcact ctgtccatgt gcacatgcta ttcagctcct gcttctaagt gagaacgtac     61740
ggtatttgac tttctgtgtc tgagctgtgt cactgaagac aatggactcc agctccatcc     61800 acgttttta tcatttttac ctgcactcca cacccagcac aatccaggct tctttgtggg     61860 tttttgaaa tttgtcttta attataaaag tagcagccag caaattaaca aacacccatg     61920
tgcctttcat tgcacagaat tgaaaatcat catactatat ttgcttcaag taatttccat     61980
tagaaagaac tagaatatta cagtagagtt aaagacccctt tatttcccat cttcagtgct     62040
cttaaaagtt catttagggc caggcatggt ggctcacacc tataatccca gcactttgag     62100
aggcccaggt gggtggatca cctgaggtca ggagttcaag accagcctgg ccaacatggc     62160 gaaacccat ctctactaaa aatacaaaaa ttagctgggc gtggtggtgc gcatctgtaa     62220
tctcagctac tcgggaggct gaggcaggag aatcgcttga actcaggagg gaggcagagc     62280
ctgtatgcag taagccgaga ttgcgccacc acacccagc atgggtgaca gagcaagact     62340
ccgtctcaaa aaaaaaaaa aaaagttca ttcattgtac acttagaaat agttaaaaag     62400
gtaaactttg ttttgtgtgt gtgtgtatat atatatatat atatatatat atatatatat     62460
atatatatgt atttttttt gagacatata tgtgtctggt ttgttcgccc aggcaggagt     62520
gcagtggcat gatcaacggc tcactgcagc ctcaacttcc taggctcaag tgatcctcct     62580
gcctcagcct cccgagtagc taggattaca ggcacacacc accatgccca gctaattttt     62640 tttttttt ttttttttg tagagacagg gttttgctat gttgcccagg ctggtctcaa     62700
```

```
actcctgagc tcaagcgatc cacctgcctc acctcccaaa gtgctgggat tacaagtgta   62760
agccaccaca cctgacctgt tttgtatatt ttaccacaat aaaaagcctt taaaacccca   62820
agcagacagt tcattttcat tcaggcccaa ctcagaatct gatcacagcg gggtttcccc   62880
cctttctagc gagtagctga agaactgttt tctctccttg atggtataac tgtctctgtg   62940
ggtgttgctc ccctgccgct ccagtggttt tgttttgtt tttgttttt tgagacggag     63000 tcttgcgatc tcagctcact gcgacctctg cctcctgggt tcaggcgatt cttctccctc   63060
agccttccat gtagctggga cttacaggca cctgccacca cgcccggctc attttgtat    63120 ttttagtaga cggagtttt caccatgttg gccaggttgg gctcgaactc cagacctcag   63180
gtgatccacc tgcctcagcc tcccacagtg ctgggattac aggtgagagc cactgcaccc   63240
agccggcccc tcagtctttt ccttctcaat cagtggcacc accatcttcc caggctttgg   63300
acatggtccc tgactcaccc ttgcccctca cccccacact aatccacctg cgagctctgt   63360
tgcttcacca cctagaccag ccccaaatcc tcaactgccc ccaccctggg ccacacctgg   63420
accactgcta gaggcctctc atgggccctc cctgttttc tcttgcactc cccgggcttt    63480
ctggcacaag atgccccaga agcagaatca catatctctc ctgggagcca atctagtgtg   63540
tttactgccc ctggagtgtt attgttggcc ttagaatatg tcccactaca ggtttgcaga   63600
gcactgtagt caaaagtcat ttgaaataaa tcttttctct gtggtatatt gtcaatttga   63660
tatagaatta aatttgtttc ttttcttttt tcttttcttt tttttttttt ttaagagaca   63720
gggtcttggc caggcgtggt gtctcatgcc tgtaatcccg gcactttggg aagccaaggt   63780
gggtggatcg cctgaggtca ggaattcaag accaacctgg ccagcatggt gaaacccgt    63840 ctctgctaaa aatacaaaaa ttagccgggc gtgatggcag gtacctgtaa tcccagctac   63900
tcgggaagct gaggcaggag aaggcttgaa ctcaggagtc ggaggttgca gtgagccaag   63960
atcacgccat ggcactctag caagactctg tctcaaaaaa aaaaaagag agagagagag     64020 acagggtctt gctctgtcac tcaggctgga gtgcagtgat gtagtcatgg ctcactgcag   64080
cctcatactc ctgacctcag gtgatcgacc cgcctcggcc tcccaaagtg ctgggatcgt   64140
aggctgaagc caccatgcct ggcccgaact catttgtttt tatttgcatt aagtgtaata   64200
aggttttgtt acttttagtt tgaattttat ttgggtaat ataaacattt acatgattca     64260
gaagtcagaa ttacactgag gcatgttcag ctaggcctca ctcctgtgcc tgtacccta    64320 cctttttccc cctaccccat gcagggaatc aatttcatta gttcctggtg tgtccttcct   64380
taataccccc ccttctttct ttggtagaat gcagtagata tgtttgcgct ttgctcccttt 64440 tgcttcacag tggatcctgg aaatgactcc atcgcagttc ttagagctct tgtttagtcc   64500
ctttggatct gcacagtact ccagtgtgtg ggcgcaccat aagtttattc agcaagtgcc   64560
ctggtgatag ggatcggggg tattggaagc ctttggctgg taaaaataat gttgtagcaa   64620
ataacatcat gcatatgttc tttgagattt ctggaggtgt ctctttagca tagatttcta   64680
gaaggcattc cttacgtcac gtttaggttt atagtttgac ctcatggtga ttaaggtatt   64740
tgggaaatgc aaatgagagt ttcgaagaag ccagatcttt cccattagtt cactgttttt   64800
ctctgacatt aggaccgtcc gggttctagg agcagccct ggcgttaggc agtgccatga    64860
tggattgtgt agaagtagcg attcccatct gtctgctttc ttggcccact ctgctggtgg   64920
ctccccttcc ctccctcctt tatggggagc tggggagctg cctaggggtc cattctcaaa   64980
ggctgatctc tggtgggcaa caggccacac ctagcttcc agggttcttc gtcatttccc    65040
attgagagct gtaagactca gagacatgaa aaggaagctc tggctgggca cggtggctca   65100
```

```
cgcctgtaat cccagcactt tgggaggctg aggcgggtcg atcacctgag gtcaggagtt   65160
cgagaccagc ctgcccaaca tggtgaaacc ccgtctccac taaacataca aaaattagcc   65220
tggcgtggta gcacacgcct gtgatcccag ctactccgga ggctgaggca ggagaataac   65280
ttgaacccgg caggcggagg ttgcgatgag ccgatattat gccatcggca acagagcgag   65340
actccatctc aaaaaaaaaa caaaaaacaa aacaaggcga gctctgtgct gggacagatt   65400
agggacccct ctttacagca agaaagactg ctctgtgggt tgtaggatgc ctttgtgtat   65460
gcagtggctc taggtgactc tggcagccac actctgggcc ctaaacttct ggaggaagat   65520
acaggatagg gaggaactca gggtgagtc atggtgggga caagacattc cctcactcta   65580
agaccttgtc actagattgg aacatctctt gcctccctac acctgacctg atggttctgg   65640
agagatacgt ccttgcagct tctgagtccc agcactaagc agcctttggt aacttccta   65700 catcatttga gttctggttt cctaaggatg cttgccagtg agtgccatgg tgccctcatt   65760
gcacagtctg tgcagtgtag acaagagggg aagtctcttg gggtagacca gccgcaaggc   65820
ggtgactagc actgatgtga accacatggg acagggagt tgtgggctg agaacacgga   65880 gggtgggagt agtcatgctc ttttccagaa tgaactgcta acgaagggac tcgcaggtgg   65940
ctgctgcttc tttccaagct gccctgttg ttgcagaggc tctggagtcc taggaggttt   66000
cacggtggca tactcgacag agtactagag catcatggcc agatagtgat gctgggtgt   66060 ggggcctcac ggtggccatt tctgacgaga ccccaccggg ccaaagtgat gtgtagagaa   66120
ggagctgctt cggtcaccag aaaagaacgg ggaagcctcc cacactgaaa taggtagggt   66180
gctcttctcc accggcagga agggatgta tggctctgcc tggaccacac ctttttcctt   66240
gctcttccct ccgcatctgc tgtggccgag gccattcctc atcagggaac atgtgttaga   66300
ggctcacgcc acctgggacc acttgtctta tcaccccag gaccctaggc ggtagtttcc   66360
tgtggcctga gttagctgat atttatatag tgccattgtg ccttttctcc tgtgatgctc   66420
acagtaagga tgcctagatg gggttacctg ttgtcaagat aaggaaactg aagcacagaa   66480
tgctgaggtc atttgctggg ttcatgtttg gaaagcggca aaggatttca gtgcaggttg   66540
gctggctcca aacctgtgtg tgcttttcat gacactgtac tgtgtgcctc attgagcctc   66600
attctagaaa accaaaaaca cacccaaggc ccggccttca caaaggagac ccctcccca   66660 tttggctccc tttccagcag tcgacggcct cttgtcagcc atcgagccca gagtcccttg   66720
aagtgcgact catgctgggg tggtatgctc aggagccgca gtgtttccgc tcagaggaaa   66780
gggctctgat tctcctgcag tgctaggaga cttgtgggtg ccacagtgc aggtcaggca   66840 caccggccag caccacccac agcccaaatt cctaaagaaa tatttgggtc ccagcttggc   66900
ccgagtctct gttgtcctgg ggaaggacat caagatctga gtgtatgatg gcctgggcc   66960 ttgcatgtgg tgggggtcca agcctgcctc tgctcacttg ttctgcagac tggcatgttc   67020
tctgtgatac ttacatactt gtttaacact tcagggaaga aaagtcagaa gaccaggacc   67080
tccagggcct caaggacaaa cccctcaagt ttaaaaggt gaagaaagat aagaaagaag   67140
agaaagaggg caagcatgag cccgtgcagc catcagccca ccactctgct gagcccgcag   67200
aggcaggcaa agcagagaca tcagaaggg caggctccgc cccggctgtg ccggaagctt   67260
ctgcctcccc caaacagcgg cgctccatca tccgtgaccg ggacccatg tatgatgacc   67320 ccaccctgcc tgaaggctgg acacggaagc ttaagcaaag gaaatctggc cgctctgctg   67380
ggaagtatga tgtgtatttg atcaagtaag taagagcaac tcctatctct acagggcagg   67440
```

```
gagggcaggg acaaggatcc ctcatggagc aggaaaatgt atgtgcccag ggtggggtcg   67500
gggggaacat aaacaatgaa cactgagacc aggtgtgctt gaaatgaccg tgtacagagg   67560
tcgctgccct gagtgggaag ttctcaaggt agcaggccct ctatcctctc cacacctcaa   67620
gtctttatct ggggatggaa tagctgcgga agcagaggaa cttgcagagc taggggttca   67680
gaggggtgaa gaagcatgtt tcagttctgc cttttaaatg atcccaaaaa ggttagcagt   67740
tttcaaatga catttgcaga cagcctcatt taattccatg agaagggtga gcaaaggatt   67800
atcttgttga aactgattcc tggagagact gagcaccgta cctgagttca aacttgggaa   67860
tgttctagat ggtgactcag gcccaggcac caaccagcag aatgggcctc agcctgacaa   67920
cccttctgta ccaggcctga ctctttggtt gctgaacttt ggagaggcct ggggggggtca   67980 gcggcaggca gacgagtgag tggctttggt gacaggtcct cagggcagc caggcagtgt   68040 gactctcgtt caatagtaac gtttgtcaga gcgttgtcac caccatccgc tctgccctat   68100
ctctgacatt gctatggaga gcctctaatt gttccttgtg tctttctgtt tgtccccaca   68160
gtccccaggg aaaagccttt cgctctaaag tggagttgat tgcgtacttc gaaaaggtag   68220
gcgacacatc cctggaccct aatgattttg acttcacggt aactgggaga gggagcccct   68280
cccggcgaga gcagaaacca cctaagaagc ccaaatctcc caaagctcca ggaactggca   68340
gaggccgggg acgccccaaa gggagcggca ccacgagacc caaggcggcc acgtcagagg   68400
gtgtgcaggt gaaaagggtc ctggagaaaa gtcctgggaa gctccttgtc aagatgcctt   68460
ttcaaacttc gccagggggc aaggctgagg ggggtggggc caccacatcc acccaggtca   68520
tggtgatcaa acgccccggc aggaagcgaa aagctgaggc cgaccctcag gccattccca   68580
agaaacgggg ccgaaagccg gggagtgtgg tggcagccgc tgccgccgag gccaaaaaga   68640
aagccgtgaa ggagtcttct atccgatctg tgcaggagac cgtactcccc atcaagaagc   68700
gcaagacccg ggagacggtc agcatcgagg tcaaggaagt ggtgaagccc ctgctggtgt   68760
ccaccctcgg tgagaagagc gggaaaggac tgaagacctg taagagccct gggcggaaaa   68820
gcaaggagag cagccccaag gggcgcagca gcagcgcctc ctcacccccc aagaaggagc   68880
accaccacca tcaccaccac tcagagtccc caaaggcccc cgtgccactg ctcccacccc   68940
tgcccccacc tccacctgag cccgagagct ccgaggaccc caccagcccc cctgagcccc   69000
aggacttgag cagcagcgtc tgcaaagagg agaaagatgcc cagaggaggc tcactggaga   69060
gcgacggctg ccccaaggag ccagctaaga ctcagcccgc ggttgccacc gccgccacgg   69120
ccgcagaaaa gtacaaacac cgaggggagg gagagcgcaa agacattgtt tcatcctcca   69180
tgccaaggcc aaacagagag gagcctgtgg acagccggac gcccgtgacc gagagagtta   69240
gctgacttta cacggagcgg attgcaaagc aaaccaacaa gaataaaggc agctgttgtc   69300
tcttctcctt atgggtaggg ctctgacaaa gcttcccgat taactgaaat aaaaaatatt   69360 ttttttctt tcagtaaact tagagtttcg tggcttcagg gtgggagtag ttggagcatt   69420
ggggatgttt ttcttaccga caagcacagt caggttgaag acctaaccag gccagaagt   69480 agctttgcac ttttctaaac taggctcctt caacaaggct tgctgcagat actactgacc   69540
agacaagctg ttgaccaggc acctcccctc ccgcccaaac ctttccccca tgtggtcgtt   69600
agagacagag cgacagagca gttgagagga cactcccgtt ttcggtgcca tcagtgcccc   69660
gtctacagct ccccccagctc cccccaccctc ccccactccc aaccacgttg ggacagggag   69720
gtgtgaggca ggagagacag ttggattctt tagagaagat ggatatgacc agtggctatg   69780
gcctgtgcga tcccacccgt ggtggctcaa gtctggcccc acaccagccc caatccaaaa   69840
```

| | |
|---|---|
| ctggcaagga cgcttcacag gacaggaaag tggcacctgt ctgctccagc tctggcatgg | 69900 |
| ctaggagggg ggagtccctt gaactactgg gtgtagactg gcctgaacca caggagagga | 69960 |
| tggcccaggg tgaggtggca tggtccattc tcaagggacg tcctccaacg ggtggcgcta | 70020 |
| gaggccatgg aggcagtagg acaaggtgca ggcaggctgg cctggggtca ggccgggcag | 70080 |
| agcacagcgg ggtgagaggg attcctaatc actcagagca gtctgtgact tagtggacag | 70140 |
| gggaggggc aaaggggag gagaagaaaa tgttcttcca gttactttcc aattctcctt | 70200 |
| tagggacagc ttagaattat ttgcactatt gagtcttcat gttcccactt caaaacaaac | 70260 |
| agatgctctg agagcaaact ggcttgaatt ggtgacattt agtccctcaa gccaccagat | 70320 |
| gtgacagtgt tgagaactac ctggatttgt atatatacct gcgcttgttt taaagtgggc | 70380 |
| tcagcacata gggttcccac gaagctccga aactctaagt gtttgctgca attttataag | 70440 |
| gacttcctga ttggtttctc ttctcccctt ccatttctgc cttttgttca tttcatcctt | 70500 |
| tcacttcttt cccttcctcc atcctcctcc ttcctagttc atcccttctc ttccaggcag | 70560 |
| ccgcggtgcc caaccacact tgtcggctcc agtccccaga actctgcctg cccctttgtcc | 70620 |
| tcctgctgcc agtaccagcc ccaccctgtt ttgagccctg aggaggcctt gggctctgct | 70680 |
| gagtccgacc tggcctgtct gtgaagagca agagagcagc aaggtcttgc tctcctaggt | 70740 |
| agcccctct tccctggtaa gaaaaagcaa aaggcatttc ccaccctgaa caacgagcct | 70800 |
| tttcacccctt ctactctaga gaagtggact ggaggagctg ggcccgattt ggtagttgag | 70860 |
| gaaagcacag aggcctcctg tggcctgcca gtcatcgagt ggcccaacag gggctccatg | 70920 |
| ccagccgacc ttgacctcac tcagaagtcc agagtctagc gtagtgcagc agggcagtag | 70980 |
| cggtaccaat gcagaactcc caagacccga gctgggacca gtacctgggt ccccagccct | 71040 |
| tcctctgctc cccctttttcc ctcggagttc ttcttgaatg gcaatgttttt gcttttgctc | 71100 |
| gatgcagaca gggggccaga acaccacaca tttcactgtc tgtctggtcc atagctgtgg | 71160 |
| tgtaggggct tagaggcatg ggcttgctgt gggttttttaa ttgatcagtt ttcatgtggg | 71220 |
| atcccatctt tttaacctct gttcaggaag tccttatcta gctgcatatc ttcatcatat | 71280 |
| tggtatatcc ttttctgtgt ttacagagat gtctcttata tctaaatctg tccaactgag | 71340 |
| aagtacctta tcaaagtagc aaatgagaca gcagtcttat gcttccagaa acacccacag | 71400 |
| gcatgtccca tgtgagctgc tgccatgaac tgtcaagtgt gtgttgtctt gtgtatttca | 71460 |
| gttattgtcc ctggcttcct tactatggtg taatcatgaa ggagtgaaac atcatagaaa | 71520 |
| ctgtctagca cttccttgcc agtctttagt gatcaggaac catagttgac agttccaatc | 71580 |
| agtagcttaa gaaaaaaccg tgtttgtctc ttctggaatg gttagaagtg agggagtttg | 71640 |
| ccccgttctg tttgtagagt ctcatagttg gactttctag catatatgtg tccatttcct | 71700 |
| tatgctgtaa aagcaagtcc tgcaaccaaa ctcccatcag cccaatccct gatccctgat | 71760 |
| cccttccacc tgctctgctg atgaccccccc cagcttcact tctgactctt ccccaggaag | 71820 |
| ggaaggggg tcagaagaga gggtgagtcc tccagaactc ttcctccaag gacagaaggc | 71880 |
| tcctgccccc atagtggcct cgaactcctg gcactaccaa aggacactta tccacgagag | 71940 |
| cgcagcatcc gaccaggttg tcactgagaa gatgtttatt ttggtcagtt gggttttttat | 72000 |
| gtattatact tagtcaaatg taatgtggct tctggaatca ttgtccagag ctgcttcccc | 72060 |
| gtcacctggg cgtcatctgg tcctggtaag aggagtgcgt ggcccaccag gccccccctgt | 72120 |
| cacccatgac agttcattca gggccgatgg ggcagtcgtg gttgggaaca cagcatttca | 72180 |

```
agcgtcactt tatttcattc gggccccacc tgcagctccc tcaaagaggc agttgcccag   72240
cctctttccc ttccagttta ttccagagct gccagtgggg cctgaggctc cttagggttt   72300
tctctctatt tccccctttc ttcctcattc cctcgtcttt cccaaaggca tcacgagtca   72360
gtcgcctttc agcaggcagc cttggcggtt tatcgccctg gcaggcaggg gccctgcagc   72420
tctcatgctg cccctgcctt ggggtcaggt tgacaggagg ttggagggaa agccttaagc   72480
tgcaggattc tcaccagctg tgtccggccc agtttggggg tgtgacctca atttcaattt   72540
tgtctgtact tgaacattat gaagatgggg gcctctttca gtgaatttgt gaacagcaga   72600
attgaccgac agcttttccag tacccatggg gctaggtcat taaggccaca tccacagtct   72660
cccccaccct tgttccagtt gttagttact acctcctctc ctgacaatac tgtatgtcgt   72720
cgagctcccc ccaggtctac ccctcccggc cctgcctgct ggtgggcttg tcatagccag   72780
tgggattgcc ggtcttgaca gctcagtgag ctggagatac ttggtcacag ccaggcgcta   72840
gcacagctcc cttctgttga tgctgtattc ccatatcaaa agacacaggg gacacccaga   72900
aacgccacat cccccaatcc atcagtgcca aactagccaa cggccccagc ttctcagctc   72960
gctggatggc ggaagctgct actcgtgagc gccagtgcgg gtgcagacaa tcttctgttg   73020
ggtggcatca ttccaggccc gaagcatgaa cagtgcacct gggacaggga gcagcccaa   73080
attgtcacct gcttctctgc ccagcttttc attgctgtga cagtgatggc gaaagagggt   73140
aataaccaga cacaaactgc caagttgggt ggagaaagga gtttctttag ctgacagaat   73200
ctctgaattt taaatcactt agtaagcggc tcaagcccag gagggagcag agggatacga   73260
gcggagtccc ctgcgcggga ccatctggaa ttggtttagc ccaagtggag cctgacagcc   73320
agaactctgt gtccccgtc taaccacagc tccttttcca gagcattcca gtcaggctct   73380
ctgggctgac tgggccaggg gaggttacag gtaccagttc tttaagaaga tctttgggca   73440
tatacatttt tagcctgtgt cattgcccca aatggattcc tgtttcaagt tcacacctgc   73500
agattctagg acctgtgtcc tagacttcag ggagtcagct gtttctagag ttcctaccat   73560
ggagtgggtc tggaggacct gcccggtggg ggggcagagc cctgctccct ccgggtcttc   73620
ctactcttct ctctgctctg acgggatttg ttgattctct ccattttggt gtctttctct   73680
tttagatatt gtatcaatct ttagaaaagg catagtctac ttgttataaa tcgttaggat   73740
actgcctccc ccagggtcta aaattacata ttagagggga aaagctgaac actgaagtca   73800
gttctcaaca atttagaagg aaaacctaga aaacatttgg cagaaaatta catttcgatg   73860
tttttgaatg aatacgagca agcttttaca acagtgctga tctaaaaata cttagcactt   73920
ggcctgagat gcctggtgag cattacaggc aaggggaatc tggaggtagc cgacctgagg   73980
acatggcttc tgaacctgtc tttttgggagt ggtatggaag gtggagcgtt caccagtgac   74040
ctggaaggcc cagcaccacc ctccttccca ctcttctcat cttgacagag cctgccccag   74100
cgctgacgtg tcaggaaaac acccagggaa ctaggaaggc acttctgcct gaggggcagc   74160
ctgccttgcc cactcctgct ctgctcgcct cggatcagct gagccttctg agctggcctc   74220
tcactgcctc cccaaggccc cctgcctgcc ctgtcaggag gcagaaggaa gcaggtgtga   74280
gggcagtgca aggagggagc acaaccccca gctcccgctc cgggctccga cttgtgcaca   74340
ggcagagccc agaccctgga ggaaatccta cctttgaatt caagaacatt tggggaattt   74400
ggaaatctct ttgcccccaa accccattc tgtcctacct ttaatcaggt cctgctcagc   74460
agtgagagca gatgaggtga aaaggccaag aggtttggct cctgcccact gatagcccct   74520
ctccccgcag tgtttgtgtg tcaagtggca aagctgttct tcctggtgac cctgattata   74580
```

```
tccagtaaca catagactgt gcgcataggc ctgctttgtc tcctctatcc tgggcttttg    74640
ttttgctttt tagttttgct tttagttttt ctgtcccttt tatttaacgc accgactaga    74700
cacacaaagc agttgaattt ttatatatat atctgtatat tgcacaatta taaactcatt    74760
ttgcttgtgg ctccacacac acaaaaaaag acctgttaaa attatacctg ttgcttaatt    74820
acaatatttc tgataaccat agcataggac aagggaaaat aaaaaagaa  aaaaagaaa     74880 aaaaaacgac aaatctgtct gctggtcact tcttctgtcc aagcagattc gtggtctttt    74940
cctcgcttct ttcaagggct ttcctgtgcc aggtgaagga ggctccaggc agcacccagg    75000
ttttgcactc ttgtttctcc cgtgcttgtg aaagaggtcc caaggttctg ggtgcaggag    75060
cgctcccttg acctgctgaa gtccggaacg tagtcggcac agcctggtcg ccttccacct    75120
ctgggagctg gagtccactg gggtggcctg actcccccag tccccttccc gtgacctggt    75180
cagggtgagc ccatgtggag tcagcctcgc aggcctccct gccagtaggg tccgagtgtg    75240
tttcatcctt cccactctgt cgagcctggg ggctggagcg gagacgggag gcctggcctg    75300
tctcggaacc tgtgagctgc accaggtaga acgccaggga ccccagaatc atgtgcgtca    75360
gtccaagggg tcccctccag gagtagtgaa gactccagaa atgtccctt  cttctccccc    75420 atcctacgag taattgcatt tgcttttgta attcttaatg agcaatatct gctagagagt    75480
ttagctgtaa cagttctttt tgatcatctt tttttaataa ttagaaacac caaaaaaatc    75540
cagaaacttg ttcttccaaa gcagagagca ttataatcac cagggccaaa agcttccctc    75600
cctgctgtca ttgcttcttc tgaggcctga atccaaaaga aaacagcca  taggcccttt    75660 cagtggccgg gctacccgtg agcccttcgg aggaccaggg ctggggcagc ctctgggccc    75720
acatccgggg ccagctccgg cgtgtgttca gtgttagcag tgggtcatga tgctctttcc    75780
cacccagcct gggatagggg cagaggaggc gaggaggccg ttgccgctga tgtttggccg    75840
tgaacaggtg ggtgtctgcg tgcgtccacg tgcgtgtttt ctgactgaca tgaaatcgac    75900
gcccgagtta gcctcacccg gtgacctcta gccctgcccg gatggagcgg ggcccacccg    75960
gttcagtgtt tctggggagc tggacagtgg agtgcaaaag gcttcagaa  cttgaagcct    76020 gctccttccc ttgctaccac ggcctccttt ccgtttgatt tgtcactgct tcaatcaata    76080
acagccgctc cagagtcagt agtcaatgaa tatatgacca aatatcacca ggactgttac    76140
tcaatgtgtg ccgagccctt gcccatgctg ggctcccgtg tatctggaca ctgtaacgtg    76200
tgctgtgttt gctccccttc cccttccttc tttgccctt  acttgtcttt ctggggtttt    76260
tctgtttggg tttggtttgg tttttatttc tccttttgtg ttccaaacat gaggttctct    76320
ctactggtcc tcttaactgt ggtgttgagg cttatatttg tgtaattttt ggtgggtgaa    76380
aggaattttg ctaagtaaat ctcttctgtg tttgaactga agtctgtatt gtaactatgt    76440
ttaaagtaat tgttccagag acaaatattt ctagacactt tttctttaca aacaaaagca    76500
ttcggaggga gggggatggt gactgagatg agaggggaga gctgaacaga tgaccctgc     76560 ccagatcagc cagaagccac ccaaagcagt ggagcccagg agtcccactc caagccagca    76620
agccgaatag ctgatgtgtt gccactttcc aagtcactgc aaaaccaggt tttgttccgc    76680
ccagtggatt cttgttttgc ttcccctccc cccgagatta ttaccaccat cccgtgcttt    76740
taaggaaagg caagattgat gtttccttga ggggagccag gagggatgt  gtgtgtgcag    76800 agctgaagag ctggggagaa tggggctggg cccacccaag caggaggctg ggacgctctg    76860
ctgtgggcac aggtcaggct aatgttggca gatgcagctc ttcctggaca ggccaggtgg    76920
```

```
tgggcattct ctctccaagg tgtgccccgt gggcattact gtttaagaca cttccgtcac   76980
atcccacccc atcctccagg gctcaacact gtgacatctc tattccccac cctcccttc    77040 ccagggcaat aaaatgacca tggagggggc ttgcactctc ttggctgtca cccgatcgcc   77100
agcaaaactt agatgtgaga aaacccttc ccattccatg gcgaaaacat ctccttagaa    77160
aagccattac cctcattagg catggttttg ggctcccaaa acacctgaca gcccctccct   77220
cctctgagag gcggagagtg ctgactgtag tgaccattgc atgccgggtg cagcatctgg   77280
aagagctagg cagggtgtct gcccctcct gagttgaagt catgctcccc tgtgccagcc    77340
cagaggccga gagctatgga cagcattgcc agtaacacag gccaccctgt gcagaaggga   77400
gctggctcca gcctggaaac ctgtctgagg ttgggagagg tgcacttggg gcacagggag   77460
aggccgggac acacttagct ggagatgtct ctaaaagccc tgtatcgtat tcaccttcag   77520
tttttgtgtt ttgggacaat tactttagaa ataagtagg tcgttttaaa aacaaaaatt    77580
attgattgct tttttgtagt gttcagaaaa aaggttcttt gtgtatagcc aaatgactga   77640
aagcactgat atatttaaaa acaaaaggca atttattaag gaaatttgta ccatttcagt   77700
aaacctgtct gaatgtacct gtatacgttt caaaaacacc cccccccac tgaatccctg    77760 taacctattt attatataaa gagtttgcct tataaattta cataaaaatg tccgtttgtg   77820
tcttttgttg taaaaatcaa gtgatttttt cataaggttc ttttactatt ggaaaagatg   77880
ggcagcacgc agttttattt tatttttgta agttttttaa tacatgtgaa agcaaagaat   77940
actcagcatg cctttctaag tgacgcgttt gcacctttg ttgggaagta ctgtatcctg    78000
tgctgttagc attctcgata aatctctctg tgaaagtgac tcaaggtctg ggctttcatt   78060
ataagacaga agtcccctc cagctcacat gacagcatgg tgctgcgttt cctcattgga    78120
tctggctgtc cctggacaca ggtagctgcc ttcaggcctg ccacgagcgg ccaagggaag   78180
cctcctccat atgctggcct cgctggcccc tcagcttctt ccaagccagt gctctccagg   78240
cacactgctc cagcgtgtga cgggaagggc ctggcatgag tcagcctgca gcacaacctc   78300
cctgctccag acccgtatgg taggggcacc cctaggtct ggatgtgctg tggtgctttt    78360
ggacaccccc accccgcag gctgtggctc ctcctgtgtc tcattctggc caggaccctc    78420
acgtgccctc tgttgactgc taacgtggtt ctctgaccag gcaagggcag gctgagggt    78480 ttgcccaaag gggccccct tgttactggc ttccttggct ctcaggagca gcctcaccag    78540
gttggtaagg ggctggagga gacaactgct caaaggagtc cagcttcaca tgcacatgct   78600
agaaggtacc ctcggaaggc ctggccttca aaggtagatc ccagggttga aaagtcaact   78660
tgtatgcatt gagcatctcg tatgccagcc ctgttccgtg agctgatggg cctttgtgtg   78720
taagtaggac caagtgcccc cgtggaggtt agcatgggtg tgcagtcatt tcagatactt   78780
gagttggtac atctcagtaa agtctgtccc gtgagaagcc atgggtttca tggtatggtt   78840
ggcatcttcc ttgggagtgg ccacagtggt ggtggcttca ggaaagagac tccaacaggg   78900
gccagctgtg ggccttgggc acttctcgtt tctaggaaaa gtcctaagtc tgtagggcta   78960
ggggtgggga acccccttcgc tgtcaggatc aagagggcaa ggggaactgt cgctggagga   79020
gacatccagc tggagaaaca aaagagtaag tctgcgttgc tgcttgtggg gtcttcccca   79080
tctcagggcg gggaccgggg gtggcggtcc agacaagtaa tcaaggacga tgcccaggag   79140
gggacaggta cggggtggca ggagctctgc cggcgggctc aggaagcctt caccacagct   79200
gcctgagctc acccttgcca aatgagggct ggggcagcag caacgcatac actcacggct   79260
gtggcgggca gcgttctcgg catatttcag gacacctaag gagactgaat ggctcaaggc   79320
```

-continued

```
tgctgccgtg tgcagggggc tagacgtggg gcgggcaggc agggctcctg gtaacagccc    79380
tgcaggccgc agtggagagc agggttccgg cagggccgcc caggagcttt cggaaggccc    79440
ggccccggcc cctttccgag cagcccgggc ctccgccctg ccctctgtcc ccaacgccgg    79500
gagccgccgt tcgtcctcca gagccccgcc cgggcgagcc cggaggccg atcgccgctc     79560
gcggaacccg ccgggacccg ggccctcccc ggcgcggggc gccccgtgt gacccagcgc     79620
gcggccgcg cgcgcaagat ggcggcgggc ccgggcaccg cccttccgc ccgccgggc      79680
gtcgcacgag gccggctcga aggggaagtg agtcagtgtc cgcggacccg gccggcccag    79740
gcccgcgccc gccgcggccc tgagaggccc cggcaggtcc cggcccggcg gcggcagcca   79800
tggccggggg gccgggcccg ggggagcccg cagcccccgg cgcccagcac ttcttgtacg   79860
aggtgccgcc ctgggtcatg tgccgcttct acaaagtgat ggacgccctg gagcccgccg   79920
actggtgcca gttcggtggg tggcggcggg ctgccggggg gcgggaggcg cgcgggctcc   79980
tggcgccgac gcctgacgcc c                                             80001

<210> SEQ ID NO 2
<211> LENGTH: 10241
<212> TYPE: DNA
<213> ORGANISM: Homo sapiens

<400> SEQUENCE: 2
ccggcgtcgg cggcgcgcgc gctccctcct ctcggagaga gggctgtggt aaaagccgtc      60
cggaaaatgg ccgccgccgc cgccgccgcg ccgagcggag gaggaggagg aggcgaggag     120
gagagactgc tccataaaaa tacagactca ccagttcctg ctttgatgtg acatgtgact     180
ccccagaata caccttgctt ctgtagacca gctccaacag gattccatgg tagctgggat     240
gttagggctc agggaagaaa agtcagaaga ccaggacctc cagggcctca aggacaaacc     300
cctcaagttt aaaaaggtga agaaagataa gaaagaagag aaagagggca agcatgagcc     360
cgtgcagcca tcagcccacc actctgctga gcccgcagag gcaggcaaag cagagacatc     420
agaagggtca ggctccgccc cggctgtgcc ggaagcttct gcctccccca acagcggcg      480
ctccatcatc cgtgaccggg gacccatgta tgatgacccc accctgcctg aaggctggac    540
acggaagctt aagcaaagga atctggccg ctctgctggg aagtatgatg tgtatttgat     600
caatccccag ggaaaagcct ttcgctctaa agtggagttg attgcgtact cgaaaaggt     660
aggcgacaca tccctggacc ctaatgattt tgacttcacg gtaactggga gggagccc       720
ctcccggcga gagcagaaac cacctaagaa gcccaaatct cccaaagctc caggaactgg    780
cagaggccgg ggacgcccca aagggagcgg caccacgaga cccaaggcgg ccacgtcaga   840
gggtgtgcag gtgaaaaggg tcctggagaa aagtcctggg aagctccttg tcaagatgcc   900
ttttcaaact tcgccagggg gcaaggctga gggggtgggg gccaccacat ccacccaggt   960
catggtgatc aaacgccccg gcaggaagcg aaaagctgag gccgaccctc aggccattcc   1020
caagaaacgg ggccgaaagc cggggagtgt ggtggcagcc gctgccgccg aggccaaaaa   1080
gaaagccgtg aaggagtctt ctatccgatc tgtgcaggag accgtactcc ccatcaagaa   1140
gcgcaagacc cgggagacgg tcagcatcga ggtcaaggaa gtggtgaagc ccctgctggt   1200
gtccacctc ggtgagaaga gcgggaaagg actgaagacc tgtaagagcc ctgggcggaa    1260
aagcaaggag agcagcccca aggggcgcag cagcagcgcc tcctcacccc caagaagga    1320
gcaccaccac catcaccacc actcagagtc cccaaaggcc ccgtgccac tgctcccacc    1380
```

```
cctgccccca cctccacctg agcccgagag ctccgaggac cccaccagcc cccctgagcc     1440
ccaggacttg agcagcagcg tctgcaaaga ggagaagatg cccagaggag gctcactgga     1500
gagcgacggc tgccccaagg agccagctaa gactcagccc gcggttgcca ccgccgccac     1560
ggccgcagaa aagtacaaac accgagggga gggagagcgc aaagacattg tttcatcctc     1620
catgccaagg ccaaacagag aggagcctgt ggacagccgg acgcccgtga ccgagagagt     1680
tagctgactt tacacggagc ggattgcaaa gcaaaccaac aagaataaag gcagctgttg     1740
tctcttctcc ttatgggtag ggctctgaca aagcttcccg attaactgaa ataaaaaata     1800
ttttttttc tttcagtaaa cttagagttt cgtggcttca gggtgggagt agttggagca     1860
ttggggatgt ttttcttacc gacaagcaca gtcaggttga agacctaacc agggccagaa     1920
gtagctttgc acttttctaa actaggctcc ttcaacaagg cttgctgcag atactactga     1980
ccagacaagc tgttgaccag gcacctcccc tcccgcccaa acctttcccc catgtggtcg     2040
ttagagacag agcgcagag cagttgagag gacactcccg ttttcggtgc catcagtgcc     2100
ccgtctacag ctcccccagc tcccccacc tccccactc caaccacgt tgggacaggg     2160
aggtgtgagg caggagagac agttggattc tttagagaag atggatatga ccagtggcta     2220
tggcctgtgc gatcccaccc gtggtggctc aagtctggcc ccacaccagc cccaatccaa     2280
aactggcaag gacgcttcac aggacaggaa agtggcacct gtctgctcca gctctggcat     2340
ggctaggagg ggggagtccc ttgaactact gggtgtagac tggcctgaac cacaggagag     2400
gatggcccag ggtgaggtgg catggtccat tctcaaggga cgtcctccaa cgggtggcgc     2460
tagaggccat ggaggcagta ggacaaggtg caggcaggct ggcctggggt caggccgggc     2520
agagcacagc ggggtgagag ggattcctaa tcactcagag cagtctgtga cttagtggac     2580
aggggagggg gcaaaggggg aggagaagaa aatgttcttc cagttacttt ccaattctcc     2640
tttagggaca gcttagaatt atttgcacta ttgagtcttc atgttcccac ttcaaaacaa     2700
acagatgctc tgagagcaaa ctggcttgaa ttggtgacat ttagtccctc aagccaccag     2760
atgtgacagt gttgagaact acctggattt gtatatatac ctgcgcttgt tttaaagtgg     2820
gctcagcaca tagggttccc acgaagctcc gaaactctaa gtgtttgctg caattttata     2880
aggacttcct gattggtttc tcttctcccc ttccatttct gccttttgtt catttcatcc     2940
tttcacttct ttcccttcct ccgtcctcct ccttcctagt tcatcccttc tcttccaggc     3000
agccgcggtg cccaaccaca cttgtcggct ccagtcccca gaactctgcc tgcccttttgt    3060
cctcctgctg ccagtaccag ccccaccctg ttttgagccc tgaggaggcc ttgggctctg     3120
ctgagtccga cctggcctgt ctgtgaagag caagagagca gcaaggtctt gctctcctag     3180
gtagcccct cttccctggt aagaaaaagc aaaaggcatt tcccaccctg aacaacgagc     3240
cttttcaccc ttctactcta gagaagtgga ctggaggagc tgggcccgat tggtagttg     3300
aggaaagcac agaggcctcc tgtggcctgc cagtcatcga gtgcccaac aggggctcca     3360
tgccagccga ccttgacctc actcagaagt ccagagtcta gcgtagtgca gcagggcagt     3420
agcggtacca atgcagaact cccaagaccc gagctgggac cagtacctgg gtccccagcc     3480
cttcctctgc tccccctttt ccctcggagt tcttcttgaa tggcaatgtt ttgcttttgc     3540
tcgatgcaga caggggcca gaacaccaca catttcactg tctgtctggt ccatagctgt     3600
ggtgtagggg cttagaggca tgggcttgct gtgggttttt aattgatcag ttttcatgtg     3660
ggatcccatc ttttttaacct ctgttcagga agtccttatc tagctgcata tcttcatcat     3720
attggtatat cctttttctgt gtttacagag atgtctctta tatctaaatc tgtccaactg     3780
```

```
agaagtacct tatcaaagta gcaaatgaga cagcagtctt atgcttccag aaacacccac   3840
aggcatgtcc catgtgagct gctgccatga actgtcaagt gtgtgttgtc ttgtgtattt   3900
cagttattgt ccctggcttc cttactatgg tgtaatcatg aaggagtgaa acatcataga   3960
aactgtctag cacttccttg ccagtcttta gtgatcagga accatagttg acagttccaa   4020
tcagtagctt aagaaaaaac cgtgtttgtc tcttctggaa tggttagaag tgagggagtt   4080
tgccccgttc tgtttgtaga gtctcatagt tggactttct agcatatatg tgtccatttc   4140
cttatgctgt aaaagcaagt cctgcaacca aactcccatc agcccaatcc ctgatccctg   4200
atcccttcca cctgctctgc tgatgacccc cccagcttca cttctgactc ttccccagga   4260
agggaagggg ggtcagaaga gagggtgagt cctccagaac tcttcctcca aggacagaag   4320
gctcctgccc ccatagtggc ctcgaactcc tggcactacc aaaggacact tatccacgag   4380
agcgcagcat ccgaccaggt tgtcactgag aagatgttta ttttggtcag ttgggttttt   4440
atgtattata cttagtcaaa tgtaatgtgg cttctggaat cattgtccag agctgcttcc   4500
ccgtcacctg ggcgtcatct ggtcctggta agaggagtgc gtggcccacc aggcccccct   4560
gtcacccatg acagttcatt cagggccgat ggggcagtcg tggttgggaa cacagcattt   4620
caagcgtcac tttatttcat tcgggcccca cctgcagctc cctcaaagag gcagttgccc   4680
agcctctttc ccttccagtt tattccagag ctgccagtgg ggcctgaggc tccttagggt   4740
tttctctcta tttcccccctt tcttcctcat tccctcgtct ttcccaaagg catcacgagt   4800
cagtcgcctt tcagcaggca gccttggcgg tttatcgccc tggcaggcag gggccctgca   4860
gctctcatgc tgcccctgcc ttggggtcag gttgacagga ggttggaggg aaagccttaa   4920
gctgcaggat tctcaccagc tgtgtccggc ccagttttgg ggtgtgacct caatttcaat   4980
tttgtctgta cttgaacatt atgaagatgg gggcctcttt cagtgaattt gtgaacagca   5040
gaattgaccg acagctttcc agtacccatg gggctaggtc attaaggcca catccacagt   5100
ctcccccacc cttgttccag ttgttagtta ctacctcctc tcctgacaat actgtatgtc   5160
gtcgagctcc ccccaggtct acccctcccg gccctgcctg ctggtgggct tgtcatagcc   5220
agtgggattg ccggtcttga cagctcagtg agctggagat acttggtcac agccaggcgc   5280
tagcacagct cccttctgtt gatgctgtat tcccatatca aaagacacag gggacaccca   5340
gaaacgccac atcccccaat ccatcagtgc caaactagcc aacggcccca gcttctcagc   5400
tcgctggatg gcggaagctg ctactcgtga gcgccagtgc gggtgcagac aatcttctgt   5460
tgggtggcat cattccaggc ccgaagcatg aacagtgcac ctgggacagg gagcagcccc   5520
aaattgtcac ctgcttctct gcccagcttt tcattgctgt gacagtgatg gcgaaagagg   5580
gtaataacca gacacaaact gccaagttgg gtggagaaag gagtttcttt agctgacaga   5640
atctctgaat tttaaatcac ttagtaagcg gctcaagccc aggagggagc agagggatac   5700
gagcggagtc ccctgcgcgg gaccatctgg aattggttta gcccaagtgg agcctgacag   5760
ccagaactct gtgtccccg tctaaccaca gctccttttc cagagcattc cagtcaggct   5820
ctctgggctg actgggccag gggaggttac aggtaccagt tctttaagaa gatctttggg   5880
catatacatt tttagcctgt gtcattgccc caaatggatt cctgtttcaa gttcacacct   5940
gcagattcta ggacctgtgt cctagacttc agggagtcag ctgtttctag agttcctacc   6000
atggagtggg tctggaggac ctgcccggtg ggggggcaga gccctgctcc ctccgggtct   6060
tcctactctt ctctctgctc tgacgggatt tgttgattct ctccattttg gtgtctttct   6120
```

```
cttttagata ttgtatcaat ctttagaaaa ggcatagtct acttgttata aatcgttagg    6180
atactgcctc ccccagggtc taaaattaca tattagaggg gaaaagctga acactgaagt    6240
cagttctcaa caatttagaa ggaaaaccta gaaaacattt ggcagaaaat tacatttcga    6300 tgttttgaa tgaatacgag caagctttta caacagtgct gatctaaaaa tacttagcac     6360
ttggcctgag atgcctggtg agcattacag gcaagggaa tctggaggta gccgacctga     6420
ggacatggct tctgaacctg tcttttggga gtggtatgga aggtggagcg ttaccagtg     6480 acctggaagg cccagcacca ccctccttcc cactcttctc atcttgacag agcctgcccc    6540
agcgctgacg tgtcaggaaa cacccaggg aactaggaag gcacttctgc ctgaggggca     6600
gcctgccttg cccactcctg ctctgctcgc ctcggatcag ctgagccttc tgagctggcc    6660
tctcactgcc tccccaaggc ccctgcctg ccctgtcagg aggcagaagg aagcaggtgt     6720
gagggcagtg caaggaggga gcacaacccc cagctcccgc tccgggctcc gacttgtgca    6780
caggcagagc ccagaccctg gaggaaatcc tacctttgaa ttcaagaaca tttggggaat    6840
ttggaaatct ctttgccccc aaaccccat tctgtcctac ctttaatcag gtcctgctca     6900
gcagtgagag cagatgaggt gaaaaggcca agaggtttgg ctcctgccca ctgatagccc    6960
ctctccccgc agtgtttgtg tgtcaagtgg caaagctgtt cttcctggtg accctgatta    7020
tatccagtaa cacatagact gtgcgcatag gcctgctttg tctcctctat cctgggcttt    7080
tgttttgctt tttagttttg cttttagttt ttctgtccct tttatttaac gcaccgacta    7140
gacacacaaa gcagttgaat ttttatatat atatctgtat attgcacaat tataaactca    7200
ttttgcttgt ggctccacac acacaaaaaa agacctgtta aaattatacc tgttgcttaa    7260
ttacaatatt tctgataacc atagcatagg acaagggaaa ataaaaaaag aaaaaaaga     7320 aaaaaaacg acaaatctgt ctgctggtca cttcttctgt ccaagcagat tcgtggtctt    7380
ttcctcgctt ctttcaaggg ctttcctgtg ccaggtgaag gaggctccag gcagcaccca    7440
ggttttgcac tcttgtttct cccgtgcttg tgaaagaggt cccaaggttc tgggtgcagg    7500
agcgctccct tgacctgctg aagtccggaa cgtagtcggc acagcctggt cgccttccac    7560
ctctgggagc tggagtccac tggggtggcc tgactccccc agtccccttc ccgtgacctg    7620
gtcagggtga gcccatgtgg agtcagcctc gcaggcctcc ctgccagtag ggtccgagtg    7680
tgtttcatcc ttcccactct gtcgagcctg gggctggag cggagacggg aggcctggcc     7740
tgtctcggaa cctgtgagct gcaccaggta gaacgccagg gaccccagaa tcatgtgcgt    7800
cagtccaagg ggtcccctcc aggagtagtg aagactccag aaatgtccct tcttctccc     7860 ccatcctacg agtaattgca tttgcttttg taattcttaa tgagcaatat ctgctagaga    7920
gtttagctgt aacagttctt tttgatcatc ttttttttaat aattagaaac accaaaaaaa    7980
tccagaaact tgttcttcca aagcagagag cattataatc accagggcca aaagcttccc    8040
tccctgctgt cattgcttct tctgaggcct gaatccaaaa gaaaacagc cataggccct     8100 ttcagtggcc gggctacccg tgagcccttc ggaggaccag ggctggggca gcctctgggc    8160
ccacatccgg ggccagctcc ggcgtgtgtt cagtgttagc agtgggtcat gatgctcttt    8220
cccacccagc ctgggatagg ggcagaggag gcgaggaggc cgttgccgct gatgtttggc    8280
cgtgaacagg tgggtgtctg cgtgcgtcca cgtgcgtgtt ttctgactga catgaaatcg    8340
acgcccgagt tagcctcacc cggtgacctc tagccctgcc cggatggagc ggggcccacc    8400
cggttcagtg tttctgggga gctggacagt ggagtgcaaa aggcttgcag aacttgaagc    8460
ctgctccttc ccttgctacc acggcctcct ttccgtttga tttgtcactg cttcaatcaa    8520
```

-continued

```
taacagccgc tccagagtca gtagtcaatg aatatatgac caaatatcac caggactgtt    8580
actcaatgtg tgccgagccc ttgcccatgc tgggctcccg tgtatctgga cactgtaacg    8640
tgtgctgtgt ttgctcccct tccccttcct tctttgccct ttacttgtct ttctggggtt    8700
tttctgtttg ggtttggttt ggttttatt tctccttttg tgttccaaac atgaggttct     8760
ctctactggt cctcttaact gtggtgttga ggcttatatt tgtgtaattt ttggtgggtg    8820
aaaggaattt tgctaagtaa atctcttctg tgtttgaact gaagtctgta ttgtaactat    8880
gtttaaagta attgttccag agacaaatat ttctagacac tttttcttta caaacaaaag   8940
cattcggagg gaggggatg gtgactgaga tgagagggga gagctgaaca gatgaccct     9000
gcccagatca gccagaagcc acccaaagca gtggagccca ggagtccac tccaagccag    9060
caagccgaat agctgatgtg ttgccacttt ccaagtcact gcaaaaccag gttttgttcc   9120
gcccagtgga ttcttgtttt gcttcccctc cccccgagat tattaccacc atcccgtgct   9180
tttaaggaaa ggcaagattg atgtttcctt gaggggagcc aggaggggat gtgtgtgtgc   9240
agagctgaag agctggggag aatggggctg ggcccaccca agcaggaggc tgggacgctc   9300
tgctgtgggc acaggtcagg ctaatgttgg cagatgcagc tcttcctgga caggccaggt   9360
ggtgggcatt ctctctccaa ggtgtgcccc gtgggcatta ctgtttaaga cacttccgtc   9420
acatcccacc ccatcctcca gggctcaaca ctgtgacatc tctattcccc accctcccct   9480
tcccagggca ataaaatgac catggagggg gcttgcactc tcttggctgt cacccgatcg   9540
ccagcaaaac ttagatgtga gaaaaccct tcccattcca tggcgaaaac atctccttag    9600
aaaagccatt accctcatta ggcatggttt tgggctccca aaacacctga cagcccctcc   9660
ctcctctgag aggcggagag tgctgactgt agtgaccatt gcatgccggg tgcagcatct   9720
ggaagagcta ggcagggtgt ctgcccctc ctgagttgaa gtcatgctcc cctgtgccag    9780
cccagaggcc gagagctatg gacagcattg ccagtaacac aggccaccct gtgcagaagg   9840
gagctggctc cagcctggaa acctgtctga ggttgggaga ggtgcacttg gggcacaggg   9900
agaggccggg acacacttag ctggagatgt ctctaaaagc cctgtatcgt attcaccttc   9960
agttttgtg ttttgggaca attactttag aaaataagta ggtcgtttta aaaacaaaaa   10020
ttattgattg cttttttgta gtgttcagaa aaaggttct ttgtgtatag ccaaatgact   10080
gaaagcactg atatatttaa aaacaaaagg caatttatta aggaaatttg taccatttca   10140
gtaaacctgt ctgaatgtac ctgtatacgt ttcaaaaaca cccccccccc actgaatccc   10200
tgtaacctat ttattatata aagagtttgc cttataaatt t                      10241
```

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
tatttgatca atccccaggg                                                20

<210> SEQ ID NO 4
<211> LENGTH: 20
<212> TYPE: DNA
<213> ORGANISM: Artificial sequence
<220> FEATURE:
<223> OTHER INFORMATION: Primer

```
<400> SEQUENCE: 4
ctccctctcc cagttaccgt                                                   20

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
aggagagact ggaagaaaag tc                                                22

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
cttgaggggt ttgtccttga                                                   20

<210> SEQ ID NO 7
<211> LENGTH: 23
<212> TYPE: DNA
<213> ORGANISM: Artificial sequence
<220> FEATURE:
<223> OTHER INFORMATION: Primer

<400> SEQUENCE: 7
ctcaccagtt cctgctttga tgt                                               23

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
aggagagact ggaggaaaag tc                                                22

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
cttaaacttc agtggcttgt ctctg                                             25

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
cgggggacat aaaagttatt g                                                 21

<210> SEQ ID NO 11
<211> LENGTH: 22
```

```
<212> TYPE: DNA
<213> ORGANISM: Artificial sequence
<220> FEATURE:
<223> OTHER INFORMATION: Primer

<400> SEQUENCE: 11
tgcattgttt taccagtgtc aa                                              22

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
tgaaggagtc ttctatccga tctgt                                           25

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
cacttccttg acctcgatgc t                                               21

<210> SEQ ID NO 14
<211> LENGTH: 26
<212> TYPE: DNA
<213> ORGANISM: Artificial sequence
<220> FEATURE:
<223> OTHER INFORMATION: Probe

<400> SEQUENCE: 14
agaccgtact ccccatcaag aagcgc                                          26

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gtgcgcgcga gcccgaaatc                                                 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ctctccgaga ggagggagcg                                                 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
```
gccattttcc ggacggcttt                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctctcctcc tcgcctcctc                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19 accccccgccc cccggcaagg                                             20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agagacctca acttgtcacg                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
cattaagata accatcattt                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ggaactggtg agtctgtatt                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gaagcaaggt gtattctggg                                              20

<210> SEQ ID NO 24
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 24
ctaccatgga atcctgttgg                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttttctataa atccatgtat                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tagccccact cccggataag                                                   20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
actcaagccc aaggagttca                                                   20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gctttaatgc tttattttta                                                   20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tgccaacagc aggcccagcg                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gatatcagtg aggaagttgt                                                   20
```

```
<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
cgtgccatgg aagtccttcc                                                    20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggtgagctga tgctatatga                                                    20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
aggcggcagt ggcttacgcc                                                    20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agccccttaa ttttgttctc                                                    20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tggcggctca agaaccagcc                                                    20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
caaatattag aatagactca                                                    20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 37
tgggactcag attctatagg                                              20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gtcctggaac gacaggcttg                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ccaaatttat aacttaagaa                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ggtgatgtgt attttactac                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tggtgggaca aaaattgtgg                                              20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
aaataagcat ctggcatttg                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tacattgaaa aacagccaga                                              20

<210> SEQ ID NO 44
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ggatccatgc gagagaagca                                                    20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tataatatca ttcagcctca                                                    20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cagcaggaag agtccagaga                                                    20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
agaaacctgc caggtgtggt                                                    20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ccaggtgtgg cccagggtgg                                                    20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggcatcctac aacccacaga                                                    20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
``` tgactttct tccctgagcc                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gggtttgtcc ttgaggccct                                             20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
ctcttctttc ttatctttct                                             20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
cttgccctct ttctcttctt                                             20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
tggctgcacg ggctcatgct                                             20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtggtgggct gatggctgca                                             20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ctgctttgcc tgcctctgcg                                             20

<210> SEQ ID NO 57
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 57
aagcttccgg cacagccggg                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggtcacggat gatggagcgc                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ttccgtgtcc agccttcagg                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
cagcagagcg gccagatttc                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
tgtccctgcc ctccctgccc                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gcgaaaggct tttccctggg                                               20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gaagtacgca atcaactcca                                               20
```

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gggatgtgtc gcctaccttt                                          20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cgtgaagtca aaatcattag                                          20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ttaggtggtt tctgctctcg                                          20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
cggcctctgc cagttcctgg                                          20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
acccttttca cctgcacacc                                          20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
aaggagcttc ccaggacttt                                          20

<210> SEQ ID NO 70
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 70
tggcgaagtt tgaaaaggca					20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
agccttgccc cctggcgaag					20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tggatgtggt ggccccaccc					20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gcttttcgct tcctgccggg					20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
gtttcttggg aatggcctga					20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ggctgccacc acactccccg					20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
ttcacggctt tcttttggc					20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ctcctgcaca gatcggatag                                                   20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tctcccgggt cttgcgcttc                                                   20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
cttcaccact tccttgacct                                                   20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
tcagtccttt cccgctcttc                                                   20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
cttgcttttc cgcccagggc                                                   20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
ggtgatggtg gtggtgctcc                                                   20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
gctgctgctc aagtcctggg                                                    20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctccagtgag cctcctctgg                                                    20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
aaccgcgggc tgagtcttag                                                    20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
tggcggcggt ggcaaccgcg                                                    20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ttttctgcgg ccgtggcggc                                                    20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
ctctccctcc cctcggtgtt                                                    20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
cttggcatgg aggatgaaac                                                    20

<210> SEQ ID NO 90
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 90
tccggctgtc cacaggctcc                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
aatccgctcc gtgtaaagtc                                              20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
cagctgcctt tattcttgtt                                              20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gtcagagccc tacccataag                                              20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
agcgcgcgcg ccgccgacgc                                              20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
cttttaccac agccctctct                                              20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
```
ccgctcggcg cggcggcggc                                              20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
tcagtttggg tgattcggtc                                              20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
cagcacagcg ggaacacatt                                              20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
tatttttatg gagcagtctc                                              20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
atgtcacatc aaagcaggaa                                              20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
ttggagctgg tctacagaag                                              20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
agccctaaca tcccagctac                                              20

<210> SEQ ID NO 103
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 103
cacactgacc tttcagggct                                                 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
taaaaaagga tttcctaagt                                                 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
gtacacacac gctttttttt                                                 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
gaaagccgag cctggccggg                                                 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gaagaaaatg tggatttttt                                                 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cgagaatgag actccgtatc                                                 20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
aaacccaaac caccttaccc                                                 20
```

```
<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
aaaataaagt caggaggctg                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
aaaaatggag ggcacagtgg                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112 ggttttctc ctttattatc                                               20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
tatgttggcc tagaactcct                                              20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tgctctcata ttcacccacg                                              20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gtgcagagac tcaagggagg                                              20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 116
gctaagcctc ctggtgaacc                                           20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
gtatgaacat cagctgacgc                                           20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
aggcgcgctg gtgcaagcct                                           20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
cagccactct tttttttga                                            20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
gtacctggga ggaactacaa                                           20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
agggcgagag atccaggact                                           20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
ggattaggga attagatgca                                           20

<210> SEQ ID NO 123

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
ggaaagcctg tcttttaaaa                                               20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
ccagatggtg tttccaattc                                               20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
acttctagac cgggcgcagt                                               20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
gtacaatgaa tgaactttt                                                20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
caaacatatc tactgcattc                                               20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
acaggtaacc ccatctaggc                                               20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
```
ggaggtcctg gtcttctgac                                               20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
ttatctttct tcaccttttt                                               20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
ctctttctct tctttcttat                                               20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
cacgggctca tgcttgccct                                               20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
ggctgatggc tgcacgggct                                               20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tgcgggctca gcagagtggt                                               20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gacccttctg atgtctctgc                                               20

<210> SEQ ID NO 136
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 136
aggcagaagc ttccggcaca                                                   20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
tcatacatgg gtccccggtc                                                   20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
tttcctttgc ttaagcttcc                                                   20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tacacatcat acttcccagc                                                   20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
tcaactccac tttagagcga                                                   20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gcctaccttt tcgaagtacg                                                   20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
ggtccaggga tgtgtcgcct                                                   20
```

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
tccctctccc agttaccgtg                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
tggagctttg ggagatttgg                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
cgtggccgcc ttgggtctcg                                               20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146 aggactttc tccaggaccc                                                20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
aggcatcttg acaaggagct                                               20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148 gcccctggc gaagtttgaa                                                20

<210> SEQ ID NO 149
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 149
ccccaccccc ctcagccttg                                                    20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
ccatgacctg ggtggatgtg                                                    20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
ctgagggtcg gcctcagctt                                                    20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
cccggctttc ggccccgttt                                                    20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
tggcctcggc ggcagcggct                                                    20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
tcggatagaa gactccttca                                                    20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
tacggtctcc tgcacagatc                                                    20

-continued

```
<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
acctcgatgc tgaccgtctc                                                20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
cttctcaccg agggtggaca                                                20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
gggctcttac aggtcttcag                                                20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
ctgctgctgc gccccttggg                                                20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
tcgggctcag gtggaggtgg                                                20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
ctgggcatct tctcctcttt                                                20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 162
gtcttagctg gctccttggg                                               20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ggtggcaacc gcgggctgag                                               20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
cggccgtggc ggcggtggca                                               20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
tgtttgtact tttctgcggc                                               20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
aaacaatgtc tttgcgctct                                               20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
ctcctctctg tttggccttg                                               20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
agtcagctaa ctctctcggt                                               20

<210> SEQ ID NO 169
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 169
tgttggtttg ctttgcaatc                                               20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
taaggagaag agacaacagc                                               20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
ttaatcggga agctttgtca                                               20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
gaggagggag cgcgcgcgcc                                               20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
ccggacggct tttaccacag                                               20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
ctcctcctcc gctcggcgcg                                               20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
```
atgcttcatt tttacagtat                                          20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
gagccagagg ctgggtgcgg                                          20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
tgagtctgta tttttatgga                                          20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
ggagtcacat gtcacatcaa                                          20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
gaatcctgtt ggagctggtc                                          20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
cttccctgag ccctaacatc                                          20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
cccacagcag taaaagagaa                                          20

<210> SEQ ID NO 182
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 182 acccccagtag ttgagattac                                                    20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
atagtagttg ccagagggtg                                                     20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
ggcttctatt gtaaaactat                                                     20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
actggttttt aagagatggg                                                     20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
taaaatctat gggaataaaa                                                     20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
gaaatgtggg cttggcatgg                                                     20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
aacatggttt agtagaaacc                                                     20
```

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
ggtattataa ttttgtaatt                                                 20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
caacattcca tttatttagg                                                 20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
attttcaccc tttaaaaatc                                                 20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
taatacagtg acaagcatcc                                                 20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
tccatcttgc aggtggagta                                                 20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
gaagccaaaa aagcaacaaa                                                 20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 195
ccaagacaag gaaaaacggg                                               20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
ctagctatca gctgggcatg                                               20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
tgccttgttg ggtagtacag                                               20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
gctaagttag aactccgtgg                                               20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
acacgcctgt aatcctgcat                                               20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
caactggagg ccgggcgcga                                               20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
agcccacaca gctgtctcag                                               20

<210> SEQ ID NO 202
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
ttcctcatga atgtgacctg                                                 20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
gaggaacttg tctgagatca                                                 20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
cagctactcg ctagaaaggg                                                 20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
ctccccataa aggagggagg                                                 20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
ccatcataca ctcagatctt                                                 20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
ttgaggccct ggaggtcctg                                                 20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
```
ttctttctta tctttcttca                                               20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
gccctctttc tcttctttct                                               20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
ctgcacgggc tcatgcttgc                                               20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
gtgggctgat ggctgcacgg                                               20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
cctgcctctg cgggctcagc                                               20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
cggagcctga cccttctgat                                               20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
gggaggcaga agcttccggc                                               20

<210> SEQ ID NO 215
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 215
ccagccttca ggcagggtgg                                               20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
cggccagatt tcctttgctt                                               20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
tgatcaaata cacatcatac                                               20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
gtacgcaatc aactccactt                                               20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
tgtgtcgcct accttttcga                                               20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
caaaatcatt agggtccagg                                               20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
tttctgctct cgccgggagg                                               20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
ccagttcctg gagctttggg                                               20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
cacctgcaca ccctctgacg                                               20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
gagcttccca ggactttcct                                               20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
gtttgaaaag gcatcttgac                                               20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
cttgccccct ggcgaagttt                                               20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
tgtggtggcc ccaccccct                                                20

<210> SEQ ID NO 228
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 228
tttgatcacc atgacctggg                                                    20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
ggaatggcct gagggtcggc                                                    20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
ccacactccc cggctttcgg                                                    20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
tttctttttg gcctcggcgg                                                    20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
ctgcacagat cggatagaag                                                    20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
gtcttgcgct tcttgatggg                                                    20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
cttccttgac ctcgatgctg                                                    20

```
<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
ttcccgctct tctcaccgag                                               20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
tccgcccagg gctcttacag                                               20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
tggtggtgct ccttcttggg                                               20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
cggagctctc gggctcaggt                                               20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
agcctcctct gggcatcttc                                               20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
cgggctgagt cttagctggc                                               20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 241
ggcggtggca accgcgggct                              20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
tctgcggccg tggcggcggt                              20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
cccctcggtg tttgtacttt                              20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
ggaggatgaa acaatgtctt                              20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
tccacaggct cctctctgtt                              20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
ccgtgtaaag tcagctaact                              20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
tttattcttg ttggtttgct                              20

<210> SEQ ID NO 248
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 248
cctacccata aggagaagag                                                    20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
tatttcagtt aatcgggaag                                                    20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
acagccctct ctccgagagg                                                    20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
cggcggcggc cattttccgg                                                    20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
tggagcagtc tctcctcctc                                                    20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
ttcatggaat gggcgagaag                                                    20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
```
acagaggcag ggcaggcacg                                                    20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
aagattcatg cttgttagaa                                                    20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
tcaaagcagg aactggtgag                                                    20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
ggtctacaga agcaaggtgt                                                    20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
catcccagct accatggaat                                                    20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
caccatcctg aggccaggca                                                    20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260 taacttttttt ctattattat                                                   20

<210> SEQ ID NO 261
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 261
acagtcacag aacaacaaag                                                     20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
ggcctaattt tttatctttg                                                     20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
acagggttgt agccatcagc                                                     20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gatcactgga acacaatggt                                                     20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
ggaagagaaa agaagggcac                                                     20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
catttaataa ataaatccct                                                     20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
tttaccagtg ccattttttcc                                                    20
```

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cagcaaattt ctgtggtttt                                               20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
gctctcagac cagaccagac                                               20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
acagctgatg aggagggtgg                                               20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
tacacaaata ctaagccaca                                               20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
actgccacca ccatgactaa                                               20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
gttagaagtt gatttttct                                                20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
atactcacat ggtggagaaa                                           20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
gagaagaatg gaagggagaa                                           20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
tagagggttg gaggaacagg                                           20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
cttagaacaa agagaagaat                                           20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
gacactgaca ctgtgcatga                                           20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
ggagttacca tatgacctgg                                           20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
cgtaagcttc tagcaaggag                                           20

<210> SEQ ID NO 281

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
ggtaaaaatg ataaaaaacg                                              20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
agccttctcc tgcctcagct                                              20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
agaagcagca gccacctgcg                                              20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
tggtcttctg acttttcttc                                              20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285 cacctttta aacttgaggg                                               20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
tttctcttct ttcttatctt                                              20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
```
tcatgcttgc cctctttctc          20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
tgatggctgc acgggctcat          20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
cagcagagtg gtgggctgat          20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
tgatgtctct gctttgcctg          20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
cagaagcttc cggcacagcc          20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
gggtccccgg tcacggatga          20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
gcttaagctt ccgtgtccag          20

<210> SEQ ID NO 294
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 294
atacttccca gcagagcggc                                                    20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
agcaaccaaa gagtcaggcc                                                    20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
actttagagc gaaaggcttt                                                    20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
ttttcgaagt acgcaatcaa                                                    20

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
ccagggatgt gtcgcctacc                                                    20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
ccagttaccg tgaagtcaaa                                                    20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
tgggcttctt aggtggtttc                                                    20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
gtggtgccgc tccctttggg                                              20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
tctccaggac cctttcacc                                               20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
gacaaggagc ttcccaggac                                              20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
ccctggcgaa gtttgaaaag                                              20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
cccctcagcc ttgccccctg                                              20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
tgggtggatg tggtggcccc                                              20

<210> SEQ ID NO 307
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 307
cggcctcagc ttttcgcttc                     20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
tcggccccgt ttcttgggaa                     20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
gcggcagcgg ctgccaccac                     20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
aagactcctt cacggctttc                     20

<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
ggtctcctgc acagatcgga                     20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
gctgaccgtc tcccgggtct                     20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
cgagggtgga caccagcagg                     20

```
<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
acaggtcttc agtcctttcc                                              20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
ctgctctcct tgcttttccg                                              20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
ctgagtggtg gtgatggtgg                                              20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
cttctcctct ttgcagacgc                                              20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
ccgtcgctct ccagtgagcc                                              20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
ggcaaccgcg ggctgagtct                                              20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 320
ccgtggcggc ggtggcaacc                                               20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
tacttttctg cggccgtggc                                               20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
tctttgcgct ctccctcccc                                               20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
tgtttggcct tggcatggag                                               20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 324
aactctctcg gtcacgggcg                                               20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
tgctttgcaa tccgctccgt                                               20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
agagacaaca gctgccttta                                               20

<210> SEQ ID NO 327
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 327
gaagctttgt cagagcccta                                          20

<210> SEQ ID NO 328
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 328
ccttccctga aggttccctc cc                                       22
```

COMPOSITIONS AND METHODS FOR MODULATING MECP2 EXPRESSION

STATEMENT OF GOVERNMENT SUPPORT

This invention was made with government support under P30HD024064 and 5R01NS057819 awarded by the National Institutes of Health. The government has certain rights in the invention.

SEQUENCE LISTING

The present application is being filed along with a Sequence Listing in electronic format. The Sequence Listing is provided as a file entitled BIOL0264WOSEQ_ST25.txt created Mar. 2, 2016, which is 180 Kb in size. The information in the electronic format of the sequence listing is incorporated herein by reference in its entirety.

FIELD

Provided are compositions and methods for modulating expression of methyl CpG binding protein 2 (MECP2) mRNA and protein in an animal. Such methods are useful to treat, prevent, or ameliorate neurological disorders, including MECP2 duplication syndrome, by reducing expression and amount of MECP2 mRNA and protein in an animal.

BACKGROUND

Methyl CpG binding protein 2 (MECP2) is located on chromosome Xq28 and plays a fundamental role in epigenetics, controlling chromatin states, and expression of thousands of genes (Chahrour et al., Science, 2008, 320:1224-1229; Nan et al., Nature, 1998, 393:386-389; Jones et al., Nat. Genet., 1998, 19:187-191). MECP2 expression must be maintained within a fairly narrow range to assure proper gene expression and neuronal function (Nan et al., Nature, 1988, 393:386-389). MECP2 duplication syndrome caused by overexpression of MECP2 is characterized by autism, intellectual disability, motor dysfunction, anxiety, epilepsy, recurrent respiratory tract infections, and early death, typically in males (Ramocki et al., Am J Med Genet A, 2010, 152A:1079-1088). Underexpression of MECP2 is associated with Rett Syndrome, which is characterized by normal early growth and development followed by a slowing of development, loss of purposeful use of the hands, distinctive hand movements, slowed brain and head growth, problems with walking, seizures, and intellectual disability, typically in females (Weaving et al., J Med Genet, 2005, 42:1-7).

Currently there is a lack of acceptable options for treating such neurological disorders. It is therefore an object herein to provide compositions and methods for the treatment of such disorders.

SUMMARY

Provided herein are compositions and methods for modulating expression and amount of methyl CpG binding protein 2 (MECP2) mRNA and protein. In certain embodiments, compounds useful for modulating expression and amount of MECP2 mRNA and protein are antisense compounds. In certain embodiments, the antisense compounds are modified antisense oligonucleotides. In certain embodiments, the antisense compounds are single-stranded antisense oligonucleotides. In certain embodiments, the antisense compounds are not siRNA compounds.

In certain embodiments, modulation can occur in a cell or tissue. In certain embodiments, the cell or tissue is in an animal. In certain embodiments, the animal is a human. In certain embodiments, MECP2 mRNA levels are reduced. In certain embodiments, MECP2 protein levels are reduced. Such reduction can occur in a time-dependent manner or in a dose-dependent manner.

Also provided are compositions and methods useful for preventing, treating, and ameliorating disorders and syndromes associated with MECP2 overexpression. In certain embodiments, a disorder associated with MECP2 overexpression is a neurological disorder. In certain embodiments, the neurological disorder is MECP2 duplication syndrome. In certain embodiments, MECP2 duplication syndrome is characterized by having additional copies of MECP2, which leads to overexpression of MECP2.

In certain embodiments, MECP2 duplication syndrome is characterized by autism, intellectual disability, motor dysfunction, anxiety, epilepsy, recurrent respiratory tract infections, and early death. In certain embodiments, MECP2 duplication syndrome is inherited in an X-linked pattern.

In certain embodiments, methods of treatment include administering a MECP2 antisense compound to an individual in need thereof. In certain embodiments, methods of treatment include administering a MECP2 modified antisense oligonucleotide to an individual in need thereof.

In certain embodiments, MECP2 levels are reduced sufficiently to prevent, treat, and ameliorate symptoms of MECP2 duplication syndrome, but not enough to cause symptoms of Rett Syndrome.

BRIEF DESCRIPTION OF THE DRAWINGS

FIG. 1 displays representative EEG traces for WT mice, MECP2-TG1 mice without Isis No. 628785 treatment, and MECP2-TG1 mice that received treatment with Isis No. 628785.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxyethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a syndrome or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" or "inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to an individual in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Hotspot region" is a range of nucleobases on a target nucleic acid amenable to antisense compounds for reducing the amount or activity of the target nucleic acid as demonstrated in the examples hereinbelow.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a MECP2 associated disorder" means identifying an animal having been diagnosed with a MECP2 associated disorder or predisposed to develop a MECP2 associated disorder. Individuals predisposed to develop a MECP2 associated disorder include those having one or more risk factors for developing a MECP2 associated disorder, including, having a personal or family history or genetic predisposition to one or more MECP2 associated disorders. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting MECP2" means reducing the level or expression of a MECP2 mRNA and/or protein. In certain embodiments, MECP2 mRNA and/or protein levels are inhibited in the presence of an antisense compound targeting MECP2, including an antisense oligonucleotide targeting MECP2, as compared to expression of MECP2 mRNA and/or protein levels in the absence of a MECP2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"MECP2 antisense compound" means an antisense compound targeting MECP2.

"MECP2" means the mammalian gene methyl CpG binding protein 2 (MECP2), including the human gene methyl CpG binding protein 2 (MECP2). Human MECP2 has been mapped to human chromosome Xq28.

"MECP2 associated disorder" means any disorder or syndrome associated with any MECP2 nucleic acid or expression product thereof. Such disorders may include a neurological disorder. Such neurological disorders may include MECP2 duplication syndrome.

"MECP2 nucleic acid" means any nucleic acid encoding MECP2. For example, in certain embodiments, a MECP2 nucleic acid includes a DNA sequence encoding MECP2, an RNA sequence transcribed from DNA encoding MECP2 (including genomic DNA comprising introns and exons), and an mRNA sequence encoding MECP2.

"MECP2 mRNA" means any messenger RNA expression product of a DNA sequence encoding MECP2.

"MECP2 protein" means the polypeptide expression product of a MECP2 nucleic acid.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified antisense oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to MECP2 is a pharmaceutical agent.

"Pharmaceutical composition" means a mixture of substances suitable for administering to an individual. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disorder or syndrome for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salt" means a physiologically and pharmaceutically acceptable salt(s) of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded antisense oligonucleotide" means an oligonucleotide which is not hybridized to a complementary strand. A single-stranded antisense oligonucleotide is not a siRNA.

"Sites" as used herein, are defined as unique nucleobase positions within a target nucleic acid.

"Slows progression" means decrease in the development of the disorder or syndrome.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Standard cell assay" means the assay described in Example 1 and reasonable variations thereof.

"Stringent hybridization conditions" or "stringent conditions" refer to conditions under which an oligomeric compound will hybridize to its target sequence, but to a minimal number of other sequences.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds. In certain embodiments, the target nucleic acid is a MECP2 nucleic acid.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disorder or syndrome.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

CERTAIN EMBODIMENTS

Certain embodiments provide methods, compounds, and compositions for inhibiting MECP2 mRNA and protein expression. Certain embodiments provide methods, compounds, and compositions for decreasing MECP2 mRNA and protein levels.

Certain embodiments provide antisense compounds targeted to a MECP2 nucleic acid. In certain embodiments, the MECP2 nucleic acid is the sequence set forth in GENBANK Accession No. NM_004992.3 (incorporated herein as SEQ ID NO: 2) and the complement of GENBANK Accession No. NT_167198.1 truncated from nucleotides 4203000 to U.S. Pat. No. 4,283,000 (incorporated herein as SEQ ID NO: 1).

Certain embodiments provide methods, compounds, and compositions for the treatment, prevention, or amelioration of disorders and syndromes associated with MECP2 in an individual in need thereof. Also contemplated are methods for the preparation of a medicament for the treatment, prevention, or amelioration of a disorder or syndrome associated with MECP2. MECP2 associated disorders and syndromes include neurological disorders. In certain embodiments, MECP2 associated disorders include MECP2 duplication syndrome.

The present disclosure provides the following non-limiting numbered embodiments:

Embodiment 1

A compound, comprising a modified antisense oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 16-327.

Embodiment 2

The compound of embodiment 2, wherein the nucleobase sequence of the modified antisense oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1 or SEQ ID NO: 2.

Embodiment 3

The compound of any preceding embodiment, consisting of a single-stranded modified antisense oligonucleotide.

Embodiment 4

The compound of any preceding embodiment, wherein at least one internucleoside linkage is a modified internucleoside linkage.

Embodiment 5

The compound of embodiment 4, wherein at least one modified internucleoside linkage is a phosphorothioate internucleoside linkage.

Embodiment 6

The compound of embodiment 4, wherein each modified internucleoside linkage is a phosphorothioate internucleoside linkage.

Embodiment 7

The compound of any preceding embodiment, wherein at least one internucleoside linkage is a phosphodiester internucleoside linkage.

Embodiment 8

The compound of any preceding embodiment, wherein at least one internucleoside linkage is a phosphorothioate linkage and at least one internucleoside linkage is a phosphodiester linkage.

Embodiment 9

The compound of any preceding embodiment, wherein at least one nucleoside comprises a modified nucleobase.

Embodiment 10

The compound of embodiment 9, wherein the modified nucleobase is a 5-methylcytosine.

Embodiment 11

The compound of any preceding embodiment, wherein at least one nucleoside of the modified antisense oligonucleotide comprises a modified sugar.

Embodiment 12

The compound of embodiment 11, wherein the at least one modified sugar is a bicyclic sugar.

Embodiment 13

The compound of embodiment 12, wherein the bicyclic sugar comprises a 4'-CH(R)—O-2' bridge wherein R is, independently, H, $C_1$-$C_{12}$ alkyl, or a protecting group.

Embodiment 14

The compound of embodiment 13, wherein R is methyl.

Embodiment 15

The compound of embodiment 13, wherein R is H.

Embodiment 16

The compound of embodiment 11, wherein the at least one modified sugar comprises a 2'-O-methoxyethyl group.

Embodiment 17

The compound of any preceding embodiment, wherein the modified antisense oligonucleotide comprises:

a gap segment consisting of 10 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

Embodiment 18

The compound of any preceding embodiment, wherein the modified antisense oligonucleotide consists of 20 linked nucleosides.

Embodiment 19

A composition comprising the compound of any preceding embodiment or salt thereof and at least one of a pharmaceutically acceptable carrier or diluent.

Embodiment 20

A method comprising administering to an animal the compound or composition of any preceding embodiment.

Embodiment 21

The method of embodiment 20, wherein the animal is a human.

Embodiment 22

The method of embodiment 20, wherein administering the compound prevents, treats, ameliorates, or slows progression of a MECP2 associated disorder or syndrome.

Embodiment 23

The method of embodiment 22, wherein the disease, disorder or condition is MECP2 duplication syndrome.

Embodiment 24

Use of the compound or composition of any preceding embodiment for the manufacture of a medicament for treating a neurological disorder.

Embodiment 25

A method comprising administering a MECP2 antisense compound to an animal for treating a MECP2 associated disorder.

Embodiment 26

A method comprising:
identifying an animal having a MECP2 associated disorder; and
administering a MECP2 antisense compound.

Embodiment 27

The method of embodiment 25 or embodiment 26, wherein MECP2 associated disorder is a neurological disorder.

Embodiment 28

The method of any one of embodiments 25-27, wherein the MECP2 associated disorder is MECP2 duplication syndrome.

Embodiment 29

The method of any one of embodiments 25-28, wherein the animal is a human.

Embodiment 30

The method of any one of embodiments 25-29, wherein the administering is parenteral administration.

Embodiment 31

The method of embodiment 30, wherein the parenteral administration is any of intracerebroventricular administration or intrathecal administration.

Embodiment 32

The method of any one of embodiments 25-31, wherein the administering reduces MECP2 mRNA and or protein levels.

Embodiment 33

The method of embodiment 32, wherein the administering reduces MECP2 mRNA and or protein levels by 15, 20, 25, 30, 35, 40, 45, 50, 55, 60, or 65 percent.

Embodiment 34

The method of any one of embodiments 25-33, wherein the administering improves motor function.

Embodiment 35

The method of embodiment 34, wherein motor function is improved by 10, 15, 20, 25, 30, or 35 percent.

Embodiment 36

The method of any one of embodiments 25-35, wherein the administering improves anxiety.

Embodiment 37

The method of embodiment 36, wherein the administering improves anxiety by 5, 10, 15, 20, 25, 30, 35, 40, 45, or 50 percent.

Embodiment 38

The method of any one of embodiments 25-37, wherein the administering improves social interaction.

Embodiment 39

The method of embodiment 38, wherein the administering improves social interaction by 5, 10, 15, 20, 25, 30, 35, 40, 45, or 50 percent.

Embodiment 40

The method of any one of embodiments 25-39, wherein the administering improves activity.

Embodiment 41

The method of embodiment 40, wherein the administering improves activity by 5, 10, 15, 20, 25, 30, 35, 40, 45, 50, 55, 60, 65, 70, 75, or 80 percent.

Embodiment 42

The method of any one of embodiments 25-41, wherein the administering reduces seizures.

Embodiment 43

The method of any one of embodiments 25-42, wherein the administering normalizes EEG discharges.

Embodiment 44

The method of any one of embodiments 25-43, wherein at least one symptom of a MECP2 associated disorder is ameliorated, treated, prevented, or slowed.

Embodiment 45

The method of any one of embodiments 25-44, wherein the antisense compound is a modified antisense oligonucleotide.

Embodiment 46

The method of embodiment 45, wherein the modified antisense oligonucleotide has the nucleobase sequence of SEQ ID NO: 324, 103, 264, 31, or 112.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a target nucleic acid is 12 to 30 subunits in length. In certain embodiments, an antisense compound targeted to a target nucleic acid is 12 to 25 subunits in length. In certain embodiments, an antisense compound targeted to a target nucleic acid is 12 to 22 subunits in length. In certain embodiments, an antisense compound targeted to a target nucleic acid is 14 to 20 subunits in length. In certain embodiments, an antisense compound targeted to a target nucleic acid is 15 to 25 subunits in length. In certain embodiments, an antisense compound targeted to a target nucleic acid is 18 to 22 subunits in length. In certain embodiments, an antisense compound targeted to a target nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to a target nucleic acid is 12 subunits in length. In certain embodiments, an antisense compound targeted to a target nucleic acid is 13 subunits in length. In certain embodiments, an antisense compound targeted to a target nucleic acid is 14 subunits in length. In certain embodiments, an antisense compound targeted to a target nucleic acid is 15 subunits in length. In certain embodiments, an antisense compound targeted to a target nucleic acid is 16 subunits in length. In certain embodiments, an antisense compound targeted to a target nucleic acid is 17 subunits in length. In certain embodiments, an antisense compound targeted to a target nucleic acid is 18 subunits in length. In certain embodiments, an antisense compound targeted to a target nucleic acid is 19 subunits in length. In certain embodiments, an antisense compound targeted to a target nucleic acid is 20 subunits in length. In certain embodiments, an antisense compound targeted to a target nucleic acid is 21 subunits in length. In certain embodiments, an antisense compound targeted to a target nucleic acid is 22 subunits in length. In certain embodiments, an antisense compound targeted to a target nucleic acid is 23 subunits in length. In certain embodiments, an antisense compound targeted to a target nucleic acid is 24 subunits in length. In certain embodiments, an antisense compound targeted to a target nucleic acid is 25 subunits in length. In certain embodiments, an antisense compound targeted to a target nucleic acid is 26 subunits in length. In certain embodiments, an antisense compound targeted to a target nucleic acid is 27 subunits in length. In certain embodiments, an antisense compound targeted to a target nucleic acid is 28 subunits in length. In certain embodiments, an antisense compound targeted to a target nucleic acid is 29 subunits in length. In certain embodiments, an antisense compound targeted to a target nucleic acid is 30 subunits in length. In certain embodiments, the antisense compound targeted to a target nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to a target nucleic acid may be shortened or truncated. For example, a single subunit may be deleted from the 5' end (5' truncation), or alternatively from the 3' end (3' truncation). A shortened or truncated antisense compound targeted to a target nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a target nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X—Y—Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5. In certain embodiments, gapmers provided herein include, for example 19-mers having a motif of 5-9-5. In certain embodiments, gapmers provided herein include, for example 18-mers having a motif of 5-8-5. In certain embodiments, gapmers provided herein include, for example 18-mers having a motif of 4-8-6. In certain embodiments, gapmers provided herein include, for example 18-mers having a motif of 6-8-4. In certain embodiments, gapmers provided herein include, for example 18-mers having a motif of 5-7-6.

Target Nucleic Acids, Target Regions and Nucleotide Sequences

Nucleotide sequences that encode MECP2 include, without limitation, the following: GENBANK Accession No. NM_004992.3 (incorporated herein as SEQ ID NO: 2) and the complement of GENBANK Accession No. NT_167198.1 truncated from nucleotides 4203000 to U.S. Pat. No. 4,283,000 (incorporated herein as SEQ ID NO: 1).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for MECP2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in MECP2 mRNA levels are indicative of inhibition of MECP2 expression. Reductions in levels of an MECP2 protein are also indicative of inhibition of target mRNA expression. Phenotypic changes are indicative of inhibition of MECP2 expression. Improvement in neurological function is indicative of inhibition of MECP2 expression. Improved motor function, activity, social behavior, and memory are indicative of inhibition of MECP2 expression. Reduction of anxiety-like behaviors is indicative of inhibition of MECP2 expression.

Hybridization

In some embodiments, hybridization occurs between an antisense compound disclosed herein and an MECP2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a MECP2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a MECP2 nucleic acid).

Non-complementary nucleobases between an antisense compound and a target nucleic acid may be tolerated provided that the antisense compound remains able to specifically hybridize to a target nucleic acid. Moreover, an antisense compound may hybridize over one or more segments of a target nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a MECP2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a MECP2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a MECP2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2'

(and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U S. A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the 13-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

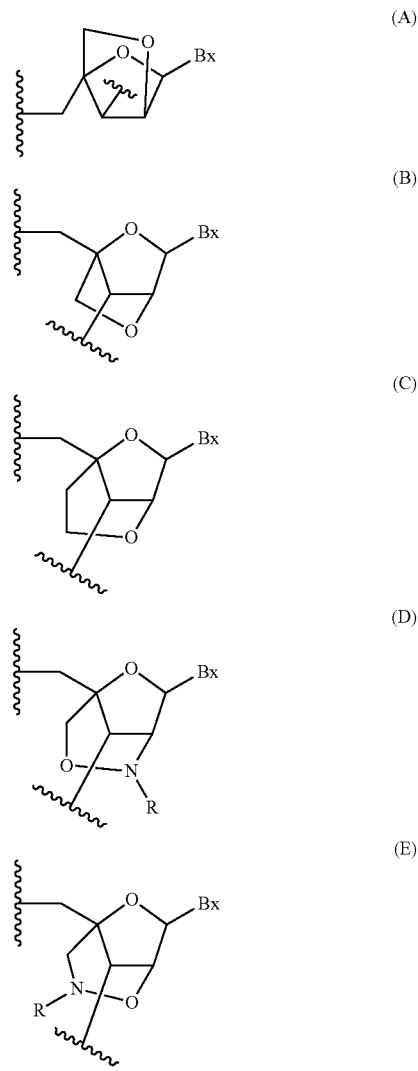

-continued

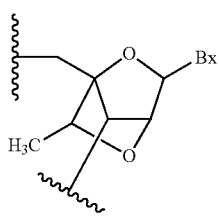
(F)

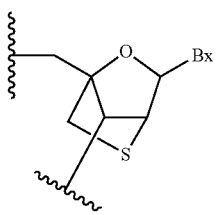
(G)

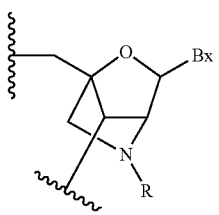
(H)

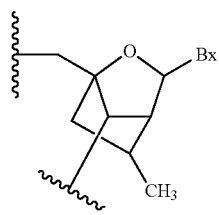
(I)

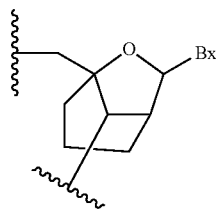
(J)

wherein Bx is the base moiety and R is independently H, a protecting group or $C_1$-$C_{12}$ alkyl.

In certain embodiments, bicyclic nucleosides are provided having Formula I:

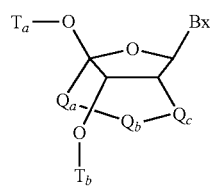
I wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

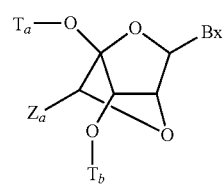
II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

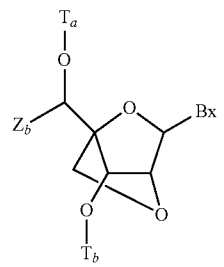
III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

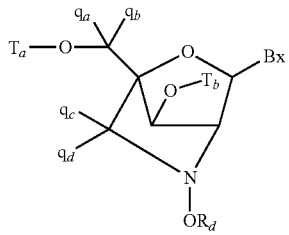

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

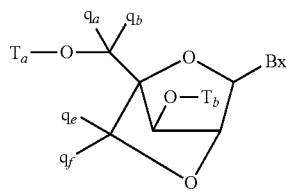

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

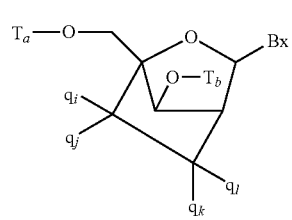

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

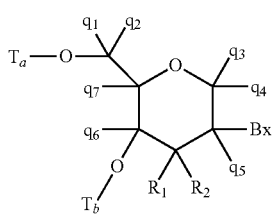

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, $O$—$C_1$-$C_{10}$ alkyl, —$OCF_3$, $O$—$(CH_2)_2$—$O$—$CH_3$, 2'-$O(CH_2)_2SCH_3$, $O$—$(CH_2)_2$—$O$—$N(R_m)(R_n)$, or $O$—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disorder, or dose to be administered.

An antisense compound targeted to a MECP2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a MECP2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of MECP2 nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes. In certain embodiments, cells are patient cells, such as B-lymphoblast cells.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another reagent used to introduce antisense oligonucleotides into cultured cells includes TURBOFECT (Thermo Scientific, Carlsbad, Calif.).

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a MECP2 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900

Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a MECP2 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of MECP2 nucleic acids can be assessed by measuring MECP2 protein levels. Protein levels of MECP2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of MECP2 and produce phenotypic changes, such as, improved behavior, motor function, and cognition. In certain embodiments, motor function is measured by walking initiation analysis, rotarod, grip strength, pole climb, open field performance, balance beam, hindpaw footprint testing in the animal. In certain embodiments, behavior is measured by elevated plus maze and three-chamber social interaction. Testing may be performed in normal animals, or in experimental models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in MECP2 nucleic acid expression are measured.

Certain Indications

In certain embodiments, provided herein are methods of treating an individual comprising administering one or more pharmaceutical compositions described herein. In certain embodiments, the individual has a neurological disorder. In certain embodiments, the individual is at risk for developing a neurological disorder, including, but not limited to, MECP2 duplication syndrome. In certain embodiments, the individual has been identified as having a MECP2 associated disorder. In certain embodiments, provided herein are methods for prophylactically reducing MECP2 expression in an individual. Certain embodiments include treating an individual in need thereof by administering to an individual a therapeutically effective amount of an antisense compound targeted to a MECP2 nucleic acid.

In one embodiment, administration of a therapeutically effective amount of an antisense compound targeted to a MECP2 nucleic acid is accompanied by monitoring of MECP2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a MECP2 nucleic acid results in reduction of MECP2 mRNA and or protein expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved motor function in an animal. In certain embodiments, administration of a MECP2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved anxiety in an animal. In certain embodiments, administration of a MECP2 antisense compound improves anxiety by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved social interaction in an animal. In certain embodiments, administration of a MECP2 antisense compound improves social interaction by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved activity in an animal. In certain embodiments, administration of a MECP2 antisense compound improves activity by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in reduction of seizures. In certain embodiments, administration of a MECP2 antisense compound reduces seizures by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in normalized EEG discharges.

In certain embodiments, pharmaceutical compositions comprising an antisense compound targeted to MECP2 are used for the preparation of a medicament for treating a patient suffering or susceptible to a neurological disorder including MECP2 duplication syndrome.

Certain Amplicon Regions

Certain antisense oligonucleotides described herein may target the amplicon region of the primer probe set. Additional assays may be used to measure the potency and efficacy of these compounds.

Certain Hotspot Regions

1. Nucleobases 28-382, 386-437, 439-464, 478-513, 519-602, 606-716, 720-789, 797-973, 977-1126, 1130-1189, 1192-1275, 1310-1337, 1440-1509, and 1514-1793

In certain embodiments, modified antisense oligonucleotides are complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2. In certain embodiments, nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2 are hotspot regions. In certain embodiments, such modified antisense oligonucleotides are 20 nucleobases in length. In certain embodiments, such modified antisense oligonucleotides are gapmers. In certain such embodiments, the gapmers are 5-10-5 MOE gapmers. In certain embodiments, the nucleosides of the modified antisense oligonucleotides are linked by phosphorothioate and phosphodiester internucleoside linkages.

The nucleobase sequences of SEQ ID Nos: 17, 18, 22-24, 50-60, 62-84, 86-93, 95-96, 99-102, 129-131, 133, 135-158, 161-171, 173-174, 177-180, 207-213, 215-237, 239-244, 246-252, 256-258, 284-288, 290, 292, 293, 296-305, 307-315, and 317-327 are complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2.

In certain embodiments, modified antisense oligonucleotides complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2 achieve at least 25% reduction of MECP2 RNA in vitro in the standard cell assay.

2. Nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785

In certain embodiments, modified antisense oligonucleotides are complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2. In certain embodiments, nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2 are hotspot regions. In certain embodiments, such modified antisense oligonucleotides are 20 nucleobases in length. In certain embodiments, such modified antisense oligonucleotides are gapmers. In certain such embodiments, the gapmers are 5-10-5 MOE gapmers. In certain embodiments, the nucleosides of the modified antisense oligonucleotides are linked by phosphorothioate and phosphodiester internucleoside linkages.

The nucleobase sequences of SEQ ID Nos: 17, 18, 22-24, 50, 52, 54, 58, 63-65, 68-73, 77-79, 81, 83, 88, 90, 91, 93, 100, 102, 133, 137, 141-143, 146, 147, 154-156, 158, 161-163, 165-169, 171, 173, 174, 177-179, 210, 216, 218-220, 223, 224, 226-228, 232-234, 236, 239-242, 244, 246, 247, 251, 257, 258, 284, 287, 288, 292, 293, 298, 303, 307, 310, 311, 314, 315, 317-319, and 321-327 are complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2.

In certain embodiments, modified antisense oligonucleotides complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2 achieve at least 50% reduction of MECP2 RNA in vitro in the standard cell assay.

3. Nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351

In certain embodiments, modified antisense oligonucleotides are complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1. In certain embodiments, nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1 are hotspot regions. In certain embodiments, such modified antisense oligonucleotides are 20 nucleobases in length. In certain embodiments, such modified oligonucleotides are gapmers. In certain such embodiments, the gapmers are 5-10-5 MOE gapmers. In certain embodiments, the nucleosides of the modified oligonucleotides are linked by phosphorothioate and phosphodiester internucleoside linkages.

The nucleobase sequences of SEQ ID Nos: 17, 18, 22-24, 56-60, 62-84, 86-93, 95-96, 100-102, 135-156, 158, 161-171, 173-174, 177-179, 212-213, 215-237, 239-244, 246-251, 256-258, 290-293, 296-305, 307-315, and 317-327 are complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1.

In certain embodiments, modified oligonucleotides complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1 achieve at least 25% reduction of MECP2 RNA in vitro in the standard cell assay.

4. Nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343

In certain embodiments, modified antisense oligonucleotides are complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1. In certain embodiments, nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1 are hotspot regions. In certain embodiments, such modified oligonucleotides are 20 nucleobases in length. In certain embodiments, such modified oligonucleotides are gapmers. In certain such embodiments, the gapmers are 5-10-5 MOE gapmers. In certain embodiments, the nucleosides of the modified oligonucleotides are linked by phosphorothioate and phosphodiester internucleoside linkages.

The nucleobase sequences of SEQ ID Nos: 17, 18, 22-24, 52, 54, 58, 63-65, 68-73, 77-79, 81, 83, 88, 90, 91, 93, 100, 102, 133, 137, 141-143, 146, 147, 154-156, 158, 161-163, 165-169, 171, 173, 174, 177-179, 210, 216, 218-220, 223, 224, 226-228, 232-234, 236, 239, 240-242, 244, 246, 247, 251, 257, 258, 287, 288, 292, 293, 298, 303, 307, 310, 311, 314, 315, 317-319, and 321-327 are complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1.

In certain embodiments, modified antisense oligonucleotides complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1 achieve at least 50% reduction of MECP2 RNA in vitro in the standard cell assay.

EXAMPLES

Non-Limiting Disclosure and Incorporation by Reference

While certain methods described herein have been described with specificity in accordance with certain embodiments, the following examples serve only to illustrate the compounds described herein and are not intended to limit the same. Each of the references recited in the present application is incorporated herein by reference in its entirety.

Example 1: Screening of Antisense Oligonucleotides Targeting MECP2

Antisense oligonucleotides (ASOs) that target human Methyl CpG Binding Protein 2 (MECP2), the complement of GENBANK accession number NT_167198.1 truncated from 4203000 to 4283000, SEQ ID NO: 1, were synthesized using standard solid phase oligonucleotide synthetic methods. They are chimeric oligonucleotides ("gapmers"), composed of a central "gap" region consisting of 2'-deoxynucleotides, which is flanked on both sides (5' and 3') by "wings" that are composed of modified nucleotides. The internucleoside (backbone) linkages are phosphorothioate or phosphodiester throughout the oligonucleotides. The sequences and structures of the antisense oligonucleotides and their start and stop sites along SEQ ID NO: 1 are shown in the tables below. ASOs were designed to target exons and introns along the MECP2 pre-mRNA and some ASOs also target the mRNA. Isis Numbers 628567 (Table 1), 628553 (Table 2), 628566 (Table 3), and 628552 (Table 4) have mismatches to SEQ ID NO: 1 but are 100% complementary to human MECP2 mRNA, GENBANK accession number NM_004992.3 (SEQ ID NO: 2), with start sites of 246, 123, 238, and 115, respectively, on SEQ ID NO: 2. Isis Number 18078 does not target MECP2 and was used as a negative control.

The antisense oligonucleotides were analyzed for their effects on target mRNA levels. HepG2 cells were plated at a density of 20,000 cells per well in 96-well plates and were electroporated with 4.00 μM oligonucleotide or with no oligonucleotide for untreated controls. After approximately 24 hours, RNA was isolated from the cells, and MECP2 mRNA levels were measured by quantitative real-time PCR using primer probe set RTS4253 (forward: 5'-TGAAGGAGTCTTCTATCCGATCTGT-3', SEQ ID NO: 12; reverse: 5'-CACTTCCTTGACCTCGATGCT-3', SEQ ID NO: 13; probe: 5'-AGACCGTACTCCCCAT-CAAGAAGCGC-3', SEQ ID NO: 14). MECP2 mRNA levels were adjusted according to total RNA content, as measured by RIBOGREEN®. Results are presented as average percent inhibition of MECP2 mRNA expression level, relative to untreated control cells, in the tables below. The levels of MECP2 mRNA in untreated control cells (UTC) represents 0% inhibition, and an undetectable level of MECP2 mRNA represents 100% inhibition. A negative inhibition value means that the level of MECP2 mRNA detected was greater than that detected in untreated control cells. The results show that many of the antisense oligonucleotides inhibited MECP2 mRNA levels. The antisense oligonucleotides marked with an asterisk (*) target the region of the primer probe set. Additional assays may be used to measure the potency and efficacy of these antisense oligonucleotides.

TABLE 1

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 18078 | $G_{es}$ $T_{es}$ $G_{es}$ $^mC_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ $^mC_e$ | n/a | n/a | 0.5 | 15 |

TABLE 1-continued

Inhibition of human MECP by antisense oligonucleotides in vitro

| Isis No. | Sequence (5' to 3') | Start site | Stop site | % Inhibition | SEQ ID NO: |
|---|---|---|---|---|---|
| 628543 | $^mC_{es}$ $T_{eo}$ $^mC_{eo}$ $T_{eo}$ $^mC_{eo}$ $^mC_{ds}$ $G_{ds}$ $A_{ds}$ $G_{ds}$ $A_{ds}$ $G_{ds}$ $G_{ds}$ $A_{ds}$ $G_{ds}$ $G_{ds}$ $G_{eo}$ $A_{eo}$ $G_{es}$ $^mC_{es}$ $G_e$ | 1894 | 1913 | -1.7 | 16 |
| 628547 | $G_{es}$ $^mC_{eo}$ $^mC_{eo}$ $A_{eo}$ $T_{eo}$ $T_{ds}$ $T_{ds}$ $T_{ds}$ $^mC_{ds}$ $^mC_{ds}$ $G_{ds}$ $G_{ds}$ $A_{ds}$ $^mC_{ds}$ $G_{ds}$ $G_{eo}$ $^mC_{eo}$ $T_{es}$ $T_{es}$ $T_e$ | 1926 | 1945 | 61.8 | 17 |
| 628551 | $T_{es}$ $^mC_{eo}$ $T_{eo}$ $^mC_{eo}$ $T_{eo}$ $^mC_{ds}$ $^mC_{ds}$ $T_{ds}$ $^mC_{ds}$ $^mC_{ds}$ $T_{ds}$ $^mC_{ds}$ $G_{ds}$ $^mC_{ds}$ $^mC_{ds}$ $T_{eo}$ $^mC_{eo}$ $^mC_{es}$ $T_{es}$ $^mC_e$ | 1981 | 2000 | 54.2 | 18 |
| 628739 | $A_{es}$ $^mC_{eo}$ $^mC_{eo}$ $^mC_{eo}$ $^mC_{eo}$ $^mC_{ds}$ $G_{ds}$ $^mC_{ds}$ $^mC_{ds}$ $^mC_{ds}$ $^mC_{ds}$ $^mC_{ds}$ $G_{ds}$ $G_{ds}$ $^mC_{eo}$ $A_{eo}$ $A_{es}$ $G_{es}$ $G_e$ | 2036 | 2055 | 33.6 | 19 |
| 628743 | $A_{es}$ $G_{eo}$ $A_{eo}$ $G_{eo}$ $A_{eo}$ $^mC_{ds}$ $^mC_{ds}$ $T_{ds}$ $^mC_{ds}$ $A_{ds}$ $A_{ds}$ $^mC_{ds}$ $T_{ds}$ $T_{ds}$ $G_{ds}$ $T_{eo}$ $^mC_{eo}$ $A_{es}$ $^mC_{es}$ $G_e$ | 4053 | 4072 | 36.6 | 20 |
| 628747 | $^mC_{es}$ $A_{eo}$ $T_{eo}$ $T_{eo}$ $A_{eo}$ $A_{ds}$ $G_{ds}$ $A_{ds}$ $T_{ds}$ $A_{ds}$ $A_{ds}$ $^mC_{ds}$ $^mC_{ds}$ $A_{ds}$ $T_{ds}$ $^mC_{eo}$ $A_{eo}$ $T_{es}$ $T_{es}$ $T_e$ | 6590 | 6609 | 43.4 | 21 |
| 628555 | $G_{es}$ $G_{eo}$ $A_{eo}$ $A_{eo}$ $^mC_{eo}$ $T_{ds}$ $G_{ds}$ $G_{ds}$ $T_{ds}$ $G_{ds}$ $A_{ds}$ $G_{ds}$ $T_{ds}$ $^mC_{ds}$ $T_{ds}$ $G_{eo}$ $T_{eo}$ $A_{es}$ $T_{es}$ $T_e$ | 7308 | 7327 | 60.7 | 22 |
| 628559 | $G_{es}$ $A_{eo}$ $A_{eo}$ $G_{eo}$ $^mC_{eo}$ $A_{ds}$ $A_{ds}$ $G_{ds}$ $G_{ds}$ $T_{ds}$ $G_{ds}$ $T_{ds}$ $A_{ds}$ $T_{ds}$ $T_{ds}$ $^mC_{eo}$ $T_{eo}$ $G_{es}$ $G_{es}$ $G_e$ | 7351 | 7370 | 62.7 | 23 |
| 628563 | $^mC_{es}$ $T_{eo}$ $A_{eo}$ $^mC_{eo}$ $^mC_{eo}$ $A_{ds}$ $T_{ds}$ $G_{ds}$ $G_{ds}$ $A_{ds}$ $A_{ds}$ $T_{ds}$ $^mC_{ds}$ $^mC_{ds}$ $T_{ds}$ $G_{eo}$ $T_{eo}$ $T_{es}$ $G_{es}$ $G_e$ | 7383 | 7402 | 63.1 | 24 |
| 628751 | $T_{es}$ $T_{eo}$ $T_{eo}$ $T_{eo}$ $^mC_{eo}$ $T_{ds}$ $A_{ds}$ $T_{ds}$ $A_{ds}$ $A_{ds}$ $A_{ds}$ $T_{ds}$ $^mC_{ds}$ $^mC_{ds}$ $A_{ds}$ $T_{eo}$ $G_{eo}$ $T_{es}$ $A_{es}$ $T_e$ | 9115 | 9134 | 78.3 | 25 |
| 628755 | $T_{es}$ $A_{eo}$ $G_{eo}$ $^mC_{eo}$ $^mC_{eo}$ $^mC_{ds}$ $^mC_{ds}$ $A_{ds}$ $^mC_{ds}$ $T_{ds}$ $^mC_{ds}$ $^mC_{ds}$ $^mC_{ds}$ $G_{ds}$ $G_{ds}$ $A_{eo}$ $T_{eo}$ $A_{es}$ $A_{es}$ $G_e$ | 11509 | 11528 | 62.1 | 26 |
| 628759 | $A_{es}$ $^mC_{eo}$ $T_{eo}$ $^mC_{eo}$ $A_{eo}$ $A_{ds}$ $G_{ds}$ $^mC_{ds}$ $^mC_{ds}$ $^mC_{ds}$ $A_{ds}$ $A_{ds}$ $G_{ds}$ $G_{ds}$ $A_{ds}$ $G_{eo}$ $T_{eo}$ $T_{es}$ $^mC_{es}$ $A_e$ | 14390 | 14409 | 39.1 | 27 |
| 628763 | $G_{es}$ $^mC_{eo}$ $T_{eo}$ $T_{eo}$ $T_{eo}$ $A_{ds}$ $A_{ds}$ $T_{ds}$ $G_{ds}$ $^mC_{ds}$ $T_{ds}$ $T_{ds}$ $T_{ds}$ $A_{ds}$ $T_{ds}$ $T_{eo}$ $T_{eo}$ $T_{es}$ $T_{es}$ $A_e$ | 17349 | 17368 | 89.3 | 28 |
| 628767 | $T_{es}$ $G_{eo}$ $^mC_{eo}$ $^mC_{eo}$ $A_{eo}$ $A_{ds}$ $^mC_{ds}$ $A_{ds}$ $G_{ds}$ $^mC_{ds}$ $A_{ds}$ $G_{ds}$ $G_{ds}$ $^mC_{ds}$ $^mC_{ds}$ $^mC_{eo}$ $A_{eo}$ $G_{es}$ $^mC_{es}$ $G_e$ | 19691 | 19710 | 82.2 | 29 |
| 628771 | $G_{es}$ $A_{eo}$ $T_{eo}$ $A_{eo}$ $T_{eo}$ $^mC_{ds}$ $A_{ds}$ $G_{ds}$ $T_{ds}$ $G_{ds}$ $A_{ds}$ $G_{ds}$ $G_{ds}$ $A_{ds}$ $A_{ds}$ $G_{eo}$ $T_{eo}$ $T_{es}$ $G_{es}$ $T_e$ | 22318 | 22337 | 69.0 | 30 |
| 628775 | $^mC_{es}$ $G_{eo}$ $T_{eo}$ $G_{eo}$ $^mC_{eo}$ $^mC_{ds}$ $A_{ds}$ $T_{ds}$ $G_{ds}$ $G_{ds}$ $A_{ds}$ $A_{ds}$ $G_{ds}$ $T_{ds}$ $^mC_{ds}$ $^mC_{eo}$ $T_{eo}$ $T_{es}$ $^mC_{es}$ $^mC_e$ | 24936 | 24955 | 82.8 | 31 |
| 628779 | $G_{es}$ $G_{eo}$ $T_{eo}$ $G_{eo}$ $A_{eo}$ $G_{ds}$ $^mC_{ds}$ $T_{ds}$ $G_{ds}$ $A_{ds}$ $T_{ds}$ $G_{ds}$ $^mC_{ds}$ $T_{ds}$ $A_{ds}$ $T_{eo}$ $A_{eo}$ $T_{es}$ $G_{es}$ $A_e$ | 27172 | 27191 | 75.8 | 32 |
| 628783 | $A_{es}$ $G_{eo}$ $G_{eo}$ $^mC_{eo}$ $G_{eo}$ $G_{ds}$ $^mC_{ds}$ $A_{ds}$ $G_{ds}$ $T_{ds}$ $G_{ds}$ $G_{ds}$ $G_{ds}$ $^mC_{ds}$ $T_{ds}$ $T_{ds}$ $A_{eo}$ $^mC_{eo}$ $G_{es}$ $^mC_{es}$ $^mC_e$ | 29717 | 29736 | 35.2 | 33 |
| 628787 | $A_{es}$ $G_{eo}$ $^mC_{eo}$ $^mC_{eo}$ $^mC_{eo}$ $^mC_{ds}$ $T_{ds}$ $T_{ds}$ $A_{ds}$ $A_{ds}$ $T_{ds}$ $T_{ds}$ $T_{ds}$ $T_{ds}$ $G_{ds}$ $T_{eo}$ $T_{eo}$ $^mC_{es}$ $T_{es}$ $^mC_e$ | 31758 | 31777 | 81.2 | 34 |
| 628791 | $T_{es}$ $G_{eo}$ $G_{eo}$ $^mC_{eo}$ $G_{eo}$ $G_{ds}$ $^mC_{ds}$ $T_{ds}$ $^mC_{ds}$ $A_{ds}$ $A_{ds}$ $G_{ds}$ $A_{ds}$ $A_{ds}$ $^mC_{ds}$ $^mC_{eo}$ $A_{eo}$ $G_{es}$ $^mC_{es}$ $^mC_e$ | 34273 | 34292 | 39.2 | 35 |
| 628795 | $^mC_{es}$ $A_{eo}$ $A_{eo}$ $A_{eo}$ $T_{eo}$ $A_{ds}$ $T_{ds}$ $T_{ds}$ $A_{ds}$ $G_{ds}$ $A_{ds}$ $A_{ds}$ $T_{ds}$ $A_{ds}$ $G_{ds}$ $A_{eo}$ $^mC_{eo}$ $T_{es}$ $^mC_{es}$ $A_e$ | 36288 | 36307 | 62.8 | 36 |
| 628799 | $T_{es}$ $G_{eo}$ $G_{eo}$ $G_{eo}$ $A_{eo}$ $^mC_{ds}$ $T_{ds}$ $^mC_{ds}$ $A_{ds}$ $G_{ds}$ $A_{ds}$ $T_{ds}$ $T_{ds}$ $^mC_{ds}$ $T_{ds}$ $A_{eo}$ $T_{eo}$ $A_{es}$ $G_{es}$ $G_e$ | 39071 | 39090 | 67.2 | 37 |
| 628803 | $G_{es}$ $T_{eo}$ $^mC_{eo}$ $^mC_{eo}$ $T_{eo}$ $G_{ds}$ $G_{ds}$ $A_{ds}$ $A_{ds}$ $^mC_{ds}$ $G_{ds}$ $A_{ds}$ $^mC_{ds}$ $A_{ds}$ $G_{ds}$ $G_{eo}$ $^mC_{eo}$ $T_{es}$ $T_{es}$ $G_e$ | 41073 | 41092 | 66.0 | 38 |
| 628807 | $^mC_{es}$ $^mC_{eo}$ $A_{eo}$ $A_{eo}$ $A_{eo}$ $T_{ds}$ $T_{ds}$ $T_{ds}$ $A_{ds}$ $T_{ds}$ $A_{ds}$ $A_{ds}$ $^mC_{ds}$ $T_{ds}$ $T_{ds}$ $A_{eo}$ $A_{eo}$ $G_{es}$ $A_{es}$ $A_e$ | 43580 | 43599 | 18.3 | 39 |
| 628811 | $G_{es}$ $G_{eo}$ $T_{eo}$ $G_{eo}$ $A_{eo}$ $T_{ds}$ $G_{ds}$ $T_{ds}$ $G_{ds}$ $T_{ds}$ $A_{ds}$ $T_{ds}$ $T_{ds}$ $T_{ds}$ $T_{ds}$ $A_{eo}$ $^mC_{eo}$ $T_{es}$ $A_{es}$ $^mC_e$ | 45768 | 45787 | 86.2 | 40 |

TABLE 1-continued

Inhibition of human MECP by antisense oligonucleotides in vitro

| Isis No. | Sequence (5' to 3') | Start site | Stop site | % Inhibition | SEQ ID NO: |
|---|---|---|---|---|---|
| 628815 | $T_{es} G_{eo} G_{eo} T_{eo} G_{eo} G_{ds} G_{ds} A_{ds} {}^mC_{ds} A_{ds} A_{ds} A_{ds} A_{ds} A_{ds} T_{ds} T_{eo} G_{eo} T_{es} G_{es} G_e$ | 47850 | 47869 | 64.6 | 41 |
| 628819 | $A_{es} A_{eo} A_{eo} T_{eo} A_{eo} A_{ds} G_{ds} {}^mC_{ds} A_{ds} T_{ds} {}^mC_{ds} T_{ds} G_{ds} G_{ds} {}^mC_{ds} A_{eo} T_{eo} T_{es} T_{es} G_e$ | 49865 | 49884 | 52.8 | 42 |
| 628823 | $T_{es} A_{eo} {}^mC_{eo} A_{eo} T_{eo} T_{ds} G_{ds} A_{ds} A_{ds} A_{ds} A_{ds} A_{ds} {}^mC_{ds} A_{ds} G_{ds} {}^mC_{eo} {}^mC_{eo} A_{es} G_{es} A_e$ | 52552 | 52571 | 17.2 | 43 |
| 628827 | $G_{es} G_{eo} A_{eo} T_{eo} {}^mC_{eo} {}^mC_{ds} A_{ds} T_{ds} G_{ds} {}^mC_{ds} G_{ds} A_{ds} G_{ds} A_{ds} G_{ds} A_{eo} A_{eo} G_{es} {}^mC_{es} A_e$ | 54569 | 54588 | 29.1 | 44 |
| 628831 | $T_{es} A_{eo} T_{eo} A_{eo} A_{eo} T_{ds} A_{ds} T_{ds} {}^mC_{ds} A_{ds} T_{ds} T_{ds} {}^mC_{ds} A_{ds} G_{ds} {}^mC_{eo} {}^mC_{eo} T_{es} {}^mC_{es} A_e$ | 56608 | 56627 | 61.7 | 45 |
| 628835 | ${}^mC_{es} A_{eo} G_{eo} {}^mC_{eo} A_{eo} G_{ds} G_{ds} A_{ds} A_{ds} G_{ds} A_{ds} G_{ds} T_{ds} {}^mC_{ds} {}^mC_{ds} A_{eo} G_{eo} A_{es} G_{es} A_e$ | 59223 | 59242 | 15.9 | 46 |
| 628839 | $A_{es} G_{eo} A_{eo} A_{eo} T_{eo} {}^mC_{ds} {}^mC_{ds} T_{ds} G_{ds} {}^mC_{ds} {}^mC_{ds} A_{ds} G_{ds} G_{ds} T_{ds} G_{eo} T_{eo} G_{es} G_{es} T_e$ | 61278 | 61297 | 64.4 | 47 |
| 628843 | ${}^mC_{es} {}^mC_{eo} A_{eo} G_{eo} G_{eo} T_{ds} G_{ds} T_{ds} G_{ds} G_{ds} {}^mC_{ds} {}^mC_{ds} A_{ds} G_{ds} G_{eo} G_{eo} T_{es} G_{es} G_e$ | 63401 | 63420 | 20.5 | 48 |
| 628847 | $G_{es} G_{eo} {}^mC_{eo} A_{eo} T_{eo} {}^mC_{ds} {}^mC_{ds} T_{ds} A_{ds} {}^mC_{ds} A_{ds} A_{ds} {}^mC_{ds} {}^mC_{ds} {}^mC_{ds} A_{eo} {}^mC_{eo} A_{es} G_{es} A_e$ | 65432 | 65451 | 58.1 | 49 |
| 628567 | $T_{es} G_{eo} A_{eo} {}^mC_{eo} T_{eo} T_{ds} T_{ds} T_{ds} {}^mC_{ds} T_{ds} T_{ds} {}^mC_{ds} {}^mC_{ds} {}^mC_{ds} T_{ds} G_{eo} A_{eo} G_{es} {}^mC_{es} {}^mC_e$ | 67048 | 67067 | 51.8 | 50 |
| 628571 | $G_{es} G_{eo} G_{eo} T_{eo} T_{eo} T_{ds} G_{ds} T_{ds} {}^mC_{ds} {}^mC_{ds} T_{ds} T_{ds} G_{ds} A_{ds} G_{ds} G_{eo} {}^mC_{eo} {}^mC_{es} {}^mC_{es} T_e$ | 67084 | 67103 | 40.4 | 51 |
| 628575 | ${}^mC_{es} T_{eo} {}^mC_{eo} T_{eo} T_{eo} {}^mC_{ds} T_{ds} T_{ds} T_{ds} {}^mC_{ds} T_{ds} T_{ds} A_{ds} T_{ds} {}^mC_{ds} T_{eo} T_{eo} T_{es} {}^mC_{es} T_e$ | 67123 | 67142 | 55.4 | 52 |
| 628579 | ${}^mC_{es} T_{eo} T_{eo} G_{eo} {}^mC_{eo} {}^mC_{ds} {}^mC_{ds} T_{ds} {}^mC_{ds} T_{ds} T_{ds} T_{ds} {}^mC_{ds} T_{ds} {}^mC_{ds} T_{eo} T_{eo} {}^mC_{es} T_{es} T_e$ | 67135 | 67154 | 49.6 | 53 |
| 628583 | $T_{es} G_{eo} G_{eo} {}^mC_{eo} T_{eo} G_{ds} {}^mC_{ds} A_{ds} {}^mC_{ds} G_{ds} G_{ds} G_{ds} {}^mC_{ds} T_{ds} {}^mC_{ds} A_{eo} T_{eo} G_{es} {}^mC_{es} T_e$ | 67153 | 67172 | 57.4 | 54 |
| 628587 | $G_{es} T_{eo} G_{eo} G_{eo} T_{eo} G_{ds} G_{ds} G_{ds} {}^mC_{ds} T_{ds} G_{ds} A_{ds} T_{ds} G_{ds} G_{ds} {}^mC_{eo} T_{eo} G_{es} {}^mC_{es} A_e$ | 67165 | 67184 | 30.9 | 55 |
| 628591 | ${}^mC_{es} T_{eo} G_{eo} {}^mC_{eo} T_{eo} T_{ds} T_{ds} G_{ds} {}^mC_{ds} {}^mC_{ds} T_{ds} G_{ds} {}^mC_{ds} {}^mC_{ds} T_{ds} {}^mC_{eo} T_{eo} G_{es} {}^mC_{es} G_e$ | 67196 | 67215 | 50.0 | 56 |
| 628595 | $A_{es} A_{eo} G_{eo} {}^mC_{eo} T_{eo} T_{ds} {}^mC_{ds} {}^mC_{ds} G_{ds} G_{ds} {}^mC_{ds} A_{ds} {}^mC_{ds} A_{ds} G_{ds} {}^mC_{eo} {}^mC_{eo} G_{es} G_{es} G_e$ | 67241 | 67260 | 47.3 | 57 |
| 628599 | $G_{es} G_{eo} T_{eo} {}^mC_{eo} A_{eo} {}^mC_{ds} G_{ds} G_{ds} A_{ds} T_{ds} G_{ds} A_{ds} T_{ds} G_{ds} G_{ds} A_{eo} G_{eo} {}^mC_{es} G_{es} {}^mC_e$ | 67280 | 67299 | 50.6 | 58 |
| 628603 | $T_{es} T_{eo} {}^mC_{eo} {}^mC_{eo} G_{eo} T_{ds} G_{ds} T_{ds} {}^mC_{ds} {}^mC_{ds} A_{ds} G_{ds} {}^mC_{ds} {}^mC_{ds} T_{ds} T_{eo} {}^mC_{eo} A_{es} G_{es} G_e$ | 67329 | 67348 | 28.8 | 59 |
| *628607 | ${}^mC_{es} A_{eo} G_{eo} {}^mC_{eo} A_{eo} G_{ds} A_{ds} G_{ds} {}^mC_{ds} G_{ds} G_{ds} {}^mC_{ds} {}^mC_{ds} A_{ds} G_{ds} A_{eo} T_{eo} T_{es} T_{es} {}^mC_e$ | 67361 | 67380 | 33.0 | 60 |
| 628851 | $T_{es} G_{eo} T_{eo} {}^mC_{eo} {}^mC_{eo} {}^mC_{ds} T_{ds} G_{ds} {}^mC_{ds} {}^mC_{ds} T_{ds} {}^mC_{ds} {}^mC_{ds} {}^mC_{ds} T_{eo} G_{eo} {}^mC_{es} {}^mC_{es} {}^mC_e$ | 67434 | 67453 | 20.0 | 61 |
| 628611 | $G_{es} {}^mC_{eo} G_{eo} A_{eo} A_{eo} A_{ds} G_{ds} G_{ds} {}^mC_{ds} T_{ds} T_{ds} T_{ds} T_{ds} {}^mC_{ds} {}^mC_{ds} {}^mC_{eo} T_{eo} G_{es} G_{es} G_e$ | 68164 | 68183 | 71.0 | 62 |
| 628615 | $G_{es} A_{eo} A_{eo} G_{eo} T_{eo} A_{ds} {}^mC_{ds} {}^mC_{ds} A_{ds} A_{ds} T_{ds} {}^mC_{ds} A_{ds} A_{ds} {}^mC_{eo} T_{eo} {}^mC_{es} {}^mC_{es} A_e$ | 68191 | 68210 | 65.9 | 63 |
| 628619 | $G_{es} G_{eo} G_{eo} A_{eo} T_{eo} G_{ds} T_{ds} G_{ds} T_{ds} {}^mC_{ds} G_{ds} {}^mC_{ds} {}^mC_{ds} T_{ds} A_{ds} {}^mC_{eo} {}^mC_{eo} T_{es} T_{es} T_e$ | 68213 | 68232 | 62.3 | 64 |

TABLE 1-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628623 | $^mC_{es} G_{eo} T_{eo} G_{eo} A_{eo} A_{ds} G_{ds} T_{ds}\ ^mC_{ds} A_{ds} A_{ds} A_{ds} A_{ds} T_{ds}\ ^mC_{ds} A_{eo} T_{eo} T_{es} A_{es} G_e$ | 68239 | 68258 | 68.7 | 65 |
| 628627 | $T_{es} T_{eo} A_{eo} G_{eo} G_{eo} T_{ds} G_{ds} G_{ds} T_{ds} T_{ds} T_{ds}\ ^mC_{ds} T_{ds} G_{ds}\ ^mC_{ds} T_{eo}\ ^mC_{eo} T_{es}\ ^mC_{es} G_e$ | 68286 | 68305 | 43.0 | 66 |
| 628631 | $^mC_{es} G_{eo} G_{eo}\ ^mC_{eo}\ ^mC_{eo} T_{ds}\ ^mC_{ds} T_{ds} G_{ds}\ ^mC_{ds}\ ^mC_{ds} A_{ds} G_{ds} T_{ds} T_{ds}\ ^mC_{eo}\ ^mC_{eo} T_{es} G_{es} G_e$ | 68328 | 68347 | 36.5 | 67 |
| 628635 | $A_{es}\ ^mC_{eo}\ ^mC_{eo}\ ^mC_{eo} T_{eo} T_{ds} T_{ds} T_{ds}\ ^mC_{ds} A_{ds}\ ^mC_{ds}\ ^mC_{ds} T_{ds} G_{ds}\ ^mC_{ds} A_{eo}\ ^mC_{eo} A_{es}\ ^mC_{es}\ ^mC_e$ | 68400 | 68419 | 53.2 | 68 |
| 628639 | $A_{es} A_{eo} G_{eo} G_{eo} A_{eo} G_{ds}\ ^mC_{ds} T_{ds} T_{ds}\ ^mC_{ds}\ ^mC_{ds}\ ^mC_{ds} A_{ds} G_{ds} G_{ds} A_{eo}\ ^mC_{eo} T_{es} T_{es} T_e$ | 68428 | 68447 | 60.0 | 69 |
| 628643 | $T_{es} G_{eo} G_{eo}\ ^mC_{eo} G_{eo} A_{ds} A_{ds} G_{ds} T_{ds} T_{ds} T_{ds} G_{ds} A_{ds} A_{ds} A_{eo} G_{eo} G_{es}\ ^mC_{es} A_e$ | 68455 | 68474 | 57.8 | 70 |
| 628647 | $A_{es} G_{eo}\ ^mC_{eo}\ ^mC_{eo} T_{eo} T_{ds} G_{ds}\ ^mC_{ds}\ ^mC_{ds}\ ^mC_{ds}\ ^mC_{ds}\ ^mC_{ds} T_{ds} G_{ds} G_{ds}\ ^mC_{eo} G_{eo} A_{es} A_{es} G_e$ | 68467 | 68486 | 59.3 | 71 |
| 628651 | $T_{es} G_{eo} G_{eo} A_{eo} T_{eo} G_{ds} T_{ds} G_{ds} G_{ds} T_{ds} G_{ds} G_{ds}\ ^mC_{ds}\ ^mC_{ds}\ ^mC_{ds}\ ^mC_{eo} A_{eo}\ ^mC_{es}\ ^mC_{es}\ ^mC_e$ | 68492 | 68511 | 50.3 | 72 |
| 628655 | $G_{es}\ ^mC_{eo} T_{eo} T_{eo} T_{eo} T_{ds}\ ^mC_{ds} G_{ds} T_{ds} T_{ds}\ ^mC_{ds}\ ^mC_{ds} T_{ds} G_{ds}\ ^mC_{ds}\ ^mC_{eo} G_{es} G_{es} G_e$ | 68535 | 68554 | 67.2 | 73 |
| 628659 | $G_{es} T_{eo} T_{eo} T_{eo}\ ^mC_{eo} T_{ds} T_{ds} G_{ds} G_{ds} G_{ds} A_{ds} A_{ds} T_{ds} G_{ds} G_{ds}\ ^mC_{eo}\ ^mC_{eo} T_{es} G_{es} A_e$ | 68567 | 68586 | 41.1 | 74 |
| 628663 | $G_{es} G_{eo}\ ^mC_{eo} T_{eo} G_{eo}\ ^mC_{ds}\ ^mC_{ds} A_{ds}\ ^mC_{ds}\ ^mC_{ds} A_{ds}\ ^mC_{ds} A_{ds}\ ^mC_{ds} T_{ds}\ ^mC_{eo}\ ^mC_{eo}\ ^mC_{es}\ ^mC_{es} G_e$ | 68599 | 68618 | 40.4 | 75 |
| *628667 | $T_{es} T_{eo}\ ^mC_{eo} A_{eo}\ ^mC_{eo} G_{ds} G_{ds}\ ^mC_{ds} T_{ds} T_{ds} T_{ds}\ ^mC_{ds} T_{ds} T_{ds} T_{ds} T_{eo} T_{eo} G_{es} G_{es}\ ^mC_e$ | 68631 | 68650 | 38.2 | 76 |
| *628671 | $^mC_{es} T_{eo}\ ^mC_{eo}\ ^mC_{eo} T_{eo} G_{ds}\ ^mC_{ds} A_{ds}\ ^mC_{ds} A_{ds} G_{ds} A_{ds} T_{ds}\ ^mC_{ds} G_{ds} G_{eo} A_{eo} T_{es} A_{es} G_e$ | 68659 | 68678 | 76.9 | 77 |
| *628675 | $T_{es}\ ^mC_{eo} T_{eo}\ ^mC_{eo}\ ^mC_{eo}\ ^mC_{ds} G_{ds} G_{ds} G_{ds} T_{ds}\ ^mC_{ds} T_{ds} T_{ds} G_{ds}\ ^mC_{ds} G_{eo}\ ^mC_{eo} T_{es} T_{es}\ ^mC_e$ | 68696 | 68715 | 85.3 | 78 |
| *628679 | $^mC_{es} T_{eo} T_{eo}\ ^mC_{eo} A_{eo}\ ^mC_{ds}\ ^mC_{ds} A_{ds}\ ^mC_{ds} T_{ds} T_{ds}\ ^mC_{ds}\ ^mC_{ds} T_{ds} T_{ds} G_{eo} A_{eo}\ ^mC_{es}\ ^mC_{es} T_e$ | 68728 | 68747 | 74.5 | 79 |
| 628683 | $T_{es}\ ^mC_{eo} A_{eo} G_{eo} T_{eo}\ ^mC_{ds}\ ^mC_{ds} T_{ds} T_{ds} T_{ds}\ ^mC_{ds}\ ^mC_{ds}\ ^mC_{ds} G_{ds}\ ^mC_{ds} T_{eo}\ ^mC_{eo} T_{es} T_{es}\ ^mC_e$ | 68774 | 68793 | 43.0 | 80 |
| 628687 | $^mC_{es} T_{eo} T_{eo} G_{eo}\ ^mC_{eo} T_{ds} T_{ds} T_{ds} T_{ds}\ ^mC_{ds}\ ^mC_{ds} G_{ds}\ ^mC_{ds}\ ^mC_{ds} A_{eo} G_{eo} G_{es} G_{es}\ ^mC_e$ | 68806 | 68825 | 69.2 | 81 |
| 628691 | $G_{es} G_{eo} T_{eo} G_{eo} A_{eo} T_{ds} G_{ds} G_{ds} T_{ds} G_{ds} G_{ds} T_{ds} G_{ds} G_{ds} T_{ds} G_{eo}\ ^mC_{eo} T_{es}\ ^mC_{es}\ ^mC_e$ | 68876 | 68895 | 49.4 | 82 |
| 628695 | $G_{es}\ ^mC_{eo} T_{eo} G_{eo}\ ^mC_{eo} T_{ds} G_{ds}\ ^mC_{ds} T_{ds}\ ^mC_{ds} A_{ds} A_{ds} G_{ds} T_{ds}\ ^mC_{ds}\ ^mC_{eo} T_{eo} G_{es} G_{es} G_e$ | 68998 | 69017 | 62.3 | 83 |
| 628699 | $^mC_{es} T_{eo}\ ^mC_{eo}\ ^mC_{eo} A_{eo} G_{ds} T_{ds} G_{ds} A_{ds} G_{ds}\ ^mC_{ds}\ ^mC_{ds} T_{ds}\ ^mC_{ds}\ ^mC_{ds} T_{eo}\ ^mC_{eo} T_{es} G_{es} G_e$ | 69040 | 69059 | 45.7 | 84 |
| 628703 | $A_{es} A_{eo}\ ^mC_{eo}\ ^mC_{eo} G_{eo}\ ^mC_{ds} G_{ds} G_{ds} G_{ds}\ ^mC_{ds} T_{ds} G_{ds} A_{ds} G_{ds} T_{ds}\ ^mC_{eo} T_{eo} T_{es} A_{es} G_e$ | 69085 | 69104 | 23.7 | 85 |
| 628707 | $T_{es} G_{eo} G_{eo}\ ^mC_{eo} G_{eo} G_{ds}\ ^mC_{ds} G_{ds} G_{ds} T_{ds} G_{ds} G_{ds}\ ^mC_{ds} A_{ds} A_{ds}\ ^mC_{eo}\ ^mC_{eo} G_{es}\ ^mC_{es} G_e$ | 69098 | 69117 | 43.7 | 86 |
| 628711 | $T_{es} T_{eo} T_{eo} T_{eo}\ ^mC_{eo} T_{ds} G_{ds}\ ^mC_{ds} G_{ds} G_{ds}\ ^mC_{ds} G_{ds} T_{ds} G_{ds} G_{eo}\ ^mC_{eo} G_{es} G_{es}\ ^mC_e$ | 69111 | 69130 | 44.4 | 87 |
| 628715 | $^mC_{es} T_{eo}\ ^mC_{eo} T_{eo}\ ^mC_{eo}\ ^mC_{ds}\ ^mC_{ds} T_{ds}\ ^mC_{ds}\ ^mC_{ds} T_{ds}\ ^mC_{ds} G_{ds} G_{eo} T_{eo} G_{es} T_{es} T_e$ | 69136 | 69155 | 54.7 | 88 |

TABLE 1-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628719 | $^mC_{es}$ $T_{eo}$ $T_{eo}$ $G_{eo}$ $G_{eo}$ $^mC_{ds}$ $A_{ds}$ $T_{ds}$ $G_{ds}$ $G_{ds}$ $A_{ds}$ $G_{ds}$ $G_{ds}$ $A_{ds}$ $T_{ds}$ $G_{eo}$ $A_{eo}$ $A_{es}$ $A_{es}$ $^mC_e$ | 69168 | 69187 | 41.5 | 89 |
| 628723 | $T_{es}$ $^mC_{eo}$ $^mC_{eo}$ $G_{eo}$ $G_{eo}$ $^mC_{ds}$ $T_{ds}$ $G_{ds}$ $T_{ds}$ $^mC_{ds}$ $^mC_{ds}$ $A_{ds}$ $^mC_{ds}$ $A_{ds}$ $G_{ds}$ $G_{eo}$ $^mC_{eo}$ $T_{es}$ $^mC_{es}$ $^mC_e$ | 69200 | 69219 | 59.6 | 90 |
| 628727 | $A_{es}$ $A_{eo}$ $T_{eo}$ $^mC_{eo}$ $^mC_{eo}$ $G_{ds}$ $^mC_{ds}$ $^mC_{ds}$ $^mC_{ds}$ $G_{ds}$ $T_{ds}$ $G_{ds}$ $T_{ds}$ $A_{ds}$ $A_{eo}$ $A_{eo}$ $G_{es}$ $T_{es}$ $^mC_e$ | 69244 | 69263 | 50.4 | 91 |
| 628731 | $^mC_{es}$ $A_{eo}$ $G_{eo}$ $^mC_{eo}$ $T_{eo}$ $G_{ds}$ $^mC_{ds}$ $^mC_{ds}$ $T_{ds}$ $T_{ds}$ $T_{ds}$ $A_{ds}$ $T_{ds}$ $T_{ds}$ $^mC_{ds}$ $T_{eo}$ $T_{eo}$ $G_{es}$ $T_{es}$ $T_e$ | 69276 | 69295 | 43.3 | 92 |
| 628735 | $G_{es}$ $T_{eo}$ $^mC_{eo}$ $A_{eo}$ $G_{eo}$ $A_{ds}$ $G_{ds}$ $^mC_{ds}$ $^mC_{ds}$ $T_{ds}$ $A_{ds}$ $^mC_{ds}$ $^mC_{ds}$ $^mC_{ds}$ $A_{eo}$ $T_{eo}$ $A_{es}$ $A_{es}$ $G_e$ | 69308 | 69327 | 70.7 | 93 |

Superscript "m" indicates 5-methylcytosine.
Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 2

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 18078 | $G_{es}$ $T_{es}$ $G_{es}$ $^mC_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ $^mC_e$ | n/a | n/a | 3.8 | 15 |
| 628541 | $A_{es}$ $G_{eo}$ $^mC_{eo}$ $G_{eo}$ $^mC_{eo}$ $G_{ds}$ $^mC_{ds}$ $G_{ds}$ $^mC_{ds}$ $G_{ds}$ $^mC_{ds}$ $^mC_{ds}$ $G_{ds}$ $^mC_{ds}$ $^mC_{ds}$ $G_{eo}$ $A_{eo}$ $^mC_{es}$ $G_{es}$ $^mC_e$ | 1878 | 1897 | 15.3 | 94 |
| 628545 | $^mC_{es}$ $T_{eo}$ $T_{eo}$ $T_{eo}$ $T_{eo}$ $A_{ds}$ $^mC_{ds}$ $^mC_{ds}$ $A_{ds}$ $^mC_{ds}$ $A_{ds}$ $G_{ds}$ $^mC_{ds}$ $^mC_{ds}$ $T_{eo}$ $^mC_{eo}$ $T_{es}$ $^mC_{es}$ $T_e$ | 1910 | 1929 | 48.4 | 95 |
| 628549 | $^mC_{es}$ $^mC_{eo}$ $G_{eo}$ $^mC_{eo}$ $T_{eo}$ $^mC_{ds}$ $G_{ds}$ $G_{ds}$ $^mC_{ds}$ $G_{ds}$ $^mC_{ds}$ $G_{ds}$ $G_{ds}$ $^mC_{ds}$ $G_{ds}$ $G_{eo}$ $^mC_{eo}$ $G_{es}$ $G_{es}$ $^mC_e$ | 1953 | 1972 | 32.9 | 96 |
| 628741 | $T_{es}$ $^mC_{eo}$ $A_{eo}$ $G_{eo}$ $T_{eo}$ $T_{ds}$ $T_{ds}$ $G_{ds}$ $G_{ds}$ $G_{ds}$ $T_{ds}$ $G_{ds}$ $A_{ds}$ $T_{ds}$ $T_{ds}$ $^mC_{eo}$ $G_{eo}$ $G_{es}$ $T_{es}$ $^mC_e$ | 3047 | 3066 | 45.7 | 97 |
| 628745 | $^mC_{es}$ $A_{eo}$ $G_{eo}$ $^mC_{eo}$ $A_{eo}$ $^mC_{ds}$ $A_{ds}$ $G_{ds}$ $^mC_{ds}$ $G_{ds}$ $G_{ds}$ $G_{ds}$ $A_{ds}$ $A_{ds}$ $^mC_{ds}$ $A_{eo}$ $^mC_{eo}$ $A_{es}$ $T_{es}$ $T_e$ | 5561 | 5580 | 42.2 | 98 |
| 628553 | $T_{es}$ $A_{eo}$ $T_{eo}$ $T_{eo}$ $T_{eo}$ $T_{ds}$ $T_{ds}$ $A_{ds}$ $T_{ds}$ $G_{ds}$ $G_{ds}$ $A_{ds}$ $G_{ds}$ $^mC_{ds}$ $A_{ds}$ $G_{eo}$ $T_{eo}$ $^mC_{es}$ $T_{es}$ $^mC_e$ | 7292 | 7311 | 36.6 | 99 |
| 628557 | $A_{es}$ $T_{eo}$ $G_{eo}$ $T_{eo}$ $^mC_{eo}$ $A_{ds}$ $^mC_{ds}$ $A_{ds}$ $T_{ds}$ $^mC_{ds}$ $A_{ds}$ $A_{ds}$ $A_{ds}$ $G_{ds}$ $^mC_{ds}$ $A_{eo}$ $G_{eo}$ $G_{es}$ $A_{es}$ $A_e$ | 7324 | 7343 | 70.2 | 100 |
| 628561 | $T_{es}$ $T_{eo}$ $G_{eo}$ $G_{eo}$ $A_{eo}$ $G_{ds}$ $^mC_{ds}$ $T_{ds}$ $G_{ds}$ $G_{ds}$ $T_{ds}$ $^mC_{ds}$ $T_{ds}$ $A_{ds}$ $^mC_{ds}$ $A_{eo}$ $G_{eo}$ $A_{es}$ $A_{es}$ $G_e$ | 7367 | 7386 | 43.4 | 101 |
| 628565 | $A_{es}$ $G_{eo}$ $^mC_{eo}$ $^mC_{eo}$ $^mC_{eo}$ $T_{ds}$ $A_{ds}$ $A_{ds}$ $^mC_{ds}$ $A_{ds}$ $T_{ds}$ $^mC_{ds}$ $^mC_{ds}$ $^mC_{ds}$ $A_{ds}$ $G_{eo}$ $^mC_{eo}$ $T_{es}$ $A_{es}$ $^mC_e$ | 7399 | 7418 | 72.5 | 102 |
| 628749 | $^mC_{es}$ $A_{eo}$ $^mC_{eo}$ $A_{eo}$ $^mC_{eo}$ $T_{ds}$ $G_{ds}$ $A_{ds}$ $^mC_{ds}$ $^mC_{ds}$ $T_{ds}$ $T_{ds}$ $T_{ds}$ $^mC_{ds}$ $A_{ds}$ $G_{eo}$ $G_{eo}$ $G_{es}$ $^mC_{es}$ $T_e$ | 7615 | 7634 | 96.4 | 103 |
| 628753 | $T_{es}$ $A_{eo}$ $A_{eo}$ $A_{eo}$ $A_{eo}$ $A_{ds}$ $A_{ds}$ $G_{ds}$ $G_{ds}$ $A_{ds}$ $T_{ds}$ $T_{ds}$ $T_{ds}$ $^mC_{ds}$ $^mC_{ds}$ $T_{eo}$ $A_{eo}$ $A_{es}$ $G_{es}$ $T_e$ | 10408 | 10427 | 12.3 | 104 |
| 628757 | $G_{es}$ $T_{eo}$ $A_{eo}$ $^mC_{eo}$ $A_{eo}$ $^mC_{ds}$ $A_{ds}$ $^mC_{ds}$ $A_{ds}$ $^mC_{ds}$ $G_{ds}$ $^mC_{ds}$ $T_{ds}$ $T_{ds}$ $T_{ds}$ $T_{eo}$ $T_{eo}$ $T_{es}$ $T_{es}$ $T_e$ | 13332 | 13351 | 85.5 | 105 |
| 628761 | $G_{es}$ $A_{eo}$ $A_{eo}$ $A_{eo}$ $G_{eo}$ $^mC_{ds}$ $^mC_{ds}$ $G_{ds}$ $A_{ds}$ $G_{ds}$ $^mC_{ds}$ $^mC_{ds}$ $T_{ds}$ $G_{ds}$ $G_{ds}$ $^mC_{eo}$ $^mC_{eo}$ $G_{es}$ $G_{es}$ $G_e$ | 15686 | 15705 | 51.4 | 106 |
| 628765 | $G_{es}$ $A_{eo}$ $A_{eo}$ $G_{eo}$ $A_{eo}$ $A_{ds}$ $A_{ds}$ $A_{ds}$ $T_{ds}$ $G_{ds}$ $T_{ds}$ $G_{ds}$ $G_{ds}$ $A_{ds}$ $T_{ds}$ $T_{eo}$ $T_{eo}$ $T_{es}$ $T_{es}$ $T_e$ | 18630 | 18649 | 78.3 | 107 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628769 | $^mC_{es}$ $G_{eo}$ $A_{eo}$ $G_{eo}$ $A_{eo}$ $A_{ds}$ $T_{ds}$ $G_{ds}$ $A_{ds}$ $G_{ds}$ $A_{ds}$ $^mC_{ds}$ $T_{ds}$ $^mC_{ds}$ $^mC_{ds}$ $G_{eo}$ $T_{eo}$ $A_{es}$ $T_{es}$ $^mC_e$ | 21317 | 21336 | 63.6 | 108 |
| 628773 | $A_{es}$ $A_{eo}$ $A_{eo}$ $^mC_{eo}$ $^mC_{eo}$ $^mC_{ds}$ $A_{ds}$ $A_{ds}$ $A_{ds}$ $^mC_{ds}$ $^mC_{ds}$ $A_{ds}$ $^mC_{ds}$ $^mC_{ds}$ $T_{ds}$ $T_{eo}$ $A_{eo}$ $^mC_{es}$ $^mC_{es}$ $^mC_e$ | 23339 | 23358 | 48.9 | 109 |
| 628777 | $A_{es}$ $A_{eo}$ $A_{eo}$ $A_{eo}$ $T_{eo}$ $A_{ds}$ $A_{ds}$ $A_{ds}$ $G_{ds}$ $T_{ds}$ $^mC_{ds}$ $A_{ds}$ $G_{ds}$ $G_{ds}$ $A_{ds}$ $G_{eo}$ $G_{eo}$ $^mC_{es}$ $T_{es}$ $G_e$ | 26037 | 26056 | 65.5 | 110 |
| 628781 | $A_{es}$ $A_{eo}$ $A_{eo}$ $A_{eo}$ $A_{eo}$ $T_{ds}$ $G_{ds}$ $G_{ds}$ $A_{ds}$ $G_{ds}$ $G_{ds}$ $G_{ds}$ $^mC_{ds}$ $A_{ds}$ $^mC_{ds}$ $A_{eo}$ $G_{eo}$ $T_{es}$ $G_{es}$ $G_e$ | 28177 | 28196 | 12.2 | 111 |
| 628785 | $G_{es}$ $G_{eo}$ $T_{eo}$ $T_{eo}$ $T_{eo}$ $T_{ds}$ $T_{ds}$ $^mC_{ds}$ $T_{ds}$ $^mC_{ds}$ $^mC_{ds}$ $T_{ds}$ $T_{ds}$ $T_{ds}$ $A_{ds}$ $T_{eo}$ $T_{eo}$ $A_{es}$ $T_{es}$ $^mC_e$ | 30744 | 30763 | 92.2 | 112 |
| 628789 | $T_{es}$ $A_{eo}$ $T_{eo}$ $G_{eo}$ $T_{eo}$ $T_{ds}$ $G_{ds}$ $G_{ds}$ $^mC_{ds}$ $^mC_{ds}$ $T_{ds}$ $A_{ds}$ $G_{ds}$ $A_{ds}$ $A_{ds}$ $^mC_{eo}$ $T_{eo}$ $^mC_{es}$ $^mC_{es}$ $T_e$ | 33273 | 33292 | 52.4 | 113 |
| 628793 | $T_{es}$ $G_{eo}$ $^mC_{eo}$ $T_{eo}$ $^mC_{eo}$ $T_{ds}$ $^mC_{ds}$ $A_{ds}$ $T_{ds}$ $A_{ds}$ $T_{ds}$ $T_{ds}$ $^mC_{ds}$ $A_{ds}$ $^mC_{ds}$ $^mC_{eo}$ $^mC_{eo}$ $A_{es}$ $^mC_{es}$ $G_e$ | 35287 | 35306 | 79.3 | 114 |
| 628797 | $G_{es}$ $T_{eo}$ $G_{eo}$ $^mC_{eo}$ $A_{eo}$ $G_{ds}$ $A_{ds}$ $G_{ds}$ $A_{ds}$ $^mC_{ds}$ $T_{ds}$ $^mC_{ds}$ $A_{ds}$ $A_{ds}$ $G_{ds}$ $G_{eo}$ $G_{eo}$ $A_{es}$ $G_{es}$ $G_e$ | 38049 | 38068 | 21.7 | 115 |
| 628801 | $G_{es}$ $^mC_{eo}$ $T_{eo}$ $A_{eo}$ $A_{eo}$ $G_{ds}$ $^mC_{ds}$ $^mC_{ds}$ $T_{ds}$ $^mC_{ds}$ $^mC_{ds}$ $T_{ds}$ $G_{ds}$ $G_{ds}$ $T_{ds}$ $G_{eo}$ $A_{eo}$ $A_{es}$ $^mC_{es}$ $^mC_e$ | 40072 | 40091 | 65.0 | 116 |
| 628805 | $G_{es}$ $T_{eo}$ $A_{eo}$ $T_{eo}$ $G_{eo}$ $A_{ds}$ $A_{ds}$ $^mC_{ds}$ $A_{ds}$ $A_{ds}$ $^mC_{ds}$ $A_{ds}$ $G_{ds}$ $^mC_{ds}$ $T_{ds}$ $G_{eo}$ $A_{eo}$ $^mC_{es}$ $G_{es}$ $^mC_e$ | 42580 | 42599 | 69.6 | 117 |
| 628809 | $A_{es}$ $G_{eo}$ $G_{eo}$ $^mC_{eo}$ $G_{eo}$ $^mC_{ds}$ $G_{ds}$ $^mC_{ds}$ $T_{ds}$ $G_{ds}$ $G_{ds}$ $T_{ds}$ $G_{ds}$ $^mC_{ds}$ $A_{ds}$ $A_{eo}$ $G_{eo}$ $^mC_{es}$ $^mC_{es}$ $T_e$ | 44735 | 44754 | 16.5 | 118 |
| 628813 | $^mC_{es}$ $A_{eo}$ $G_{eo}$ $^mC_{eo}$ $^mC_{eo}$ $A_{ds}$ $^mC_{ds}$ $T_{ds}$ $^mC_{ds}$ $T_{ds}$ $T_{ds}$ $T_{ds}$ $T_{ds}$ $T_{ds}$ $T_{ds}$ $T_{eo}$ $T_{eo}$ $T_{es}$ $G_{es}$ $A_e$ | 46834 | 46853 | 59.1 | 119 |
| 628817 | $G_{es}$ $T_{eo}$ $A_{eo}$ $^mC_{eo}$ $^mC_{eo}$ $T_{ds}$ $G_{ds}$ $G_{ds}$ $G_{ds}$ $A_{ds}$ $G_{ds}$ $G_{ds}$ $A_{ds}$ $A_{ds}$ $^mC_{ds}$ $T_{eo}$ $A_{eo}$ $^mC_{es}$ $A_{es}$ $A_e$ | 48863 | 48882 | 68.0 | 120 |
| 628821 | $A_{es}$ $G_{eo}$ $G_{eo}$ $G_{eo}$ $^mC_{eo}$ $G_{ds}$ $A_{ds}$ $G_{ds}$ $A_{ds}$ $G_{ds}$ $A_{ds}$ $T_{ds}$ $^mC_{ds}$ $^mC_{ds}$ $A_{ds}$ $G_{eo}$ $G_{eo}$ $A_{es}$ $^mC_{es}$ $T_e$ | 50865 | 50884 | 80.7 | 121 |
| 628825 | $G_{es}$ $G_{eo}$ $A_{eo}$ $T_{eo}$ $T_{eo}$ $A_{ds}$ $G_{ds}$ $G_{ds}$ $G_{ds}$ $A_{ds}$ $A_{ds}$ $T_{ds}$ $T_{ds}$ $A_{ds}$ $G_{ds}$ $A_{eo}$ $T_{eo}$ $G_{es}$ $^mC_{es}$ $A_e$ | 53552 | 53571 | 59.3 | 122 |
| 628829 | $G_{es}$ $G_{eo}$ $A_{eo}$ $A_{eo}$ $A_{eo}$ $G_{ds}$ $^mC_{ds}$ $^mC_{ds}$ $T_{ds}$ $G_{ds}$ $T_{ds}$ $^mC_{ds}$ $T_{ds}$ $T_{ds}$ $T_{ds}$ $T_{eo}$ $A_{eo}$ $A_{es}$ $A_{es}$ $A_e$ | 55596 | 55615 | 54.0 | 123 |
| 628833 | $^mC_{es}$ $^mC_{eo}$ $A_{eo}$ $G_{eo}$ $A_{eo}$ $T_{ds}$ $G_{ds}$ $G_{ds}$ $T_{ds}$ $G_{ds}$ $T_{ds}$ $T_{ds}$ $T_{ds}$ $^mC_{ds}$ $^mC_{ds}$ $A_{eo}$ $A_{eo}$ $T_{es}$ $T_{es}$ $^mC_e$ | 57622 | 57641 | 85.3 | 124 |
| 628837 | $A_{es}$ $^mC_{eo}$ $T_{eo}$ $T_{eo}$ $^mC_{eo}$ $T_{ds}$ $A_{ds}$ $G_{ds}$ $A_{ds}$ $^mC_{ds}$ $^mC_{ds}$ $G_{ds}$ $G_{ds}$ $G_{ds}$ $^mC_{ds}$ $G_{eo}$ $^mC_{eo}$ $A_{es}$ $G_{es}$ $T_e$ | 60266 | 60285 | 48.3 | 125 |
| 628841 | $G_{es}$ $T_{eo}$ $A_{eo}$ $^mC_{eo}$ $A_{eo}$ $A_{ds}$ $T_{ds}$ $G_{ds}$ $A_{ds}$ $A_{ds}$ $T_{ds}$ $G_{ds}$ $A_{ds}$ $A_{ds}$ $^mC_{ds}$ $T_{eo}$ $T_{eo}$ $T_{es}$ $T_{es}$ $T_e$ | 62361 | 62380 | 69.7 | 126 |
| 628845 | $^mC_{es}$ $A_{eo}$ $A_{eo}$ $A_{eo}$ $^mC_{eo}$ $A_{ds}$ $T_{ds}$ $A_{ds}$ $T_{ds}$ $^mC_{ds}$ $T_{ds}$ $A_{ds}$ $^mC_{ds}$ $T_{ds}$ $G_{ds}$ $^mC_{eo}$ $A_{eo}$ $T_{es}$ $T_{es}$ $^mC_e$ | 64407 | 64426 | 27.4 | 127 |
| 628849 | $A_{es}$ $^mC_{eo}$ $A_{eo}$ $G_{eo}$ $G_{eo}$ $T_{ds}$ $A_{ds}$ $A_{ds}$ $^mC_{ds}$ $^mC_{ds}$ $^mC_{ds}$ $^mC_{ds}$ $A_{ds}$ $T_{ds}$ $^mC_{ds}$ $T_{eo}$ $A_{eo}$ $G_{es}$ $G_{es}$ $^mC_e$ | 66432 | 66451 | 68.5 | 128 |
| 628569 | $G_{es}$ $G_{eo}$ $A_{eo}$ $G_{eo}$ $G_{eo}$ $T_{ds}$ $^mC_{ds}$ $^mC_{ds}$ $T_{ds}$ $G_{ds}$ $G_{ds}$ $T_{ds}$ $^mC_{ds}$ $T_{ds}$ $T_{ds}$ $^mC_{eo}$ $T_{eo}$ $T_{eo}$ $G_{es}$ $A_{es}$ $^mC_e$ | 67064 | 67083 | 41.4 | 129 |
| 628573 | $T_{es}$ $T_{eo}$ $A_{eo}$ $T_{eo}$ $^mC_{eo}$ $T_{ds}$ $T_{ds}$ $T_{ds}$ $^mC_{ds}$ $T_{ds}$ $T_{ds}$ $^mC_{ds}$ $A_{ds}$ $^mC_{ds}$ $^mC_{ds}$ $T_{eo}$ $T_{eo}$ $T_{es}$ $T_{es}$ $T_e$ | 67113 | 67132 | 27.1 | 130 |
| 628577 | $^mC_{es}$ $T_{eo}$ $^mC_{eo}$ $T_{eo}$ $T_{eo}$ $T_{ds}$ $^mC_{ds}$ $T_{ds}$ $T_{ds}$ $^mC_{ds}$ $T_{ds}$ $T_{ds}$ $T_{ds}$ $^mC_{eo}$ $T_{eo}$ $T_{es}$ $A_{es}$ $T_e$ | 67129 | 67148 | 43.9 | 131 |
| 628581 | $^mC_{es}$ $A_{eo}$ $^mC_{eo}$ $G_{eo}$ $G_{eo}$ $G_{ds}$ $^mC_{ds}$ $T_{ds}$ $^mC_{ds}$ $A_{ds}$ $T_{ds}$ $G_{ds}$ $^mC_{ds}$ $T_{ds}$ $T_{ds}$ $G_{eo}$ $^mC_{eo}$ $^mC_{es}$ $^mC_{es}$ $T_e$ | 67147 | 67166 | 15.0 | 132 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628585 | G$_{es}$ G$_{eo}$ $^m$C$_{eo}$ T$_{eo}$ G$_{eo}$ A$_{ds}$ T$_{ds}$ G$_{ds}$ G$_{ds}$ $^m$C$_{ds}$ T$_{ds}$ G$_{ds}$ $^m$C$_{ds}$ A$_{ds}$ $^m$C$_{ds}$ G$_{eo}$ G$_{eo}$ G$_{es}$ $^m$C$_{es}$ T$_e$ | 67159 | 67178 | 73.7 | 133 |
| 628589 | T$_{es}$ G$_{eo}$ $^m$C$_{eo}$ G$_{eo}$ G$_{eo}$ G$_{ds}$ $^m$C$_{ds}$ T$_{ds}$ $^m$C$_{ds}$ A$_{ds}$ G$_{ds}$ $^m$C$_{ds}$ A$_{ds}$ G$_{ds}$ A$_{ds}$ G$_{eo}$ T$_{eo}$ G$_{es}$ G$_{es}$ T$_e$ | 67180 | 67199 | 22.6 | 134 |
| 628593 | G$_{es}$ A$_{eo}$ $^m$C$_{eo}$ $^m$C$_{eo}$ $^m$C$_{eo}$ T$_{ds}$ T$_{ds}$ $^m$C$_{ds}$ T$_{ds}$ G$_{ds}$ A$_{ds}$ T$_{ds}$ G$_{ds}$ T$_{ds}$ $^m$C$_{ds}$ T$_{eo}$ $^m$C$_{eo}$ T$_{es}$ G$_{es}$ $^m$C$_e$ | 67212 | 67231 | 47.4 | 135 |
| 628597 | A$_{es}$ G$_{eo}$ G$_{eo}$ $^m$C$_{eo}$ A$_{eo}$ G$_{ds}$ A$_{ds}$ A$_{ds}$ G$_{ds}$ $^m$C$_{ds}$ T$_{ds}$ T$_{ds}$ $^m$C$_{ds}$ $^m$C$_{ds}$ G$_{ds}$ G$_{eo}$ $^m$C$_{eo}$ A$_{es}$ $^m$C$_{es}$ A$_e$ | 67247 | 67266 | 48.6 | 136 |
| 628601 | T$_{es}$ $^m$C$_{eo}$ A$_{eo}$ T$_{eo}$ A$_{eo}$ $^m$C$_{ds}$ A$_{ds}$ T$_{ds}$ G$_{ds}$ G$_{ds}$ G$_{ds}$ T$_{ds}$ $^m$C$_{ds}$ $^m$C$_{ds}$ $^m$C$_{ds}$ $^m$C$_{eo}$ G$_{eo}$ G$_{es}$ T$_{es}$ $^m$C$_e$ | 67296 | 67315 | 53.7 | 137 |
| 628605 | T$_{es}$ T$_{eo}$ T$_{eo}$ $^m$C$_{eo}$ $^m$C$_{eo}$ T$_{ds}$ T$_{ds}$ T$_{ds}$ G$_{ds}$ $^m$C$_{ds}$ T$_{ds}$ T$_{ds}$ A$_{ds}$ A$_{ds}$ G$_{ds}$ $^m$C$_{eo}$ T$_{eo}$ T$_{es}$ $^m$C$_{es}$ $^m$C$_e$ | 67345 | 67364 | 46.5 | 138 |
| 628609 | T$_{es}$ A$_{eo}$ $^m$C$_{eo}$ A$_{eo}$ $^m$C$_{eo}$ A$_{ds}$ T$_{ds}$ $^m$C$_{ds}$ A$_{ds}$ T$_{ds}$ A$_{ds}$ $^m$C$_{ds}$ T$_{ds}$ T$_{ds}$ $^m$C$_{ds}$ $^m$C$_{eo}$ $^m$C$_{eo}$ A$_{es}$ G$_{es}$ $^m$C$_e$ | 67377 | 67396 | 40.1 | 139 |
| 628613 | T$_{es}$ $^m$C$_{eo}$ A$_{eo}$ A$_{eo}$ $^m$C$_{eo}$ T$_{ds}$ $^m$C$_{ds}$ $^m$C$_{ds}$ A$_{ds}$ $^m$C$_{ds}$ T$_{ds}$ T$_{ds}$ T$_{ds}$ A$_{ds}$ G$_{ds}$ A$_{eo}$ G$_{eo}$ $^m$C$_{es}$ G$_{es}$ A$_e$ | 68180 | 68199 | 42.9 | 140 |
| 628617 | G$_{es}$ $^m$C$_{eo}$ $^m$C$_{eo}$ T$_{eo}$ A$_{eo}$ $^m$C$_{ds}$ $^m$C$_{ds}$ T$_{ds}$ T$_{ds}$ T$_{ds}$ T$_{ds}$ $^m$C$_{ds}$ G$_{ds}$ A$_{ds}$ A$_{ds}$ G$_{eo}$ T$_{eo}$ A$_{es}$ $^m$C$_{es}$ G$_e$ | 68203 | 68222 | 65.5 | 141 |
| 628621 | G$_{es}$ G$_{eo}$ T$_{eo}$ $^m$C$_{eo}$ $^m$C$_{eo}$ A$_{ds}$ G$_{ds}$ G$_{ds}$ G$_{ds}$ A$_{ds}$ T$_{ds}$ G$_{ds}$ T$_{ds}$ G$_{ds}$ T$_{ds}$ $^m$C$_{eo}$ G$_{eo}$ $^m$C$_{es}$ $^m$C$_{es}$ T$_e$ | 68219 | 68238 | 62.9 | 142 |
| 628625 | T$_{es}$ $^m$C$_{eo}$ $^m$C$_{eo}$ $^m$C$_{eo}$ T$_{eo}$ $^m$C$_{ds}$ T$_{ds}$ $^m$C$_{ds}$ $^m$C$_{ds}$ $^m$C$_{ds}$ A$_{ds}$ G$_{ds}$ T$_{ds}$ T$_{ds}$ A$_{ds}$ $^m$C$_{eo}$ $^m$C$_{eo}$ G$_{es}$ T$_{es}$ G$_e$ | 68255 | 68274 | 65.6 | 143 |
| 628629 | T$_{es}$ G$_{eo}$ G$_{eo}$ A$_{eo}$ G$_{eo}$ $^m$C$_{ds}$ T$_{ds}$ T$_{ds}$ T$_{ds}$ G$_{ds}$ G$_{ds}$ G$_{ds}$ A$_{ds}$ G$_{ds}$ A$_{ds}$ T$_{eo}$ T$_{eo}$ T$_{es}$ G$_{es}$ G$_e$ | 68311 | 68330 | 28.3 | 144 |
| 628633 | $^m$C$_{es}$ G$_{eo}$ T$_{eo}$ G$_{eo}$ G$_{eo}$ $^m$C$_{ds}$ $^m$C$_{ds}$ G$_{ds}$ $^m$C$_{ds}$ $^m$C$_{ds}$ T$_{ds}$ T$_{ds}$ G$_{ds}$ G$_{ds}$ G$_{ds}$ T$_{eo}$ $^m$C$_{eo}$ T$_{es}$ $^m$C$_{es}$ G$_e$ | 68374 | 68393 | 25.5 | 145 |
| 628637 | A$_{es}$ G$_{eo}$ G$_{eo}$ A$_{eo}$ $^m$C$_{eo}$ T$_{ds}$ T$_{ds}$ T$_{ds}$ T$_{ds}$ $^m$C$_{ds}$ T$_{ds}$ $^m$C$_{ds}$ $^m$C$_{ds}$ A$_{ds}$ G$_{ds}$ G$_{eo}$ A$_{eo}$ $^m$C$_{es}$ $^m$C$_{es}$ $^m$C$_e$ | 68416 | 68435 | 86.1 | 146 |
| 628641 | A$_{es}$ G$_{eo}$ G$_{eo}$ $^m$C$_{eo}$ A$_{eo}$ T$_{ds}$ $^m$C$_{ds}$ T$_{ds}$ T$_{ds}$ G$_{ds}$ A$_{ds}$ $^m$C$_{ds}$ A$_{ds}$ A$_{ds}$ G$_{ds}$ G$_{eo}$ A$_{eo}$ G$_{es}$ $^m$C$_{es}$ T$_e$ | 68440 | 68459 | 81.0 | 147 |
| 628645 | G$_{es}$ $^m$C$_{eo}$ $^m$C$_{eo}$ $^m$C$_{eo}$ $^m$C$_{eo}$ $^m$C$_{ds}$ T$_{ds}$ G$_{ds}$ G$_{ds}$ $^m$C$_{ds}$ G$_{ds}$ A$_{ds}$ A$_{ds}$ G$_{ds}$ T$_{ds}$ T$_{eo}$ T$_{eo}$ G$_{es}$ A$_{es}$ A$_e$ | 68461 | 68480 | 29.6 | 148 |
| 628649 | $^m$C$_{es}$ $^m$C$_{eo}$ $^m$C$_{eo}$ $^m$C$_{eo}$ A$_{eo}$ $^m$C$_{ds}$ $^m$C$_{ds}$ $^m$C$_{ds}$ $^m$C$_{ds}$ $^m$C$_{ds}$ T$_{ds}$ $^m$C$_{ds}$ A$_{ds}$ G$_{ds}$ $^m$C$_{eo}$ $^m$C$_{eo}$ T$_{es}$ T$_{es}$ G$_e$ | 68480 | 68499 | 39.9 | 149 |
| 628653 | $^m$C$_{es}$ $^m$C$_{eo}$ A$_{eo}$ T$_{eo}$ G$_{eo}$ A$_{ds}$ $^m$C$_{ds}$ $^m$C$_{ds}$ T$_{ds}$ G$_{ds}$ G$_{ds}$ G$_{ds}$ T$_{ds}$ G$_{ds}$ G$_{ds}$ A$_{eo}$ T$_{eo}$ G$_{es}$ T$_{es}$ G$_e$ | 68504 | 68523 | 39.7 | 150 |
| 628657 | $^m$C$_{es}$ T$_{eo}$ G$_{eo}$ A$_{eo}$ G$_{eo}$ G$_{ds}$ G$_{ds}$ T$_{ds}$ $^m$C$_{ds}$ G$_{ds}$ G$_{ds}$ $^m$C$_{ds}$ $^m$C$_{ds}$ T$_{ds}$ $^m$C$_{ds}$ A$_{eo}$ G$_{eo}$ $^m$C$_{es}$ T$_{es}$ T$_e$ | 68551 | 68570 | 28.6 | 151 |
| 628661 | $^m$C$_{es}$ $^m$C$_{eo}$ $^m$C$_{eo}$ G$_{eo}$ G$_{eo}$ $^m$C$_{ds}$ T$_{ds}$ T$_{ds}$ T$_{ds}$ $^m$C$_{ds}$ G$_{ds}$ G$_{ds}$ $^m$C$_{ds}$ $^m$C$_{ds}$ $^m$C$_{ds}$ $^m$C$_{eo}$ G$_{eo}$ T$_{es}$ T$_{es}$ T$_e$ | 68583 | 68602 | 37.3 | 152 |
| 628665 | T$_{es}$ G$_{eo}$ G$_{eo}$ $^m$C$_{eo}$ $^m$C$_{eo}$ T$_{ds}$ $^m$C$_{ds}$ G$_{ds}$ G$_{ds}$ $^m$C$_{ds}$ G$_{ds}$ G$_{ds}$ $^m$C$_{ds}$ A$_{ds}$ G$_{ds}$ $^m$C$_{eo}$ G$_{eo}$ G$_{es}$ $^m$C$_{es}$ T$_e$ | 68615 | 68634 | 38.2 | 153 |
| *628669 | T$_{es}$ $^m$C$_{eo}$ G$_{eo}$ G$_{eo}$ A$_{eo}$ T$_{ds}$ A$_{ds}$ G$_{ds}$ A$_{ds}$ A$_{ds}$ G$_{ds}$ A$_{ds}$ $^m$C$_{ds}$ T$_{ds}$ $^m$C$_{ds}$ $^m$C$_{eo}$ T$_{eo}$ T$_{es}$ $^m$C$_{es}$ A$_e$ | 68647 | 68666 | 66.3 | 154 |
| *628673 | T$_{es}$ A$_{eo}$ $^m$C$_{eo}$ G$_{eo}$ G$_{eo}$ T$_{ds}$ $^m$C$_{ds}$ T$_{ds}$ $^m$C$_{ds}$ $^m$C$_{ds}$ T$_{ds}$ G$_{ds}$ $^m$C$_{ds}$ A$_{ds}$ $^m$C$_{ds}$ A$_{eo}$ G$_{eo}$ A$_{es}$ T$_{es}$ $^m$C$_e$ | 68665 | 68684 | 83.3 | 155 |
| *628677 | A$_{es}$ $^m$C$_{eo}$ $^m$C$_{eo}$ T$_{eo}$ $^m$C$_{eo}$ G$_{ds}$ A$_{ds}$ T$_{ds}$ G$_{ds}$ $^m$C$_{ds}$ T$_{ds}$ G$_{ds}$ A$_{ds}$ $^m$C$_{ds}$ $^m$C$_{ds}$ G$_{eo}$ T$_{eo}$ $^m$C$_{es}$ T$_{es}$ $^m$C$_e$ | 68712 | 68731 | 70.8 | 156 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628681 | $^mC_{es}$ $T_{eo}$ $T_{eo}$ $^mC_{eo}$ $T_{eo}$ $^mC_{ds}$ $A_{ds}$ $^mC_{ds}$ $^mC_{ds}$ $G_{ds}$ $A_{ds}$ $G_{ds}$ $G_{ds}$ $G_{ds}$ $T_{ds}$ $G_{eo}$ $G_{eo}$ $A_{es}$ $^mC_{es}$ $A_e$ | 68758 | 68777 | 24.2 | 157 |
| 628685 | $G_{es}$ $G_{eo}$ $G_{eo}$ $^mC_{eo}$ $T_{eo}$ $^mC_{ds}$ $T_{ds}$ $T_{ds}$ $A_{ds}$ $^mC_{ds}$ $A_{ds}$ $G_{ds}$ $G_{ds}$ $T_{ds}$ $^mC_{ds}$ $T_{eo}$ $T_{eo}$ $^mC_{es}$ $A_{es}$ $G_e$ | 68790 | 68809 | 62.3 | 158 |
| 628689 | $^mC_{es}$ $T_{eo}$ $G_{eo}$ $^mC_{eo}$ $T_{eo}$ $G_{ds}$ $^mC_{ds}$ $T_{ds}$ $G_{ds}$ $^mC_{ds}$ $G_{ds}$ $^mC_{ds}$ $^mC_{ds}$ $^mC_{ds}$ $^mC_{ds}$ $T_{eo}$ $T_{eo}$ $G_{es}$ $G_{es}$ $G_e$ | 68835 | 68854 | 73.7 | 159 |
| 628693 | $T_{es}$ $^mC_{eo}$ $G_{eo}$ $G_{eo}$ $G_{eo}$ $^mC_{ds}$ $T_{ds}$ $^mC_{ds}$ $A_{ds}$ $G_{ds}$ $G_{ds}$ $T_{ds}$ $G_{ds}$ $G_{ds}$ $A_{ds}$ $G_{eo}$ $G_{eo}$ $T_{es}$ $G_{es}$ $G_e$ | 68946 | 68965 | 13.0 | 160 |
| 628697 | $^mC_{es}$ $T_{eo}$ $G_{eo}$ $G_{eo}$ $G_{eo}$ $^mC_{ds}$ $A_{ds}$ $T_{ds}$ $^mC_{ds}$ $T_{ds}$ $T_{ds}$ $^mC_{ds}$ $T_{ds}$ $^mC_{ds}$ $^mC_{ds}$ $T_{eo}$ $^mC_{eo}$ $T_{es}$ $T_{es}$ $T_e$ | 69024 | 69043 | 59.0 | 161 |
| 628701 | $G_{es}$ $T_{eo}$ $^mC_{eo}$ $T_{eo}$ $T_{eo}$ $A_{ds}$ $G_{ds}$ $^mC_{ds}$ $T_{ds}$ $G_{ds}$ $G_{ds}$ $^mC_{ds}$ $T_{ds}$ $^mC_{ds}$ $^mC_{ds}$ $T_{eo}$ $T_{eo}$ $G_{es}$ $G_{es}$ $G_e$ | 69072 | 69091 | 63.7 | 162 |
| 628705 | $G_{es}$ $G_{eo}$ $T_{eo}$ $G_{eo}$ $G_{eo}$ $^mC_{ds}$ $A_{ds}$ $A_{ds}$ $^mC_{ds}$ $^mC_{ds}$ $G_{ds}$ $^mC_{ds}$ $G_{ds}$ $G_{ds}$ $G_{ds}$ $^mC_{eo}$ $T_{eo}$ $G_{es}$ $A_{es}$ $G_e$ | 69091 | 69110 | 59.5 | 163 |
| 628709 | $^mC_{es}$ $G_{eo}$ $G_{eo}$ $^mC_{eo}$ $^mC_{eo}$ $G_{ds}$ $T_{ds}$ $G_{ds}$ $G_{ds}$ $^mC_{ds}$ $G_{ds}$ $G_{ds}$ $^mC_{ds}$ $G_{ds}$ $G_{ds}$ $T_{eo}$ $G_{eo}$ $G_{es}$ $^mC_{es}$ $L_e$ | 69104 | 69123 | 39.5 | 164 |
| 628713 | $T_{es}$ $G_{eo}$ $T_{eo}$ $T_{eo}$ $T_{eo}$ $G_{ds}$ $T_{ds}$ $A_{ds}$ $^mC_{ds}$ $T_{ds}$ $T_{ds}$ $T_{ds}$ $T_{ds}$ $^mC_{ds}$ $T_{ds}$ $G_{eo}$ $^mC_{eo}$ $G_{es}$ $G_{es}$ $^mC_e$ | 69120 | 69139 | 58.1 | 165 |
| 628717 | $A_{es}$ $A_{eo}$ $A_{eo}$ $^mC_{eo}$ $A_{eo}$ $A_{ds}$ $T_{ds}$ $G_{ds}$ $T_{ds}$ $^mC_{ds}$ $T_{ds}$ $T_{ds}$ $T_{ds}$ $G_{ds}$ $^mC_{ds}$ $G_{eo}$ $^mC_{eo}$ $T_{es}$ $^mC_{es}$ $T_e$ | 69152 | 69171 | 59.3 | 166 |
| 628721 | $^mC_{es}$ $T_{eo}$ $^mC_{eo}$ $^mC_{eo}$ $T_{eo}$ $^mC_{ds}$ $T_{ds}$ $^mC_{ds}$ $T_{ds}$ $^mC_{ds}$ $T_{ds}$ $^mC_{ds}$ $T_{ds}$ $T_{ds}$ $G_{ds}$ $G_{ds}$ $^mC_{eo}$ $^mC_{eo}$ $T_{es}$ $T_{es}$ $G_e$ | 69184 | 69203 | 61.6 | 167 |
| 628725 | $A_{es}$ $G_{eo}$ $T_{eo}$ $^mC_{eo}$ $A_{eo}$ $G_{ds}$ $^mC_{ds}$ $T_{ds}$ $A_{ds}$ $A_{ds}$ $^mC_{ds}$ $T_{ds}$ $^mC_{ds}$ $T_{ds}$ $^mC_{ds}$ $T_{eo}$ $^mC_{eo}$ $G_{es}$ $G_{es}$ $T_e$ | 69228 | 69247 | 66.3 | 168 |
| 628729 | $T_{es}$ $G_{eo}$ $T_{eo}$ $T_{eo}$ $G_{eo}$ $G_{ds}$ $T_{ds}$ $T_{ds}$ $T_{ds}$ $G_{ds}$ $^mC_{ds}$ $T_{ds}$ $T_{ds}$ $T_{ds}$ $G_{ds}$ $^mC_{eo}$ $A_{eo}$ $A_{es}$ $T_{es}$ $^mC_e$ | 69260 | 69279 | 79.7 | 169 |
| 628733 | $T_{es}$ $A_{eo}$ $A_{eo}$ $G_{eo}$ $G_{eo}$ $A_{ds}$ $G_{ds}$ $A_{ds}$ $A_{ds}$ $G_{ds}$ $A_{ds}$ $G_{ds}$ $A_{ds}$ $^mC_{ds}$ $A_{ds}$ $A_{eo}$ $^mC_{eo}$ $A_{es}$ $G_{es}$ $^mC_e$ | 69292 | 69311 | 35.1 | 170 |
| 628737 | $T_{es}$ $T_{eo}$ $A_{eo}$ $A_{eo}$ $T_{eo}$ $^mC_{ds}$ $G_{ds}$ $G_{ds}$ $G_{ds}$ $A_{ds}$ $A_{ds}$ $G_{ds}$ $^mC_{ds}$ $T_{ds}$ $T_{ds}$ $T_{eo}$ $G_{eo}$ $T_{es}$ $^mC_{es}$ $A_e$ | 69324 | 69343 | 78.1 | 171 |

Superscript "m" indicates 5-methylcytosine.
Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 3

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 18078 | $G_{es}$ $T_{es}$ $G_{es}$ $^mC_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ $^mC_e$ | n/a | n/a | 0.6 | 15 |
| 628542 | $G_{es}$ $A_{eo}$ $G_{eo}$ $G_{eo}$ $A_{eo}$ $G_{ds}$ $G_{ds}$ $G_{ds}$ $A_{ds}$ $G_{ds}$ $^mC_{ds}$ $G_{ds}$ $^mC_{ds}$ $G_{ds}$ $^mC_{ds}$ $G_{eo}$ $^mC_{eo}$ $G_{es}$ $^mC_{es}$ $^mC_e$ | 1886 | 1905 | 23.9 | 172 |
| 628546 | $^mC_{es}$ $^mC_{eo}$ $G_{eo}$ $G_{eo}$ $A_{eo}$ $^mC_{ds}$ $G_{ds}$ $G_{ds}$ $^mC_{ds}$ $T_{ds}$ $T_{ds}$ $T_{ds}$ $T_{ds}$ $A_{ds}$ $^mC_{ds}$ $^mC_{eo}$ $A_{eo}$ $^mC_{es}$ $A_{es}$ $G_e$ | 1918 | 1937 | 60.4 | 173 |
| 628550 | $^mC_{es}$ $T_{eo}$ $^mC_{eo}$ $^mC_{eo}$ $T_{eo}$ $^mC_{ds}$ $^mC_{ds}$ $T_{ds}$ $^mC_{ds}$ $^mC_{ds}$ $G_{ds}$ $^mC_{ds}$ $T_{ds}$ $^mC_{ds}$ $G_{ds}$ $G_{eo}$ $^mC_{eo}$ $G_{es}$ $^mC_{es}$ $G_e$ | 1961 | 1980 | 67.0 | 174 |
| 628742 | $A_{es}$ $T_{eo}$ $G_{eo}$ $^mC_{eo}$ $T_{eo}$ $T_{ds}$ $^mC_{ds}$ $A_{ds}$ $T_{ds}$ $T_{ds}$ $T_{ds}$ $T_{ds}$ $T_{ds}$ $A_{ds}$ $^mC_{ds}$ $A_{eo}$ $G_{eo}$ $T_{es}$ $A_{es}$ $T_e$ | 3547 | 3566 | 82.9 | 175 |

TABLE 3-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628746 | $G_{es}$ $A_{eo}$ $G_{eo}$ $^mC_{eo}$ $^mC_{eo}$ $A_{ds}$ $G_{ds}$ $A_{ds}$ $G_{ds}$ $G_{ds}$ $^mC_{ds}$ $T_{ds}$ $G_{ds}$ $G_{ds}$ $G_{ds}$ $T_{eo}$ $G_{eo}$ $^mC_{es}$ $G_{es}$ $G_e$ | 6078 | 6097 | 38.7 | 176 |
| 628554 | $T_{es}$ $G_{eo}$ $A_{eo}$ $G_{eo}$ $T_{eo}$ $^mC_{ds}$ $T_{ds}$ $G_{ds}$ $T_{ds}$ $A_{ds}$ $T_{ds}$ $T_{ds}$ $T_{ds}$ $T_{ds}$ $T_{ds}$ $A_{eo}$ $T_{eo}$ $G_{es}$ $G_{es}$ $A_e$ | 7300 | 7319 | 57.7 | 177 |
| 628558 | $G_{es}$ $G_{eo}$ $A_{eo}$ $G_{eo}$ $T_{eo}$ $^mC_{ds}$ $A_{ds}$ $^mC_{ds}$ $A_{ds}$ $T_{ds}$ $G_{ds}$ $T_{ds}$ $^mC_{ds}$ $A_{ds}$ $^mC_{ds}$ $A_{eo}$ $T_{eo}$ $^mC_{es}$ $A_{es}$ $A_e$ | 7332 | 7351 | 82.8 | 178 |
| 628562 | $G_{es}$ $A_{eo}$ $A_{eo}$ $T_{eo}$ $^mC_{eo}$ $^mC_{ds}$ $T_{ds}$ $G_{ds}$ $T_{ds}$ $T_{ds}$ $G_{ds}$ $G_{ds}$ $A_{ds}$ $G_{ds}$ $^mC_{ds}$ $T_{eo}$ $G_{eo}$ $G_{es}$ $T_{es}$ $^mC_e$ | 7375 | 7394 | 67.3 | 179 |
| 628566 | $^mC_{es}$ $T_{eo}$ $T_{eo}$ $^mC_{eo}$ $^mC_{eo}$ $^mC_{ds}$ $T_{ds}$ $G_{ds}$ $A_{ds}$ $G_{ds}$ $^mC_{ds}$ $^mC_{ds}$ $^mC_{ds}$ $T_{ds}$ $A_{ds}$ $A_{eo}$ $^mC_{eo}$ $A_{es}$ $T_{es}$ $^mC_e$ | 7407 | 7426 | 32.1 | 180 |
| 628750 | $^mC_{es}$ $^mC_{eo}$ $^mC_{eo}$ $A_{eo}$ $^mC_{eo}$ $A_{ds}$ $G_{ds}$ $^mC_{ds}$ $A_{ds}$ $G_{ds}$ $T_{ds}$ $A_{ds}$ $A_{ds}$ $A_{ds}$ $A_{ds}$ $G_{eo}$ $A_{eo}$ $G_{es}$ $A_{es}$ $A_e$ | 8615 | 8634 | 54.0 | 181 |
| 628754 | $A_{es}$ $^mC_{eo}$ $^mC_{eo}$ $^mC_{eo}$ $^mC_{eo}$ $A_{ds}$ $G_{ds}$ $T_{ds}$ $A_{ds}$ $G_{ds}$ $T_{ds}$ $T_{ds}$ $G_{ds}$ $A_{ds}$ $G_{ds}$ $A_{eo}$ $T_{eo}$ $T_{es}$ $A_{es}$ $^mC_e$ | 11009 | 11028 | 40.8 | 182 |
| 628758 | $A_{es}$ $T_{eo}$ $A_{eo}$ $G_{eo}$ $T_{eo}$ $A_{ds}$ $G_{ds}$ $T_{ds}$ $T_{ds}$ $G_{ds}$ $^mC_{ds}$ $^mC_{ds}$ $A_{ds}$ $G_{ds}$ $A_{ds}$ $G_{eo}$ $G_{eo}$ $G_{es}$ $T_{es}$ $G_e$ | 13862 | 13881 | 38.7 | 183 |
| 628762 | $G_{es}$ $G_{eo}$ $^mC_{eo}$ $T_{eo}$ $T_{eo}$ $^mC_{ds}$ $T_{ds}$ $A_{ds}$ $T_{ds}$ $T_{ds}$ $G_{ds}$ $T_{ds}$ $A_{ds}$ $A_{ds}$ $A_{ds}$ $A_{eo}$ $^mC_{eo}$ $T_{es}$ $A_{es}$ $T_e$ | 16687 | 16706 | 95.8 | 184 |
| 628766 | $A_{es}$ $^mC_{eo}$ $T_{eo}$ $G_{eo}$ $G_{eo}$ $T_{ds}$ $T_{ds}$ $T_{ds}$ $T_{ds}$ $T_{ds}$ $A_{ds}$ $A_{ds}$ $G_{ds}$ $A_{ds}$ $G_{ds}$ $A_{eo}$ $T_{eo}$ $G_{es}$ $G_{es}$ $G_e$ | 19134 | 19153 | 83.1 | 185 |
| 628770 | $T_{es}$ $A_{eo}$ $A_{eo}$ $A_{eo}$ $A_{eo}$ $T_{ds}$ $^mC_{ds}$ $T_{ds}$ $A_{ds}$ $T_{ds}$ $G_{ds}$ $G_{ds}$ $G_{ds}$ $A_{ds}$ $A_{ds}$ $T_{eo}$ $A_{eo}$ $A_{es}$ $A_{es}$ $A_e$ | 21818 | 21837 | -7.4 | 186 |
| 628774 | $G_{es}$ $A_{eo}$ $A_{eo}$ $A_{eo}$ $T_{eo}$ $G_{ds}$ $T_{ds}$ $G_{ds}$ $G_{ds}$ $G_{ds}$ $^mC_{ds}$ $T_{ds}$ $T_{ds}$ $G_{ds}$ $G_{ds}$ $^mC_{eo}$ $A_{eo}$ $T_{es}$ $G_{es}$ $G_e$ | 23936 | 23955 | 62.6 | 187 |
| 628778 | $A_{es}$ $A_{eo}$ $^mC_{eo}$ $A_{eo}$ $T_{eo}$ $G_{ds}$ $G_{ds}$ $T_{ds}$ $T_{ds}$ $T_{ds}$ $A_{ds}$ $G_{ds}$ $T_{ds}$ $A_{ds}$ $G_{ds}$ $A_{eo}$ $A_{eo}$ $A_{es}$ $^mC_{es}$ $^mC_e$ | 26672 | 26691 | 72.8 | 188 |
| 628782 | $G_{es}$ $G_{eo}$ $T_{eo}$ $A_{eo}$ $T_{eo}$ $T_{ds}$ $A_{ds}$ $T_{ds}$ $A_{ds}$ $A_{ds}$ $T_{ds}$ $T_{ds}$ $T_{ds}$ $T_{ds}$ $G_{ds}$ $T_{eo}$ $A_{eo}$ $A_{es}$ $T_{es}$ $T_e$ | 28682 | 28701 | 49.9 | 189 |
| 628786 | $^mC_{es}$ $A_{eo}$ $A_{eo}$ $^mC_{eo}$ $A_{eo}$ $T_{ds}$ $T_{ds}$ $^mC_{ds}$ $^mC_{ds}$ $A_{ds}$ $T_{ds}$ $T_{ds}$ $T_{ds}$ $A_{ds}$ $T_{ds}$ $T_{eo}$ $T_{eo}$ $A_{es}$ $G_{es}$ $G_e$ | 31258 | 31277 | 90.5 | 190 |
| 628790 | $A_{es}$ $T_{eo}$ $T_{eo}$ $T_{eo}$ $T_{eo}$ $^mC_{ds}$ $A_{ds}$ $^mC_{ds}$ $^mC_{ds}$ $^mC_{ds}$ $T_{ds}$ $T_{ds}$ $T_{ds}$ $A_{ds}$ $A_{ds}$ $A_{eo}$ $A_{eo}$ $A_{es}$ $T_{es}$ $^mC_e$ | 33773 | 33792 | 63.0 | 191 |
| 628794 | $T_{es}$ $A_{eo}$ $A_{eo}$ $T_{eo}$ $A_{eo}$ $^mC_{ds}$ $A_{ds}$ $G_{ds}$ $T_{ds}$ $G_{ds}$ $A_{ds}$ $^mC_{ds}$ $A_{ds}$ $A_{ds}$ $G_{ds}$ $^mC_{eo}$ $A_{eo}$ $T_{es}$ $^mC_{es}$ $^mC_e$ | 35787 | 35806 | 68.0 | 192 |
| 628798 | $T_{es}$ $^mC_{eo}$ $^mC_{eo}$ $A_{eo}$ $T_{eo}$ $^mC_{ds}$ $T_{ds}$ $T_{ds}$ $G_{ds}$ $^mC_{ds}$ $A_{ds}$ $G_{ds}$ $G_{ds}$ $T_{ds}$ $G_{ds}$ $G_{eo}$ $A_{eo}$ $G_{es}$ $T_{es}$ $A_e$ | 38549 | 38568 | 77.6 | 193 |
| 628802 | $G_{es}$ $A_{eo}$ $A_{eo}$ $G_{eo}$ $^mC_{eo}$ $^mC_{ds}$ $A_{ds}$ $A_{ds}$ $A_{ds}$ $A_{ds}$ $A_{ds}$ $A_{ds}$ $G_{ds}$ $^mC_{ds}$ $A_{ds}$ $A_{eo}$ $^mC_{eo}$ $A_{es}$ $A_{es}$ $A_e$ | 40573 | 40592 | 60.5 | 194 |
| 628806 | $^mC_{es}$ $^mC_{eo}$ $A_{eo}$ $A_{eo}$ $G_{eo}$ $A_{ds}$ $^mC_{ds}$ $A_{ds}$ $A_{ds}$ $G_{ds}$ $G_{ds}$ $A_{ds}$ $A_{ds}$ $A_{ds}$ $A_{ds}$ $A_{eo}$ $^mC_{eo}$ $G_{es}$ $G_{es}$ $G_e$ | 43080 | 43099 | 57.5 | 195 |
| 628810 | $^mC_{es}$ $T_{eo}$ $A_{eo}$ $G_{eo}$ $^mC_{eo}$ $T_{ds}$ $A_{ds}$ $T_{ds}$ $^mC_{ds}$ $A_{ds}$ $G_{ds}$ $^mC_{ds}$ $T_{ds}$ $G_{ds}$ $G_{ds}$ $G_{eo}$ $^mC_{eo}$ $A_{es}$ $T_{es}$ $G_e$ | 45258 | 45277 | 66.7 | 196 |
| 628814 | $T_{es}$ $G_{eo}$ $^mC_{eo}$ $^mC_{eo}$ $T_{eo}$ $T_{ds}$ $G_{ds}$ $T_{ds}$ $T_{ds}$ $T_{ds}$ $G_{ds}$ $G_{ds}$ $G_{ds}$ $T_{ds}$ $A_{ds}$ $T_{eo}$ $A_{eo}$ $^mC_{es}$ $A_{es}$ $G_e$ | 47334 | 47353 | 72.0 | 197 |
| 628818 | $G_{es}$ $^mC_{eo}$ $T_{eo}$ $A_{eo}$ $A_{eo}$ $G_{ds}$ $T_{ds}$ $T_{ds}$ $A_{ds}$ $G_{ds}$ $A_{ds}$ $A_{ds}$ $^mC_{ds}$ $T_{ds}$ $^mC_{ds}$ $^mC_{eo}$ $G_{eo}$ $T_{es}$ $G_{es}$ $G_e$ | 49363 | 49382 | 49.4 | 198 |
| 628822 | $A_{es}$ $^mC_{eo}$ $A_{eo}$ $^mC_{eo}$ $G_{eo}$ $^mC_{ds}$ $^mC_{ds}$ $T_{ds}$ $G_{ds}$ $T_{ds}$ $G_{ds}$ $A_{ds}$ $A_{ds}$ $T_{ds}$ $^mC_{ds}$ $^mC_{ds}$ $T_{eo}$ $G_{eo}$ $^mC_{es}$ $A_{es}$ $T_e$ | 51552 | 51571 | 81.5 | 199 |
| 628826 | $^mC_{es}$ $A_{eo}$ $A_{eo}$ $^mC_{eo}$ $T_{eo}$ $G_{ds}$ $G_{ds}$ $A_{ds}$ $G_{ds}$ $G_{ds}$ $^mC_{ds}$ $^mC_{ds}$ $G_{ds}$ $G_{ds}$ $G_{ds}$ $^mC_{eo}$ $G_{eo}$ $^mC_{es}$ $G_{es}$ $A_e$ | 54069 | 54088 | 9.7 | 200 |

TABLE 3-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628830 | $A_{es}$ $G_{eo}$ $^mC_{eo}$ $^mC_{eo}$ $^mC_{eo}$ $A_{ds}$ $^mC_{ds}$ $A_{ds}$ $^mC_{ds}$ $A_{ds}$ $G_{ds}$ $^mC_{ds}$ $T_{ds}$ $G_{ds}$ $T_{ds}$ $^mC_{eo}$ $T_{eo}$ $^mC_{es}$ $A_{es}$ $G_e$ | 56096 | 56115 | 41.4 | 201 |
| 628834 | $T_{es}$ $T_{eo}$ $^mC_{eo}$ $^mC_{eo}$ $T_{eo}$ $^mC_{ds}$ $A_{ds}$ $T_{ds}$ $G_{ds}$ $A_{ds}$ $A_{ds}$ $T_{ds}$ $G_{ds}$ $T_{ds}$ $G_{ds}$ $A_{eo}$ $^mC_{eo}$ $^mC_{es}$ $T_{es}$ $G_e$ | 58122 | 58141 | 47.6 | 202 |
| 628838 | $G_{es}$ $A_{eo}$ $G_{eo}$ $G_{eo}$ $A_{eo}$ $A_{ds}$ $^mC_{ds}$ $T_{ds}$ $T_{ds}$ $G_{ds}$ $T_{ds}$ $^mC_{ds}$ $T_{ds}$ $G_{ds}$ $A_{ds}$ $G_{eo}$ $A_{eo}$ $T_{es}$ $^mC_{es}$ $A_e$ | 60766 | 60785 | 68.3 | 203 |
| 628842 | $^mC_{es}$ $A_{eo}$ $G_{eo}$ $^mC_{eo}$ $T_{eo}$ $A_{ds}$ $^mC_{ds}$ $T_{ds}$ $^mC_{ds}$ $G_{ds}$ $^mC_{ds}$ $T_{ds}$ $A_{ds}$ $G_{ds}$ $A_{ds}$ $A_{eo}$ $A_{eo}$ $G_{es}$ $G_{es}$ $G_e$ | 62880 | 62899 | 70.8 | 204 |
| 628846 | $^mC_{es}$ $T_{eo}$ $^mC_{eo}$ $^mC_{eo}$ $^mC_{eo}$ $^mC_{ds}$ $A_{ds}$ $T_{ds}$ $A_{ds}$ $A_{ds}$ $A_{ds}$ $G_{ds}$ $G_{ds}$ $A_{ds}$ $G_{ds}$ $G_{eo}$ $G_{eo}$ $A_{es}$ $G_{es}$ $G_e$ | 64930 | 64949 | 1.6 | 205 |
| 628850 | $^mC_{es}$ $^mC_{eo}$ $A_{eo}$ $T_{eo}$ $^mC_{eo}$ $A_{ds}$ $T_{ds}$ $A_{ds}$ $^mC_{ds}$ $A_{ds}$ $^mC_{ds}$ $T_{ds}$ $^mC_{ds}$ $A_{ds}$ $G_{ds}$ $A_{eo}$ $T_{eo}$ $^mC_{es}$ $T_{es}$ $T_e$ | 66932 | 66951 | 62.6 | 206 |
| 628570 | $T_{es}$ $T_{eo}$ $G_{eo}$ $A_{eo}$ $G_{eo}$ $G_{ds}$ $^mC_{ds}$ $^mC_{ds}$ $^mC_{ds}$ $T_{ds}$ $G_{ds}$ $G_{ds}$ $A_{ds}$ $G_{ds}$ $G_{ds}$ $T_{eo}$ $^mC_{eo}$ $^mC_{es}$ $T_{es}$ $G_e$ | 67074 | 67093 | 31.1 | 207 |
| 628574 | $T_{es}$ $T_{eo}$ $^mC_{eo}$ $T_{eo}$ $T_{eo}$ $T_{ds}$ $^mC_{ds}$ $T_{ds}$ $T_{ds}$ $A_{ds}$ $T_{ds}$ $^mC_{ds}$ $T_{ds}$ $T_{ds}$ $T_{ds}$ $^mC_{eo}$ $T_{eo}$ $T_{es}$ $^mC_{es}$ $A_e$ | 67120 | 67139 | 39.8 | 208 |
| 628578 | $G_{es}$ $^mC_{eo}$ $^mC_{eo}$ $^mC_{eo}$ $T_{eo}$ $^mC_{ds}$ $T_{ds}$ $T_{ds}$ $T_{ds}$ $^mC_{ds}$ $T_{ds}$ $^mC_{ds}$ $T_{ds}$ $T_{ds}$ $^mC_{ds}$ $T_{eo}$ $T_{eo}$ $T_{es}$ $^mC_{es}$ $T_e$ | 67132 | 67151 | 46.7 | 209 |
| 628582 | $^mC_{es}$ $T_{eo}$ $G_{eo}$ $^mC_{eo}$ $A_{eo}$ $^mC_{ds}$ $G_{ds}$ $G_{ds}$ $G_{ds}$ $^mC_{ds}$ $T_{ds}$ $^mC_{ds}$ $A_{ds}$ $T_{ds}$ $G_{ds}$ $^mC_{eo}$ $T_{eo}$ $T_{es}$ $G_{es}$ $^mC_e$ | 67150 | 67169 | 69.0 | 210 |
| 628586 | $G_{es}$ $T_{eo}$ $G_{eo}$ $G_{eo}$ $G_{eo}$ $^mC_{ds}$ $T_{ds}$ $G_{ds}$ $A_{ds}$ $G_{ds}$ $G_{ds}$ $G_{ds}$ $^mC_{ds}$ $T_{ds}$ $G_{ds}$ $^mC_{eo}$ $A_{eo}$ $^mC_{es}$ $G_{es}$ $G_e$ | 67162 | 67181 | 31.7 | 211 |
| 628590 | $^mC_{es}$ $^mC_{eo}$ $T_{eo}$ $G_{eo}$ $^mC_{eo}$ $^mC_{ds}$ $T_{ds}$ $^mC_{ds}$ $T_{ds}$ $G_{ds}$ $^mC_{ds}$ $G_{ds}$ $G_{ds}$ $G_{ds}$ $^mC_{ds}$ $T_{eo}$ $^mC_{eo}$ $A_{es}$ $G_{es}$ $^mC_e$ | 67188 | 67207 | 39.4 | 212 |
| 628594 | $^mC_{es}$ $G_{eo}$ $G_{eo}$ $A_{eo}$ $G_{eo}$ $^mC_{ds}$ $^mC_{ds}$ $T_{ds}$ $G_{ds}$ $A_{ds}$ $^mC_{ds}$ $^mC_{ds}$ $^mC_{ds}$ $T_{ds}$ $T_{ds}$ $^mC_{eo}$ $T_{eo}$ $G_{eo}$ $A_{es}$ $T_e$ | 67220 | 67239 | 50.9 | 213 |
| 628598 | $G_{es}$ $G_{eo}$ $G_{eo}$ $A_{eo}$ $G_{eo}$ $G_{ds}$ $^mC_{ds}$ $A_{ds}$ $G_{ds}$ $A_{ds}$ $A_{ds}$ $G_{ds}$ $^mC_{ds}$ $T_{ds}$ $T_{ds}$ $^mC_{eo}$ $^mC_{eo}$ $G_{es}$ $G_{es}$ $^mC_e$ | 67250 | 67269 | 15.8 | 214 |
| 628602 | $^mC_{es}$ $^mC_{eo}$ $A_{eo}$ $G_{eo}$ $^mC_{eo}$ $^mC_{ds}$ $T_{ds}$ $T_{ds}$ $^mC_{ds}$ $A_{ds}$ $G_{ds}$ $G_{ds}$ $^mC_{ds}$ $A_{ds}$ $G_{ds}$ $G_{eo}$ $G_{eo}$ $T_{es}$ $G_{es}$ $G_e$ | 67321 | 67340 | 37.1 | 215 |
| 628606 | $^mC_{es}$ $G_{eo}$ $G_{eo}$ $^mC_{eo}$ $^mC_{eo}$ $A_{ds}$ $G_{ds}$ $A_{ds}$ $T_{ds}$ $T_{ds}$ $T_{ds}$ $^mC_{ds}$ $^mC_{ds}$ $T_{ds}$ $T_{ds}$ $T_{eo}$ $G_{eo}$ $^mC_{es}$ $T_{es}$ $T_e$ | 67353 | 67372 | 55.6 | 216 |
| 628610 | $T_{es}$ $G_{eo}$ $A_{eo}$ $T_{eo}$ $^mC_{eo}$ $A_{ds}$ $A_{ds}$ $A_{ds}$ $T_{ds}$ $A_{ds}$ $^mC_{ds}$ $A_{ds}$ $^mC_{ds}$ $A_{ds}$ $T_{ds}$ $^mC_{eo}$ $A_{eo}$ $T_{es}$ $A_{es}$ $^mC_e$ | 67385 | 67404 | 53.0 | 217 |
| 628614 | $G_{es}$ $T_{eo}$ $A_{eo}$ $^mC_{eo}$ $G_{eo}$ $^mC_{ds}$ $A_{ds}$ $A_{ds}$ $T_{ds}$ $^mC_{ds}$ $A_{ds}$ $A_{ds}$ $^mC_{ds}$ $T_{ds}$ $^mC_{ds}$ $^mC_{eo}$ $A_{eo}$ $^mC_{es}$ $T_{es}$ $T_e$ | 68188 | 68207 | 83.9 | 218 |
| 628618 | $T_{es}$ $G_{eo}$ $T_{eo}$ $G_{eo}$ $T_{eo}$ $^mC_{ds}$ $G_{ds}$ $^mC_{ds}$ $^mC_{ds}$ $T_{ds}$ $A_{ds}$ $^mC_{ds}$ $^mC_{ds}$ $T_{ds}$ $T_{ds}$ $T_{eo}$ $T_{eo}$ $^mC_{es}$ $G_{es}$ $A_e$ | 68209 | 68228 | 50.1 | 219 |
| 628622 | $^mC_{es}$ $A_{eo}$ $A_{eo}$ $A_{eo}$ $A_{eo}$ $T_{ds}$ $^mC_{ds}$ $A_{ds}$ $T_{ds}$ $T_{ds}$ $A_{ds}$ $G_{ds}$ $G_{ds}$ $G_{ds}$ $T_{ds}$ $^mC_{eo}$ $^mC_{eo}$ $A_{es}$ $G_{es}$ $G_e$ | 68231 | 68250 | 58.6 | 220 |
| 628626 | $T_{es}$ $T_{eo}$ $T_{eo}$ $^mC_{eo}$ $T_{eo}$ $G_{ds}$ $^mC_{ds}$ $T_{ds}$ $^mC_{ds}$ $T_{ds}$ $^mC_{ds}$ $G_{ds}$ $^mC_{ds}$ $^mC_{ds}$ $G_{ds}$ $G_{eo}$ $G_{eo}$ $A_{es}$ $G_{es}$ $G_e$ | 68278 | 68297 | 35.9 | 221 |
| 628630 | $^mC_{es}$ $^mC_{eo}$ $A_{eo}$ $G_{eo}$ $T_{eo}$ $T_{ds}$ $^mC_{ds}$ $^mC_{ds}$ $T_{ds}$ $G_{ds}$ $G_{ds}$ $A_{ds}$ $G_{ds}$ $^mC_{ds}$ $T_{ds}$ $T_{eo}$ $T_{eo}$ $G_{es}$ $G_{es}$ $G_e$ | 68319 | 68338 | 51.3 | 222 |
| 628634 | $^mC_{es}$ $A_{eo}$ $^mC_{eo}$ $^mC_{eo}$ $T_{eo}$ $G_{ds}$ $^mC_{ds}$ $A_{ds}$ $^mC_{ds}$ $A_{ds}$ $^mC_{ds}$ $^mC_{ds}$ $^mC_{ds}$ $T_{ds}$ $^mC_{ds}$ $T_{eo}$ $G_{eo}$ $A_{es}$ $^mC_{es}$ $G_e$ | 68392 | 68411 | 53.6 | 223 |
| 628638 | $G_{es}$ $A_{eo}$ $G_{eo}$ $^mC_{eo}$ $T_{eo}$ $T_{ds}$ $^mC_{ds}$ $^mC_{ds}$ $A_{ds}$ $G_{ds}$ $G_{ds}$ $A_{ds}$ $^mC_{ds}$ $T_{ds}$ $T_{eo}$ $T_{eo}$ $T_{es}$ $^mC_{es}$ $T_e$ | 68425 | 68444 | 57.1 | 224 |
| 628642 | $G_{es}$ $T_{eo}$ $T_{eo}$ $T_{eo}$ $G_{eo}$ $A_{ds}$ $A_{ds}$ $A_{ds}$ $A_{ds}$ $G_{ds}$ $G_{ds}$ $^mC_{ds}$ $A_{ds}$ $T_{ds}$ $^mC_{ds}$ $T_{eo}$ $T_{eo}$ $G_{es}$ $A_{es}$ $^mC_e$ | 68448 | 68467 | 40.8 | 225 |

TABLE 3-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628646 | $^mC_{es}$ $T_{eo}$ $T_{eo}$ $G_{eo}$ $^mC_{eo}$ $^mC_{ds}$ $^mC_{ds}$ $^mC_{ds}$ $^mC_{ds}$ $T_{ds}$ $G_{ds}$ $G_{ds}$ $^mC_{ds}$ $G_{ds}$ $A_{ds}$ $A_{eo}$ $G_{eo}$ $T_{es}$ $T_{es}$ $T_e$ | 68464 | 68483 | 58.5 | 226 |
| 628650 | $T_{es}$ $G_{eo}$ $T_{eo}$ $G_{eo}$ $G_{eo}$ $T_{ds}$ $G_{ds}$ $G_{ds}$ $^mC_{ds}$ $^mC_{ds}$ $^mC_{ds}$ $^mC_{ds}$ $A_{ds}$ $^mC_{ds}$ $^mC_{ds}$ $^mC_{eo}$ $^mC_{eo}$ $^mC_{es}$ $^mC_{es}$ $T_e$ | 68488 | 68507 | 57.7 | 227 |
| 628654 | $T_{es}$ $T_{eo}$ $T_{eo}$ $G_{eo}$ $A_{eo}$ $T_{ds}$ $^mC_{ds}$ $A_{ds}$ $^mC_{ds}$ $^mC_{ds}$ $A_{ds}$ $T_{ds}$ $G_{ds}$ $A_{ds}$ $^mC_{ds}$ $^mC_{eo}$ $T_{eo}$ $G_{es}$ $G_{es}$ $G_e$ | 68512 | 68531 | 69.1 | 228 |
| 628658 | $G_{es}$ $G_{eo}$ $A_{eo}$ $A_{eo}$ $T_{eo}$ $G_{ds}$ $G_{ds}$ $^mC_{ds}$ $^mC_{ds}$ $T_{ds}$ $G_{ds}$ $A_{ds}$ $G_{ds}$ $G_{ds}$ $G_{ds}$ $T_{eo}$ $^mC_{eo}$ $G_{es}$ $G_{es}$ $^mC_e$ | 68559 | 68578 | 35.4 | 229 |
| 628662 | $^mC_{es}$ $^mC_{eo}$ $A_{eo}$ $^mC_{eo}$ $A_{eo}$ $^mC_{ds}$ $T_{ds}$ $^mC_{ds}$ $^mC_{ds}$ $^mC_{ds}$ $^mC_{ds}$ $G_{ds}$ $G_{ds}$ $^mC_{ds}$ $T_{ds}$ $T_{eo}$ $T_{eo}$ $^mC_{es}$ $G_{es}$ $G_e$ | 68591 | 68610 | 58.1 | 230 |
| 628666 | $T_{es}$ $T_{eo}$ $T_{eo}$ $^mC_{eo}$ $T_{eo}$ $T_{ds}$ $T_{ds}$ $T_{ds}$ $T_{ds}$ $G_{ds}$ $G_{ds}$ $^mC_{ds}$ $^mC_{ds}$ $T_{ds}$ $^mC_{ds}$ $G_{eo}$ $G_{eo}$ $^mC_{es}$ $G_{es}$ $G_e$ | 68623 | 68642 | 47.3 | 231 |
| 628670 | $^mC_{es}$ $T_{eo}$ $G_{eo}$ $^mC_{eo}$ $A_{eo}$ $^mC_{ds}$ $A_{ds}$ $G_{ds}$ $A_{ds}$ $T_{ds}$ $^mC_{ds}$ $G_{ds}$ $G_{ds}$ $A_{ds}$ $T_{ds}$ $A_{eo}$ $G_{eo}$ $A_{es}$ $A_{es}$ $G_e$ | 68656 | 68675 | 81.0 | 232 |
| *628674 | $G_{es}$ $T_{eo}$ $^mC_{eo}$ $T_{eo}$ $T_{eo}$ $G_{ds}$ $^mC_{ds}$ $G_{ds}$ $^mC_{ds}$ $T_{ds}$ $^mC_{ds}$ $T_{ds}$ $T_{ds}$ $G_{ds}$ $A_{eo}$ $T_{eo}$ $G_{es}$ $G_{es}$ $G_e$ | 68688 | 68707 | 69.4 | 233 |
| *628678 | $^mC_{es}$ $T_{eo}$ $T_{eo}$ $^mC_{eo}$ $^mC_{eo}$ $T_{ds}$ $T_{ds}$ $G_{ds}$ $A_{ds}$ $^mC_{ds}$ $^mC_{ds}$ $T_{ds}$ $^mC_{ds}$ $G_{ds}$ $A_{ds}$ $T_{eo}$ $G_{eo}$ $^mC_{es}$ $T_{es}$ $G_e$ | 68720 | 68739 | 95.8 | 234 |
| 628682 | $T_{es}$ $T_{eo}$ $^mC_{eo}$ $^mC_{eo}$ $^mC_{eo}$ $G_{ds}$ $^mC_{ds}$ $T_{ds}$ $^mC_{ds}$ $T_{ds}$ $T_{ds}$ $^mC_{ds}$ $T_{ds}$ $^mC_{ds}$ $A_{ds}$ $^mC_{eo}$ $^mC_{eo}$ $G_{es}$ $A_{es}$ $G_e$ | 68766 | 68785 | 45.1 | 235 |
| 628686 | $T_{es}$ $^mC_{eo}$ $^mC_{eo}$ $G_{eo}$ $^mC_{eo}$ $^mC_{ds}$ $^mC_{ds}$ $A_{ds}$ $G_{ds}$ $G_{ds}$ $G_{ds}$ $^mC_{ds}$ $T_{ds}$ $^mC_{ds}$ $T_{ds}$ $T_{eo}$ $A_{eo}$ $^mC_{es}$ $A_{es}$ $G_e$ | 68798 | 68817 | 53.0 | 236 |
| 628690 | $T_{es}$ $G_{eo}$ $G_{eo}$ $T_{eo}$ $G_{eo}$ $G_{ds}$ $T_{ds}$ $G_{ds}$ $^mC_{ds}$ $T_{ds}$ $^mC_{ds}$ $^mC_{ds}$ $T_{ds}$ $T_{ds}$ $^mC_{ds}$ $T_{eo}$ $T_{eo}$ $G_{es}$ $G_{es}$ $G_e$ | 68868 | 68887 | 87.2 | 237 |
| 628694 | $^mC_{es}$ $G_{eo}$ $G_{eo}$ $A_{eo}$ $G_{eo}$ $^mC_{ds}$ $T_{ds}$ $^mC_{ds}$ $T_{ds}$ $^mC_{ds}$ $G_{ds}$ $G_{ds}$ $G_{ds}$ $^mC_{ds}$ $T_{ds}$ $^mC_{eo}$ $A_{eo}$ $G_{es}$ $G_{es}$ $T_e$ | 68954 | 68973 | 79.7 | 238 |
| 628698 | $A_{es}$ $G_{eo}$ $^mC_{eo}$ $^mC_{eo}$ $T_{eo}$ $^mC_{ds}$ $^mC_{ds}$ $T_{ds}$ $^mC_{ds}$ $T_{ds}$ $G_{ds}$ $G_{ds}$ $G_{ds}$ $^mC_{ds}$ $A_{ds}$ $T_{eo}$ $^mC_{eo}$ $T_{es}$ $T_{es}$ $^mC_e$ | 69032 | 69051 | 51.1 | 239 |
| 628702 | $^mC_{es}$ $G_{eo}$ $G_{eo}$ $G_{eo}$ $^mC_{eo}$ $T_{ds}$ $G_{ds}$ $A_{ds}$ $G_{ds}$ $^mC_{ds}$ $T_{ds}$ $T_{ds}$ $A_{ds}$ $G_{ds}$ $^mC_{ds}$ $T_{eo}$ $G_{es}$ $G_{es}$ $^mC_e$ | 69080 | 69099 | 69.6 | 240 |
| 628706 | $G_{es}$ $G_{eo}$ $^mC_{eo}$ $G_{eo}$ $G_{eo}$ $T_{ds}$ $G_{ds}$ $G_{ds}$ $^mC_{ds}$ $A_{ds}$ $A_{ds}$ $^mC_{ds}$ $^mC_{ds}$ $G_{ds}$ $^mC_{ds}$ $G_{eo}$ $G_{eo}$ $G_{es}$ $^mC_{es}$ $T_e$ | 69094 | 69113 | 62.7 | 241 |
| 628710 | $T_{es}$ $^mC_{eo}$ $T_{eo}$ $G_{eo}$ $^mC_{eo}$ $G_{ds}$ $G_{ds}$ $^mC_{ds}$ $^mC_{ds}$ $G_{ds}$ $T_{ds}$ $G_{ds}$ $G_{ds}$ $^mC_{ds}$ $G_{ds}$ $G_{eo}$ $^mC_{eo}$ $G_{ds}$ $G_{ds}$ $T_e$ | 69108 | 69127 | 54.2 | 242 |
| 628714 | $^mC_{es}$ $^mC_{eo}$ $^mC_{eo}$ $^mC_{eo}$ $T_{eo}$ $^mC_{ds}$ $G_{ds}$ $G_{ds}$ $T_{ds}$ $G_{ds}$ $T_{ds}$ $T_{ds}$ $T_{ds}$ $G_{ds}$ $T_{ds}$ $A_{eo}$ $^mC_{eo}$ $T_{es}$ $T_{es}$ $T_e$ | 69128 | 69147 | 47.5 | 243 |
| 628718 | $G_{es}$ $G_{eo}$ $A_{eo}$ $G_{eo}$ $G_{eo}$ $A_{ds}$ $T_{ds}$ $G_{ds}$ $A_{ds}$ $A_{ds}$ $A_{ds}$ $^mC_{ds}$ $A_{ds}$ $A_{ds}$ $T_{ds}$ $G_{eo}$ $T_{eo}$ $^mC_{es}$ $T_{es}$ $T_e$ | 69160 | 69179 | 53.6 | 244 |
| 628722 | $T_{es}$ $^mC_{eo}$ $^mC_{eo}$ $A_{eo}$ $^mC_{eo}$ $A_{ds}$ $G_{ds}$ $G_{ds}$ $^mC_{ds}$ $T_{ds}$ $^mC_{ds}$ $^mC_{ds}$ $T_{ds}$ $^mC_{ds}$ $T_{ds}$ $^mC_{eo}$ $T_{eo}$ $G_{es}$ $T_{es}$ $T_e$ | 69192 | 69211 | 24.4 | 245 |
| 628726 | $^mC_{es}$ $^mC_{eo}$ $G_{eo}$ $T_{eo}$ $G_{eo}$ $T_{ds}$ $A_{ds}$ $A_{ds}$ $A_{ds}$ $G_{ds}$ $T_{ds}$ $^mC_{ds}$ $A_{ds}$ $G_{ds}$ $^mC_{ds}$ $T_{eo}$ $A_{eo}$ $A_e$ $^mC_{es}$ $T_e$ | 69236 | 69255 | 65.9 | 246 |
| 628730 | $T_{es}$ $T_{eo}$ $T_{eo}$ $A_{eo}$ $T_{eo}$ $T_{ds}$ $^mC_{ds}$ $T_{ds}$ $T_{ds}$ $T_{ds}$ $T_{ds}$ $G_{ds}$ $G_{ds}$ $T_{ds}$ $T_{eo}$ $T_{eo}$ $G_{es}$ $^mC_{es}$ $T_e$ | 69268 | 69287 | 65.8 | 247 |

TABLE 3-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628734 | $^mC_{es}$ $^mC_{eo}$ $T_{eo}$ $A_{eo}$ $^mC_{eo}$ $^mC_{ds}$ $^mC_{ds}$ $A_{ds}$ $T_{ds}$ $A_{ds}$ $A_{ds}$ $G_{ds}$ $G_{ds}$ $A_{ds}$ $G_{ds}$ $A_{eo}$ $A_{eo}$ $G_{es}$ $A_{es}$ $G_e$ | 69300 | 69319 | 48.9 | 248 |
| 628738 | $T_{es}$ $A_{eo}$ $T_{eo}$ $T_{eo}$ $T_{eo}$ $^mC_{ds}$ $A_{ds}$ $G_{ds}$ $T_{ds}$ $T_{ds}$ $A_{ds}$ $A_{ds}$ $T_{ds}$ $^mC_{ds}$ $G_{ds}$ $G_{eo}$ $G_{eo}$ $A_{es}$ $A_{es}$ $G_e$ | 69332 | 69351 | 47.8 | 249 |

Superscript "m" indicates 5-methylcytosine.
Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 4

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 18078 | $G_{es}$ $T_{es}$ $G_{es}$ $^mC_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $T_{es}$ $^mC_e$ | n/a | n/a | -9.9 | 15 |
| 628544 | $A_{es}$ $^mC_{eo}$ $A_{eo}$ $G_{eo}$ $^mC_{eo}$ $^mC_{ds}$ $^mC_{ds}$ $T_{ds}$ $^mC_{ds}$ $A_{ds}$ $^mC_{ds}$ $^mC_{ds}$ $G_{ds}$ $A_{eo}$ $G_{eo}$ $A_{es}$ $G_{es}$ $G_e$ | 1902 | 1921 | 45.6 | 250 |
| 628548 | $^mC_{es}$ $G_{eo}$ $G_{eo}$ $^mC_{eo}$ $G_{eo}$ $G_{ds}$ $^mC_{ds}$ $G_{ds}$ $G_{ds}$ $^mC_{ds}$ $^mC_{ds}$ $A_{ds}$ $T_{ds}$ $T_{ds}$ $T_{ds}$ $T_{eo}$ $^mC_{eo}$ $^mC_{es}$ $G_{es}$ $G_e$ | 1934 | 1953 | 69.6 | 251 |
| 628552 | $T_{es}$ $G_{eo}$ $G_{eo}$ $A_{eo}$ $G_{eo}$ $^mC_{ds}$ $A_{ds}$ $G_{ds}$ $T_{ds}$ $^mC_{ds}$ $T_{ds}$ $^mC_{ds}$ $T_{ds}$ $^mC_{ds}$ $^mC_{ds}$ $T_{eo}$ $^mC_{eo}$ $^mC_{es}$ $T_{es}$ $^mC_e$ | 1989 | 2008 | 40.3 | 252 |
| 628740 | $T_{es}$ $T_{eo}$ $^mC_{eo}$ $A_{eo}$ $T_{eo}$ $G_{ds}$ $G_{ds}$ $A_{ds}$ $A_{ds}$ $T_{ds}$ $G_{ds}$ $G_{ds}$ $G_{ds}$ $^mC_{ds}$ $G_{ds}$ $A_{eo}$ $G_{eo}$ $A_{es}$ $A_{es}$ $G_e$ | 2547 | 2566 | 23.4 | 253 |
| 628744 | $A_{es}$ $^mC_{eo}$ $A_{eo}$ $G_{eo}$ $A_{eo}$ $G_{ds}$ $G_{ds}$ $^mC_{ds}$ $A_{ds}$ $G_{ds}$ $G_{ds}$ $G_{ds}$ $^mC_{ds}$ $A_{ds}$ $G_{ds}$ $G_{eo}$ $^mC_{eo}$ $A_{es}$ $^mC_{es}$ $G_e$ | 4561 | 4580 | 62.6 | 254 |
| 628748 | $A_{es}$ $A_{eo}$ $G_{eo}$ $A_{eo}$ $T_{eo}$ $T_{ds}$ $^mC_{ds}$ $A_{ds}$ $T_{ds}$ $G_{ds}$ $^mC_{ds}$ $T_{ds}$ $T_{ds}$ $G_{ds}$ $T_{ds}$ $T_{eo}$ $A_{eo}$ $G_{es}$ $A_{es}$ $A_e$ | 7090 | 7109 | 39.7 | 255 |
| 628556 | $T_{es}$ $^mC_{eo}$ $A_{eo}$ $A_{eo}$ $A_{eo}$ $G_{ds}$ $^mC_{ds}$ $A_{ds}$ $G_{ds}$ $G_{ds}$ $A_{ds}$ $A_{ds}$ $^mC_{ds}$ $T_{ds}$ $G_{ds}$ $G_{eo}$ $T_{eo}$ $G_{es}$ $A_{es}$ $G_e$ | 7316 | 7335 | 40.7 | 256 |
| 628560 | $G_{es}$ $G_{eo}$ $T_{eo}$ $^mC_{eo}$ $T_{eo}$ $A_{ds}$ $^mC_{ds}$ $A_{ds}$ $G_{ds}$ $A_{ds}$ $A_{ds}$ $G_{ds}$ $^mC_{ds}$ $A_{ds}$ $A_{ds}$ $G_{eo}$ $G_{eo}$ $T_{es}$ $G_{es}$ $T_e$ | 7359 | 7378 | 76.3 | 257 |
| 628564 | $^mC_{es}$ $A_{eo}$ $T_{eo}$ $^mC_{eo}$ $^mC_{ds}$ $A_{ds}$ $G_{ds}$ $^mC_{ds}$ $T_{ds}$ $A_{ds}$ $^mC_{ds}$ $^mC_{ds}$ $A_{ds}$ $T_{ds}$ $G_{eo}$ $G_{eo}$ $A_{es}$ $A_{es}$ $T_e$ | 7391 | 7410 | 63.3 | 258 |
| 628752 | $^mC_{es}$ $A_{eo}$ $^mC_{eo}$ $^mC_{eo}$ $A_{eo}$ $T_{ds}$ $^mC_{ds}$ $^mC_{ds}$ $T_{ds}$ $G_{ds}$ $A_{ds}$ $G_{ds}$ $G_{ds}$ $^mC_{ds}$ $^mC_{ds}$ $A_{eo}$ $G_{eo}$ $G_{es}$ $^mC_{es}$ $A_e$ | 9908 | 9927 | 86.2 | 259 |
| 628756 | $T_{es}$ $A_{eo}$ $A_{eo}$ $^mC_{eo}$ $T_{eo}$ $T_{ds}$ $T_{ds}$ $T_{ds}$ $T_{ds}$ $T_{ds}$ $^mC_{ds}$ $T_{ds}$ $A_{ds}$ $T_{ds}$ $T_{ds}$ $A_{eo}$ $T_{eo}$ $T_{es}$ $A_{es}$ $T_e$ | 12623 | 12642 | 14.8 | 260 |
| 628760 | $A_{es}$ $^mC_{eo}$ $A_{eo}$ $G_{eo}$ $T_{eo}$ $^mC_{ds}$ $A_{ds}$ $^mC_{ds}$ $A_{ds}$ $G_{ds}$ $A_{ds}$ $A_{ds}$ $^mC_{ds}$ $A_{ds}$ $A_{ds}$ $^mC_{eo}$ $A_{eo}$ $A_{es}$ $A_{es}$ $G_e$ | 14890 | 14909 | 80.6 | 261 |
| 628764 | $G_{es}$ $G_{eo}$ $^mC_{eo}$ $^mC_{eo}$ $T_{eo}$ $A_{ds}$ $A_{ds}$ $T_{ds}$ $T_{ds}$ $T_{ds}$ $T_{ds}$ $T_{ds}$ $T_{ds}$ $A_{ds}$ $T_{ds}$ $^mC_{eo}$ $T_{eo}$ $T_{es}$ $T_{es}$ $G_e$ | 17865 | 17884 | 80.6 | 262 |
| 628768 | $A_{es}$ $^mC_{eo}$ $A_{eo}$ $G_{eo}$ $G_{eo}$ $G_{ds}$ $T_{ds}$ $T_{ds}$ $G_{ds}$ $T_{ds}$ $A_{ds}$ $G_{ds}$ $^mC_{ds}$ $^mC_{ds}$ $A_{ds}$ $T_{eo}$ $^mC_{eo}$ $A_{es}$ $G_{es}$ $^mC_e$ | 20758 | 20777 | 91.0 | 263 |
| 628772 | $G_{es}$ $A_{eo}$ $T_{eo}$ $^mC_{eo}$ $A_{eo}$ $^mC_{ds}$ $T_{ds}$ $G_{ds}$ $G_{ds}$ $A_{ds}$ $A_{ds}$ $^mC_{ds}$ $A_{ds}$ $^mC_{ds}$ $A_{ds}$ $A_{eo}$ $T_{eo}$ $G_{es}$ $G_{es}$ $T_e$ | 22839 | 22858 | 91.6 | 264 |
| 628776 | $G_{es}$ $G_{eo}$ $A_{eo}$ $A_{eo}$ $G_{eo}$ $A_{ds}$ $G_{ds}$ $A_{ds}$ $A_{ds}$ $A_{ds}$ $G_{ds}$ $A_{ds}$ $A_{ds}$ $G_{ds}$ $G_{eo}$ $G_{eo}$ $^mC_{es}$ $A_{es}$ $^mC_e$ | 25437 | 25456 | 43.3 | 265 |
| 628780 | $^mC_{es}$ $A_{eo}$ $T_{eo}$ $T_{eo}$ $T_{eo}$ $A_{ds}$ $A_{ds}$ $T_{ds}$ $A_{ds}$ $A_{ds}$ $A_{ds}$ $T_{ds}$ $A_{ds}$ $A_{ds}$ $A_{ds}$ $T_{eo}$ $^mC_{eo}$ $^mC_{es}$ $^mC_{es}$ $T_e$ | 27672 | 27691 | 21.9 | 266 |

TABLE 4-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628784 | T$_{es}$ T$_{eo}$ T$_{eo}$ A$_{eo}$ $^m$C$_{eo}$ $^m$C$_{ds}$ A$_{ds}$ G$_{ds}$ T$_{ds}$ G$_{ds}$ $^m$C$_{ds}$ $^m$C$_{ds}$ A$_{ds}$ T$_{ds}$ T$_{ds}$ T$_{eo}$ T$_{eo}$ T$_{es}$ $^m$C$_{es}$ $^m$C$_e$ | 30227 | 30246 | 58.2 | 267 |
| 628788 | $^m$C$_{es}$ A$_{eo}$ G$_{eo}$ $^m$C$_{eo}$ A$_{eo}$ A$_{ds}$ A$_{ds}$ T$_{ds}$ T$_{ds}$ T$_{ds}$ $^m$C$_{ds}$ T$_{ds}$ G$_{ds}$ T$_{ds}$ G$_{ds}$ G$_{eo}$ T$_{eo}$ T$_{es}$ T$_{es}$ T$_e$ | 32258 | 32277 | 94.0 | 268 |
| 628792 | G$_{es}$ $^m$C$_{eo}$ T$_{eo}$ $^m$C$_{eo}$ T$_{eo}$ $^m$C$_{ds}$ A$_{ds}$ G$_{ds}$ A$_{ds}$ $^m$C$_{ds}$ $^m$C$_{ds}$ A$_{ds}$ G$_{ds}$ A$_{ds}$ $^m$C$_{ds}$ $^m$C$_{eo}$ A$_{eo}$ G$_{es}$ A$_{es}$ $^m$C$_e$ | 34773 | 34792 | 78.3 | 269 |
| 628796 | A$_{es}$ $^m$C$_{eo}$ A$_{eo}$ G$_{eo}$ $^m$C$_{eo}$ T$_{ds}$ G$_{ds}$ A$_{ds}$ T$_{ds}$ G$_{ds}$ A$_{ds}$ G$_{ds}$ G$_{ds}$ A$_{ds}$ G$_{ds}$ G$_{eo}$ G$_{eo}$ T$_{es}$ G$_{es}$ G$_e$ | 37542 | 37561 | 11.6 | 270 |
| 628800 | T$_{es}$ A$_{eo}$ $^m$C$_{eo}$ A$_{eo}$ $^m$C$_{eo}$ A$_{ds}$ A$_{ds}$ A$_{ds}$ T$_{ds}$ A$_{ds}$ $^m$C$_{ds}$ T$_{ds}$ A$_{ds}$ A$_{ds}$ G$_{ds}$ $^m$C$_{ds}$ $^m$C$_{eo}$ A$_{es}$ $^m$C$_{es}$ A$_e$ | 39572 | 39591 | 76.1 | 271 |
| 628804 | A$_{es}$ $^m$C$_{eo}$ T$_{eo}$ G$_{eo}$ $^m$C$_{eo}$ $^m$C$_{ds}$ A$_{ds}$ $^m$C$_{ds}$ $^m$C$_{ds}$ A$_{ds}$ $^m$C$_{ds}$ $^m$C$_{ds}$ A$_{ds}$ T$_{ds}$ G$_{ds}$ A$_{eo}$ $^m$C$_{eo}$ T$_{es}$ A$_{es}$ A$_e$ | 41573 | 41592 | 63.7 | 272 |
| 628808 | G$_{es}$ T$_{eo}$ T$_{eo}$ A$_{eo}$ G$_{eo}$ A$_{ds}$ A$_{ds}$ A$_{ds}$ G$_{ds}$ T$_{ds}$ T$_{ds}$ G$_{ds}$ A$_{ds}$ T$_{ds}$ T$_{ds}$ T$_{ds}$ T$_{eo}$ T$_{eo}$ T$_{es}$ $^m$C$_{es}$ T$_e$ | 44142 | 44161 | 80.7 | 273 |
| 628812 | A$_{es}$ T$_{eo}$ A$_{eo}$ $^m$C$_{eo}$ T$_{eo}$ $^m$C$_{ds}$ A$_{ds}$ $^m$C$_{ds}$ A$_{ds}$ T$_{ds}$ G$_{ds}$ G$_{ds}$ T$_{ds}$ G$_{ds}$ G$_{ds}$ A$_{eo}$ G$_{eo}$ A$_{es}$ A$_{es}$ A$_e$ | 46268 | 46287 | 52.5 | 274 |
| 628816 | G$_{es}$ A$_{eo}$ G$_{eo}$ A$_{eo}$ A$_{eo}$ G$_{ds}$ A$_{ds}$ A$_{ds}$ T$_{ds}$ G$_{ds}$ G$_{ds}$ A$_{ds}$ A$_{ds}$ G$_{ds}$ G$_{ds}$ G$_{eo}$ A$_{eo}$ G$_{es}$ A$_{es}$ A$_e$ | 48363 | 48382 | 21.0 | 275 |
| 628820 | T$_{es}$ A$_{eo}$ G$_{eo}$ A$_{eo}$ G$_{eo}$ G$_{ds}$ G$_{ds}$ T$_{ds}$ G$_{ds}$ G$_{ds}$ G$_{ds}$ A$_{ds}$ G$_{ds}$ G$_{ds}$ G$_{ds}$ A$_{ds}$ A$_{eo}$ $^m$C$_{eo}$ A$_{es}$ G$_{es}$ G$_e$ | 50365 | 50384 | 25.7 | 276 |
| 628824 | $^m$C$_{es}$ T$_{eo}$ T$_{eo}$ A$_{eo}$ G$_{eo}$ A$_{ds}$ A$_{ds}$ $^m$C$_{ds}$ A$_{ds}$ A$_{ds}$ A$_{ds}$ G$_{ds}$ A$_{ds}$ G$_{ds}$ A$_{ds}$ A$_{eo}$ G$_{eo}$ A$_{es}$ A$_{es}$ T$_e$ | 53052 | 53071 | -5.2 | 277 |
| 628828 | G$_{es}$ A$_{eo}$ $^m$C$_{eo}$ A$_{eo}$ $^m$C$_{eo}$ T$_{ds}$ G$_{ds}$ A$_{ds}$ $^m$C$_{ds}$ A$_{ds}$ $^m$C$_{ds}$ T$_{ds}$ G$_{ds}$ T$_{ds}$ G$_{ds}$ $^m$C$_{eo}$ A$_{eo}$ T$_{es}$ G$_{es}$ A$_e$ | 55069 | 55088 | 67.5 | 278 |
| 628832 | G$_{es}$ G$_{eo}$ A$_{eo}$ G$_{eo}$ T$_{eo}$ T$_{ds}$ A$_{ds}$ $^m$C$_{ds}$ $^m$C$_{ds}$ A$_{ds}$ T$_{ds}$ A$_{ds}$ T$_{ds}$ G$_{ds}$ A$_{ds}$ $^m$C$_{eo}$ $^m$C$_{eo}$ T$_{es}$ G$_{es}$ G$_e$ | 57122 | 57141 | 68.6 | 279 |
| 628836 | $^m$C$_{es}$ G$_{eo}$ T$_{eo}$ A$_{eo}$ A$_{eo}$ G$_{ds}$ $^m$C$_{ds}$ T$_{ds}$ T$_{ds}$ $^m$C$_{ds}$ T$_{ds}$ A$_{ds}$ G$_{ds}$ $^m$C$_{ds}$ A$_{ds}$ A$_{eo}$ G$_{eo}$ A$_{es}$ A$_{es}$ G$_e$ | 59723 | 59742 | 70.0 | 280 |
| 628840 | G$_{es}$ G$_{eo}$ T$_{eo}$ A$_{eo}$ A$_{eo}$ A$_{ds}$ A$_{ds}$ A$_{ds}$ T$_{ds}$ G$_{ds}$ A$_{ds}$ T$_{ds}$ A$_{ds}$ A$_{ds}$ A$_{ds}$ A$_{eo}$ A$_{eo}$ A$_{es}$ $^m$C$_{es}$ G$_e$ | 61802 | 61821 | -9.7 | 281 |
| 628844 | A$_{es}$ G$_{eo}$ $^m$C$_{eo}$ $^m$C$_{eo}$ T$_{eo}$ T$_{ds}$ $^m$C$_{ds}$ T$_{ds}$ $^m$C$_{ds}$ $^m$C$_{ds}$ T$_{ds}$ G$_{ds}$ $^m$C$_{es}$ $^m$C$_{es}$ T$_{ds}$ $^m$C$_{eo}$ A$_{eo}$ G$_{es}$ $^m$C$_{es}$ T$_e$ | 63907 | 63926 | 82.8 | 282 |
| 628848 | A$_{es}$ G$_{eo}$ A$_{eo}$ A$_{eo}$ G$_{eo}$ $^m$C$_{ds}$ A$_{ds}$ G$_{ds}$ $^m$C$_{ds}$ A$_{ds}$ G$_{ds}$ $^m$C$_{ds}$ $^m$C$_{ds}$ A$_{ds}$ $^m$C$_{ds}$ $^m$C$_{eo}$ T$_{eo}$ G$_{es}$ $^m$C$_{es}$ G$_e$ | 65932 | 65951 | 14.3 | 283 |
| 628568 | T$_{es}$ G$_{eo}$ G$_{eo}$ T$_{eo}$ $^m$C$_{eo}$ T$_{ds}$ T$_{ds}$ $^m$C$_{ds}$ T$_{ds}$ G$_{ds}$ A$_{ds}$ $^m$C$_{ds}$ T$_{ds}$ T$_{ds}$ T$_{ds}$ T$_{eo}$ $^m$C$_{eo}$ T$_{es}$ T$_{es}$ $^m$C$_e$ | 67056 | 67075 | 56.8 | 284 |
| 628572 | $^m$C$_{ds}$ A$_{eo}$ $^m$C$_{eo}$ $^m$C$_{eo}$ T$_{eo}$ T$_{ds}$ T$_{ds}$ T$_{ds}$ T$_{ds}$ A$_{ds}$ A$_{ds}$ A$_{ds}$ $^m$C$_{ds}$ T$_{ds}$ T$_{ds}$ G$_{eo}$ A$_{eo}$ G$_{es}$ G$_{es}$ G$_e$ | 67102 | 67121 | 74.9 | 285 |
| 628576 | T$_{es}$ T$_{eo}$ T$_{eo}$ $^m$C$_{eo}$ T$_{eo}$ $^m$C$_{ds}$ T$_{ds}$ T$_{ds}$ $^m$C$_{ds}$ T$_{ds}$ T$_{ds}$ T$_{ds}$ $^m$C$_{ds}$ T$_{ds}$ T$_{ds}$ A$_{eo}$ T$_{eo}$ $^m$C$_{es}$ T$_{es}$ T$_e$ | 67126 | 67145 | 47.3 | 286 |
| 628580 | T$_{es}$ $^m$C$_{eo}$ A$_{eo}$ T$_{eo}$ G$_{eo}$ $^m$C$_{ds}$ T$_{ds}$ T$_{ds}$ G$_{ds}$ $^m$C$_{ds}$ $^m$C$_{ds}$ $^m$C$_{ds}$ T$_{ds}$ $^m$C$_{ds}$ T$_{ds}$ T$_{eo}$ T$_{eo}$ $^m$C$_{es}$ T$_{es}$ $^m$C$_e$ | 67140 | 67159 | 57.4 | 287 |
| 628584 | T$_{es}$ G$_{eo}$ A$_{eo}$ T$_{eo}$ G$_{eo}$ G$_{ds}$ $^m$C$_{ds}$ T$_{ds}$ G$_{ds}$ $^m$C$_{ds}$ A$_{ds}$ $^m$C$_{ds}$ G$_{ds}$ G$_{ds}$ G$_{ds}$ $^m$C$_{eo}$ T$_{eo}$ $^m$C$_{es}$ A$_{es}$ T$_e$ | 67156 | 67175 | 58.1 | 288 |
| 628588 | $^m$C$_{es}$ A$_{eo}$ G$_{eo}$ $^m$C$_{eo}$ A$_{eo}$ G$_{ds}$ A$_{ds}$ G$_{ds}$ T$_{ds}$ G$_{ds}$ G$_{ds}$ G$_{ds}$ T$_{ds}$ G$_{ds}$ G$_{ds}$ $^m$C$_{eo}$ T$_{eo}$ G$_{es}$ A$_{es}$ T$_e$ | 67172 | 67191 | 10.9 | 289 |
| 628592 | T$_{es}$ G$_{eo}$ A$_{eo}$ T$_{eo}$ G$_{eo}$ T$_{ds}$ $^m$C$_{ds}$ T$_{ds}$ $^m$C$_{ds}$ T$_{ds}$ A$_{ds}$ $^m$C$_{ds}$ T$_{ds}$ T$_{ds}$ T$_{ds}$ G$_{eo}$ $^m$C$_{eo}$ $^m$C$_{es}$ T$_{es}$ G$_e$ | 67204 | 67223 | 37.9 | 290 |
| 628596 | $^m$C$_{es}$ A$_{eo}$ G$_{eo}$ A$_{eo}$ A$_{eo}$ G$_{ds}$ $^m$C$_{ds}$ T$_{ds}$ T$_{ds}$ $^m$C$_{ds}$ $^m$C$_{ds}$ G$_{ds}$ G$_{ds}$ $^m$C$_{ds}$ A$_{ds}$ $^m$C$_{eo}$ A$_{eo}$ G$_{es}$ $^m$C$_{es}$ $^m$C$_e$ | 67244 | 67263 | 16.0 | 291 |

TABLE 4-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628600 | $G_{es} G_{eo} G_{eo} T_{eo} {}^mC_{eo} {}^mC_{es} {}^mC_{es} {}^mC_{es} G_{ds} G_{ds} T_{ds} {}^mC_{ds} A_{ds} {}^mC_{ds} G_{ds} G_{eo} A_{eo} T_{es} G_{es} A_e$ | 67288 | 67307 | 50.5 | 292 |
| 628604 | $G_{es} {}^mC_{eo} T_{eo} T_{eo} A_{eo} A_{ds} G_{ds} {}^mC_{ds} T_{ds} T_{ds} {}^mC_{es} {}^mC_{es} G_{ds} T_{ds} G_{ds} T_{eo} {}^mC_{eo} {}^mC_{es} A_{es} G_e$ | 67337 | 67356 | 59.6 | 293 |
| 628608 | $A_{es} T_{eo} A_{eo} {}^mC_{eo} T_{eo} T_{ds} {}^mC_{es} {}^mC_{es} {}^mC_{es} A_{ds} G_{ds} {}^mC_{ds} A_{ds} G_{ds} A_{ds} G_{eo} {}^mC_{eo} G_{es} G_{es} {}^mC_e$ | 67369 | 67388 | 19.9 | 294 |
| 628852 | $A_{es} G_{eo} {}^mC_{eo} A_{eo} A_{eo} {}^mC_{es} {}^mC_{es} A_{ds} A_{ds} A_{ds} G_{ds} A_{ds} G_{ds} T_{ds} {}^mC_{es} A_{eo} G_{eo} G_{es} {}^mC_{es} {}^mC_e$ | 67934 | 67953 | 76.1 | 295 |
| 628612 | $A_{es} {}^mC_{eo} T_{eo} T_{eo} T_{eo} A_{ds} G_{ds} A_{ds} G_{ds} {}^mC_{ds} G_{ds} A_{ds} A_{ds} A_{ds} G_{ds} G_{eo} {}^mC_{eo} T_{es} T_{es} T_e$ | 68172 | 68191 | 36.2 | 296 |
| 628616 | $T_{es} T_{eo} T_{eo} T_{eo} {}^mC_{eo} G_{ds} A_{ds} A_{ds} G_{ds} T_{ds} A_{ds} {}^mC_{es} G_{ds} {}^mC_{es} A_{ds} A_{eo} T_{eo} {}^mC_{es} A_{es} A_e$ | 68196 | 68215 | 41.9 | 297 |
| 628620 | ${}^mC_{es} {}^mC_{eo} A_{eo} G_{eo} G_{eo} G_{ds} A_{ds} T_{ds} G_{ds} T_{ds} G_{ds} T_{ds} {}^mC_{ds} G_{ds} {}^mC_{ds} {}^mC_{eo} T_{eo} A_{es} {}^mC_{es} {}^mC_e$ | 68216 | 68235 | 62.3 | 298 |
| 628624 | ${}^mC_{es} {}^mC_{eo} A_{eo} G_{eo} T_{eo} T_{ds} A_{ds} {}^mC_{ds} {}^mC_{ds} G_{ds} T_{ds} G_{ds} A_{ds} A_{ds} G_{ds} T_{eo} {}^mC_{eo} A_{es} A_{es} A_e$ | 68247 | 68266 | 40.4 | 299 |
| 628628 | $T_{es} G_{eo} G_{eo} G_{eo} {}^mC_{eo} T_{ds} T_{ds} {}^mC_{ds} T_{ds} T_{ds} A_{ds} G_{ds} G_{ds} T_{ds} G_{ds} G_{eo} T_{eo} T_{es} T_{es} {}^mC_e$ | 68294 | 68313 | 53.5 | 300 |
| 628632 | $G_{es} T_{eo} G_{eo} G_{eo} T_{eo} G_{ds} {}^mC_{ds} {}^mC_{ds} G_{ds} {}^mC_{ds} T_{ds} {}^mC_{ds} {}^mC_{ds} {}^mC_{ds} T_{ds} T_{eo} T_{eo} G_{es} G_{es} G_e$ | 68355 | 68374 | 65.8 | 301 |
| 628636 | $T_{es} {}^mC_{eo} T_{eo} {}^mC_{eo} {}^mC_{eo} A_{ds} G_{ds} G_{ds} A_{ds} {}^mC_{ds} {}^mC_{ds} {}^mC_{ds} T_{ds} T_{ds} T_{ds} T_{eo} {}^mC_{eo} A_{es} {}^mC_{es} {}^mC_e$ | 68408 | 68427 | 38.7 | 302 |
| 628640 | $G_{es} A_{eo} {}^mC_{eo} A_{eo} A_{eo} G_{ds} G_{ds} A_{ds} G_{ds} {}^mC_{ds} T_{ds} T_{ds} {}^mC_{ds} {}^mC_{ds} {}^mC_{ds} A_{eo} G_{eo} G_{es} A_{es} {}^mC_e$ | 68431 | 68450 | 57.4 | 303 |
| 628644 | ${}^mC_{es} {}^mC_{eo} {}^mC_{eo} T_{eo} G_{eo} G_{ds} {}^mC_{ds} G_{ds} A_{ds} A_{ds} G_{ds} T_{ds} T_{ds} T_{ds} G_{ds} A_{eo} A_{eo} A_{es} A_{es} G_e$ | 68458 | 68477 | 37.8 | 304 |
| 628648 | ${}^mC_{es} {}^mC_{eo} {}^mC_{eo} {}^mC_{eo} T_{eo} {}^mC_{ds} A_{ds} G_{ds} {}^mC_{ds} {}^mC_{ds} T_{ds} T_{ds} G_{ds} {}^mC_{ds} {}^mC_{ds} {}^mC_{eo} {}^mC_{eo} {}^mC_{es} T_{es} G_e$ | 68473 | 68492 | 25.0 | 305 |
| 628652 | $T_{es} G_{eo} G_{eo} G_{eo} T_{eo} G_{ds} G_{ds} A_{ds} T_{ds} G_{ds} T_{ds} G_{ds} G_{ds} T_{ds} G_{ds} G_{eo} {}^mC_{eo} {}^mC_{es} {}^mC_{es} {}^mC_e$ | 68496 | 68515 | 13.6 | 306 |
| 628656 | ${}^mC_{es} G_{eo} G_{eo} {}^mC_{eo} {}^mC_{eo} T_{ds} {}^mC_{ds} A_{ds} G_{ds} {}^mC_{ds} T_{ds} T_{ds} T_{ds} T_{ds} {}^mC_{ds} G_{eo} {}^mC_{eo} T_{es} T_{es} {}^mC_e$ | 68543 | 68562 | 59.4 | 307 |
| 628660 | $T_{es} {}^mC_{eo} G_{eo} G_{eo} {}^mC_{eo} {}^mC_{ds} {}^mC_{ds} {}^mC_{ds} G_{ds} T_{ds} T_{ds} T_{ds} {}^mC_{ds} T_{ds} T_{ds} G_{eo} G_{eo} G_{ds} A_{es} A_e$ | 68575 | 68594 | 33.8 | 308 |
| 628664 | $G_{es} {}^mC_{eo} G_{eo} G_{eo} {}^mC_{eo} A_{ds} G_{ds} {}^mC_{ds} G_{ds} G_{ds} {}^mC_{ds} T_{ds} G_{ds} {}^mC_{ds} {}^mC_{ds} A_{eo} {}^mC_{eo} {}^mC_{es} A_{es} {}^mC_e$ | 68607 | 68626 | 31.0 | 309 |
| *628668 | $A_{es} A_{eo} G_{eo} A_{eo} {}^mC_{eo} T_{ds} {}^mC_{ds} {}^mC_{ds} T_{ds} T_{ds} {}^mC_{ds} A_{ds} {}^mC_{ds} G_{ds} G_{ds} {}^mC_{eo} T_{eo} T_{es} T_{es} {}^mC_e$ | 68639 | 68658 | 69.2 | 310 |
| *628672 | $G_{es} G_{eo} T_{eo} {}^mC_{eo} T_{eo} {}^mC_{ds} {}^mC_{ds} T_{ds} G_{ds} {}^mC_{ds} A_{ds} {}^mC_{ds} A_{ds} G_{ds} A_{ds} T_{eo} {}^mC_{eo} G_{es} G_{es} A_e$ | 68662 | 68681 | 95.2 | 311 |
| *628676 | $G_{es} {}^mC_{eo} T_{eo} G_{eo} A_{eo} {}^mC_{ds} {}^mC_{ds} G_{ds} T_{ds} {}^mC_{ds} T_{ds} {}^mC_{ds} {}^mC_{ds} {}^mC_{ds} G_{ds} G_{eo} G_{eo} T_{es} {}^mC_{es} T_e$ | 68704 | 68723 | 40.4 | 312 |
| 628680 | ${}^mC_{es} G_{eo} A_{eo} G_{eo} G_{eo} G_{ds} T_{ds} G_{ds} G_{ds} A_{ds} {}^mC_{ds} A_{ds} {}^mC_{ds} {}^mC_{ds} A_{ds} G_{eo} {}^mC_{eo} A_{es} G_{es} G_e$ | 68750 | 68769 | 37.2 | 313 |
| 628684 | $A_{es} {}^mC_{eo} A_{eo} G_{eo} G_{eo} T_{ds} {}^mC_{ds} T_{ds} T_{ds} {}^mC_{ds} A_{ds} G_{ds} T_{ds} {}^mC_{ds} {}^mC_{ds} T_{eo} T_{eo} T_{es} {}^mC_{es} {}^mC_e$ | 68782 | 68801 | 63.5 | 314 |
| 628688 | ${}^mC_{es} T_{eo} G_{eo} {}^mC_{eo} T_{eo} {}^mC_{ds} T_{ds} {}^mC_{ds} T_{ds} {}^mC_{ds} G_{ds} {}^mC_{ds} T_{ds} T_{ds} T_{eo} T_{eo} {}^mC_{es} {}^mC_{es} G_e$ | 68814 | 68833 | 84.1 | 315 |
| 628692 | ${}^mC_{es} T_{eo} G_{eo} A_{eo} G_{eo} T_{ds} G_{ds} G_{ds} T_{ds} G_{ds} G_{ds} T_{ds} G_{ds} A_{ds} T_{ds} G_{eo} G_{eo} T_{es} G_{es} G_e$ | 68885 | 68904 | 11.9 | 316 |

TABLE 4-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628696 | $^mC_{es}$ $T_{eo}$ $T_{eo}$ $^mC_{eo}$ $T_{eo}$ $^mC_{ds}$ $^mC_{ds}$ $T_{ds}$ $^mC_{ds}$ $T_{ds}$ $T_{ds}$ $T_{ds}$ $G_{ds}$ $^mC_{ds}$ $A_{ds}$ $G_{eo}$ $A_{eo}$ $^mC_{es}$ $G_{es}$ $^mC_{e}$ | 69016 | 69035 | 70.9 | 317 |
| 628700 | $^mC_{es}$ $^mC_{eo}$ $G_{eo}$ $T_{eo}$ $^mC_{eo}$ $G_{ds}$ $^mC_{ds}$ $T_{ds}$ $^mC_{ds}$ $T_{ds}$ $^mC_{ds}$ $^mC_{ds}$ $A_{ds}$ $G_{ds}$ $T_{ds}$ $G_{eo}$ $A_{eo}$ $G_{ds}$ $^mC_{es}$ $^mC_{e}$ | 69048 | 69067 | 71.6 | 318 |
| 628704 | $G_{es}$ $G_{eo}$ $^mC_{eo}$ $A_{eo}$ $A_{eo}$ $^mC_{ds}$ $^mC_{ds}$ $G_{ds}$ $^mC_{ds}$ $G_{ds}$ $G_{ds}$ $G_{ds}$ $^mC_{ds}$ $T_{ds}$ $G_{ds}$ $A_{eo}$ $G_{eo}$ $T_{es}$ $^mC_{es}$ $T_{e}$ | 69088 | 69107 | 72.3 | 319 |
| 628708 | $^mC_{es}$ $^mC_{eo}$ $G_{eo}$ $T_{eo}$ $G_{eo}$ $G_{ds}$ $^mC_{ds}$ $G_{ds}$ $G_{ds}$ $^mC_{ds}$ $G_{ds}$ $G_{ds}$ $T_{ds}$ $G_{ds}$ $G_{ds}$ $^mC_{eo}$ $A_{eo}$ $A_{es}$ $^mC_{es}$ $^mC_{e}$ | 69101 | 69120 | 32.3 | 320 |
| 628712 | $T_{es}$ $A_{eo}$ $^mC_{eo}$ $T_{eo}$ $T_{eo}$ $T_{ds}$ $T_{ds}$ $^mC_{ds}$ $T_{ds}$ $G_{ds}$ $^mC_{ds}$ $G_{ds}$ $G_{ds}$ $^mC_{ds}$ $^mC_{ds}$ $G_{eo}$ $T_{eo}$ $G_{es}$ $G_{es}$ $^mC_{e}$ | 69114 | 69133 | 55.9 | 321 |
| 628716 | $T_{es}$ $^mC_{eo}$ $T_{eo}$ $T_{eo}$ $T_{eo}$ $G_{ds}$ $^mC_{ds}$ $G_{ds}$ $^mC_{ds}$ $T_{ds}$ $^mC_{ds}$ $T_{ds}$ $^mC_{ds}$ $^mC_{ds}$ $^mC_{ds}$ $T_{eo}$ $^mC_{eo}$ $^mC_{es}$ $^mC_{es}$ $^mC_{e}$ | 69144 | 69163 | 52.4 | 322 |
| 628720 | $T_{es}$ $G_{eo}$ $T_{eo}$ $T_{eo}$ $T_{eo}$ $G_{ds}$ $G_{ds}$ $^mC_{ds}$ $^mC_{ds}$ $T_{ds}$ $T_{ds}$ $G_{ds}$ $G_{ds}$ $^mC_{ds}$ $A_{ds}$ $T_{eo}$ $G_{eo}$ $G_{ds}$ $A_{es}$ $G_{e}$ | 69176 | 69195 | 55.1 | 323 |
| 628724 | $A_{es}$ $A_{eo}$ $^mC_{eo}$ $T_{eo}$ $^mC_{eo}$ $T_{ds}$ $^mC_{ds}$ $T_{ds}$ $^mC_{ds}$ $G_{ds}$ $G_{ds}$ $T_{ds}$ $^mC_{ds}$ $A_{ds}$ $^mC_{ds}$ $G_{eo}$ $G_{eo}$ $G_{es}$ $^mC_{es}$ $G_{e}$ | 69220 | 69239 | 82.2 | 324 |
| 628728 | $T_{es}$ $G_{eo}$ $^mC_{eo}$ $T_{eo}$ $T_{eo}$ $T_{ds}$ $G_{ds}$ $^mC_{ds}$ $A_{ds}$ $A_{ds}$ $T_{ds}$ $^mC_{ds}$ $^mC_{ds}$ $G_{ds}$ $^mC_{ds}$ $T_{eo}$ $^mC_{eo}$ $^mC_{es}$ $G_{es}$ $T_{e}$ | 69252 | 69271 | 77.9 | 325 |
| 628732 | $A_{es}$ $G_{eo}$ $A_{eo}$ $G_{eo}$ $A_{eo}$ $^mC_{ds}$ $A_{ds}$ $A_{ds}$ $^mC_{ds}$ $A_{ds}$ $G_{ds}$ $^mC_{ds}$ $T_{ds}$ $G_{ds}$ $^mC_{ds}$ $^mC_{eo}$ $T_{eo}$ $T_{es}$ $T_{es}$ $A_{e}$ | 69284 | 69303 | 57.7 | 326 |
| 628736 | $G_{es}$ $A_{eo}$ $A_{eo}$ $G_{eo}$ $^mC_{eo}$ $T_{ds}$ $T_{ds}$ $T_{ds}$ $G_{ds}$ $T_{ds}$ $^mC_{ds}$ $A_{ds}$ $G_{ds}$ $A_{ds}$ $G_{ds}$ $^mC_{eo}$ $^mC_{eo}$ $^mC_{es}$ $T_{es}$ $A_{e}$ | 69316 | 69335 | 90.1 | 327 |

Superscript "m" indicates 5-methylcytosine.
Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

Example 2: Dose Response of Antisense Oligonucleotides Targeting MECP2 In Vitro MECP2 targeting antisense oligonucleotides selected from Tables 1-4 were tested for dose response analysis in HepG2 cells. Isis Number 141923 does not target MECP2 and was used as a negative control. Cells were electroporated with 0, 0.111, 0.333, 1.00, 3.00, or 9.00 µM antisense oligonucleotide, and MECP2 mRNA was analyzed as described in Example 1. Results are presented in Tables 5 and 6 below. Isis Numbers 141923 and 628749 were included in both data sets as references for comparison. The results show that the antisense oligonucleotides targeting MECP2 inhibited MECP2 mRNA expression in a dose dependent manner.

TABLE 5

Dose repsonse in vitro

| | % Inhibition | | | | | |
|---|---|---|---|---|---|---|
| Isis No. | 0.111 µM | 0.333 µM | 1.00 µM | 3.00 µM | 9.00 µM | SEQ ID NO: |
| 141923 | 101.7 | 124.0 | 97.3 | 105.3 | 70.6 | 328 |
| 628688 | 89.1 | 73.1 | 47.8 | 24.3 | 17.0 | 315 |
| 628724 | 83.6 | 76.8 | 41.2 | 17.4 | 14.1 | 324 |
| 628736 | 84.6 | 68.9 | 36.3 | 21.4 | 9.1 | 327 |
| 628749 | 63.8 | 36.4 | 19.3 | 7.7 | 3.7 | 103 |
| 628751 | 102.3 | 77.4 | 39.2 | 19.5 | 8.3 | 25 |
| 628752 | 76.0 | 77.7 | 47.4 | 28.0 | 18.4 | 259 |
| 628763 | 63.5 | 37.1 | 11.5 | 8.1 | 6.7 | 28 |
| 628767 | 82.2 | 56.7 | 33.0 | 16.0 | 12.0 | 29 |
| 628768 | 98.4 | 68.4 | 43.7 | 21.7 | 11.0 | 263 |
| 628772 | 84.3 | 60.6 | 34.4 | 13.7 | 5.4 | 264 |
| 628775 | 84.3 | 62.4 | 37.0 | 15.9 | 6.3 | 31 |
| 628787 | 81.8 | 60.5 | 38.6 | 26.6 | 10.0 | 34 |
| 628788 | 79.8 | 65.1 | 35.9 | 10.5 | 4.9 | 268 |
| 628811 | 69.1 | 46.8 | 20.6 | 22.1 | 4.2 | 40 |
| 628844 | 82.6 | 76.4 | 49.6 | 38.1 | 16.2 | 282 |

TABLE 6

Dose repsonse in vitro

| | % Inhibition | | | | | |
|---|---|---|---|---|---|---|
| Isis No. | 0.111 µM | 0.333 µM | 1.00 µM | 3.00 µM | 9.00 µM | SEQ ID NO: |
| 141923 | 116.6 | 123.1 | 120.7 | 119.6 | 119.0 | 328 |
| 628558 | 94.5 | 65.4 | 49.2 | 19.9 | 9.2 | 178 |
| 628614 | 85.8 | 84.4 | 60.5 | 28.9 | 15.3 | 218 |
| 628637 | 93.1 | 80.1 | 63.4 | 25.3 | 8.3 | 146 |

TABLE 6-continued

Dose repsonse in vitro

| | % Inhibition | | | | | |
|---|---|---|---|---|---|---|
| Isis No. | 0.111 μM | 0.333 μM | 1.00 μM | 3.00 μM | 9.00 μM | SEQ ID NO: |
| 628641 | 100.4 | 81.8 | 55.3 | 24.3 | 11.2 | 147 |
| 628690 | 101.7 | 77.9 | 51.5 | 28.0 | 16.4 | 237 |
| 628694 | 101.6 | 86.5 | 50.6 | 25.1 | 13.9 | 238 |
| 628742 | 103.3 | 73.6 | 48.8 | 20.1 | 14.7 | 175 |
| 628749 | 78.3 | 45.6 | 15.8 | 9.1 | 9.9 | 103 |
| 628757 | 88.6 | 70.5 | 39.0 | 21.7 | 13.5 | 105 |
| 628762 | 67.5 | 47.3 | 22.8 | 8.1 | 18.2 | 184 |
| 628766 | 119.8 | 77.5 | 65.6 | 31.5 | 18.0 | 185 |
| 628785 | 72.5 | 45.8 | 25.8 | 15.1 | 18.9 | 112 |
| 628786 | 85.6 | 55.5 | 36.0 | 17.3 | 10.6 | 190 |
| 628822 | 88.4 | 84.3 | 45.8 | 36.6 | 11.5 | 199 |
| 628833 | 90.6 | 70.1 | 55.2 | 32.1 | 10.8 | 124 |

Example 3: Effect of Antisense Oligonucleotides Targeting MECP2 In Vivo

Antisense oligonucleotides (ASOs) that target human Methyl CpG Binding Protein 2 (MECP2), the complement of GENBANK accession number NT_167198.1 truncated from 4203000 to 4283000, SEQ ID NO: 2, were synthesized using standard solid phase oligonucleotide synthetic methods. They are chimeric oligonucleotides ("gapmers"), composed of a central "gap" region consisting of 2'-deoxynucleotides, which is flanked on both sides (5' and 3') by "wings" that are composed of modified nucleotides. The internucleoside (backbone) linkages are phosphorothioate or phosphodiester throughout the oligonucleotides. The sequences and structures of the antisense oligonucleotides and their start and stop sites along SEQ ID NO: 2 are shown in the table below.

The antisense oligonucleotides were analyzed for their effects on MECP2 mRNA and protein levels in transgenic MECP2 duplication mice that overexpress wild type human MECP2 (F1 hybrid MECP2-TG1 mice(FVB/N×129)(Samaco et al., Nat Genet, 2012). At 8 weeks of age, FVB/N× 129 mice display hypoactivity in the open field test, increased anxiety in the open field and elevated plus maze tests, abnormal social behavior in the 3-chamber test, and increased motor coordination in the rotarod test. Seven week old MECP2-TG mice were given stereotactic intracerebral injection of 500 μg of an antisense oligonucleotide listed in Table 7 or saline into the right ventricle of the brain. Wild type mice were given stereotactic intracerebral injection of saline into the right ventricle of the brain as a control. Each group consisted of two or three mice. Two weeks following the injection, the mice were sacrificed, and cortical brain samples were collected for analysis of MECP2 mRNA and protein levels. MECP2 and GAPDH protein levels were analyzed by western blot performed on the cortical sample lysates. Rabbit antiserum raised against the N-terminus of MECP2 and mouse anti-GAPDH 6C5 (Advanced Immunochemicals, Long Beach, Calif.) were used as the primary antibodies. Western blot images were quantified using Image J software, and the MECP2 protein levels normalized to GAPDH levels are shown in Table 8 below.

Total MECP2 mRNA, human MECP2 mRNA (both the e1 and e2 isoforms), and mouse MECP2 mRNA (both the e1 and e2 isoforms) were separately analyzed by RT-qPCR. The primers common to human and mouse used for total MECP2 mRNA were: 5'-TATTTGATCAATCCCCAGGG-3', SEQ ID NO: 3, and 5'-CTCCCTCTCCCAGTTACCGT-3', SEQ ID NO: 4. The human specific primers used for MECP2-e1 were 5'-AGGAGAGACTGGAAGAAAAGTC-3', SEQ ID NO: 5, and 5'-CTTGAGGGGTTTGTCCTTGA-3', SEQ ID NO: 6. The human specific primers used for MECP2-e2 were 5'-CTCACCAGTTCCTGCTTTGATGT-3', SEQ ID NO: 7, and 5'-CTTGAGGGGTTTGTCCTTGA-3', SEQ ID NO: 6. The mouse specific primers used for MECP2-e1 were 5'-AGGAGAGACTGGAGGAAAAGTC-3', SEQ ID NO: 8, and 5'-CTTAAACTTCAGTGGCTTGTCTCTG-3', SEQ ID NO: 9. The mouse specific primers used for MECP2-e2 were 5'-CTCACCAGTTCCTGCTTTGATGT-3', SEQ ID NO: 7, and 5'-CTTAAACTTCAGTGGCTTGTCTCTG-3', SEQ ID NO: 9. MECP2 mRNA levels were normalized to Hprt mRNA levels, which were analyzed using primer 5'-CGGGGGACATAAAAGTTATTG-3', SEQ ID NO: 10, and 5'-TGCATTGTTTTACCAGTGTCAA-3', SEQ ID NO: 11. Results are presented in Table 8 below as average normalized MECP2 mRNA levels relative to saline treated wild type (WT) mice. The results show that all of the antisense oligonucleotides tested inhibited MECP2 mRNA and protein levels in the transgenic mice, and human MECP2 mRNA levels were specifically inhibited, whereas mouse MECP2 mRNA levels were not inhibited. Isis Number 628785 was the most potent in the first experiments and was carried forward. Entries listed as "n/a" indicate that the corresponding experiment was not performed.

TABLE 7

Antisense oligonucleotides targeted to human MECP2

| Isis No. | Sequence (5' to 3') | Start site | Stop site | SEQ ID NO. |
|---|---|---|---|---|
| 628724 | $A_{es}$ $A_{eo}$ $^mC_{eo}$ $T_{eo}$ $^mC_{eo}$ $T_{ds}$ $^mC_{ds}$ $T_{ds}$ $^mC_{ds}$ $G_{ds}$ $G_{ds}$ $T_{ds}$ $^mC_{ds}$ $A_{ds}$ $^mC_{ds}$ $G_{eo}$ $G_{eo}$ $G_{es}$ $^mC_{es}$ $G_e$ | 69220 | 69239 | 324 |
| 628749 | $^mC_{es}$ $A_{eo}$ $^mC_{eo}$ $A_{eo}$ $^mC_{eo}$ $T_{ds}$ $G_{ds}$ $A_{ds}$ $^mC_{ds}$ $^mC_{ds}$ $T_{ds}$ $T_{ds}$ $T_{ds}$ $^mC_{ds}$ $A_{ds}$ $G_{eo}$ $G_{eo}$ $G_{es}$ $^mC_{es}$ $T_e$ | 7615 | 7634 | 103 |
| 628772 | $G_{es}$ $A_{eo}$ $T_{eo}$ $^mC_{eo}$ $A_{eo}$ $^mC_{ds}$ $T_{ds}$ $G_{ds}$ $G_{ds}$ $A_{ds}$ $A_{ds}$ $^mC_{ds}$ $A_{ds}$ $^mC_{ds}$ $A_{ds}$ $A_{eo}$ $T_{eo}$ $G_{es}$ $G_{es}$ $T_e$ | 22839 | 22858 | 264 |
| 628775 | $^mC_{es}$ $G_{eo}$ $T_{eo}$ $G_{eo}$ $^mC_{eo}$ $^mC_{ds}$ ikds $T_{ds}$ $G_{ds}$ $G_{ds}$ $A_{ds}$ $A_{ds}$ $G_{ds}$ $T_{ds}$ $^mC_{ds}$ $^mC_{eo}$ $T_{eo}$ $T_{es}$ $^mC_{es}$ $^mC_e$ | 24936 | 24955 | 31 |
| 628785 | $G_{es}$ $G_{eo}$ $T_{eo}$ $T_{eo}$ $T_{eo}$ $T_{ds}$ $T_{ds}$ $^mC_{ds}$ $T_{ds}$ $^mC_{ds}$ $^mC_{ds}$ $T_{ds}$ $T_{ds}$ $T_{ds}$ $A_{ds}$ $T_{eo}$ $T_{eo}$ $A_{es}$ $T_{es}$ $^mC_e$ | 30744 | 30763 | 112 |

Superscript "m" indicates 5-methylcytosine.
Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 8

MECP2 mRNA and protein levels in transgenic mice following ASO administration

| Mouse/Isis No. | MECP2 protein level | Total MECP2 mRNA | Human mRNA MECP2-e1 isoform | Human mRNA MECP2-e2 isoform | Mouse mRNA MECP2-e1 isoform | Mouse mRNA MECP2-e2 isoform | SEQ ID NO. |
|---|---|---|---|---|---|---|---|
| WT/PBS | 1.0 | 1.0 | 0.0 | 0.0 | 1.0 | 1.3 | |
| TG/PBS | 2.0 | 3.3 | 0.9 | 8.3 | 1.2 | 1.4 | |
| TG/628724 | 1.5 | 2.0 | n/a | n/a | n/a | n/a | 324 |
| TG/628749 | 1.6 | 2.5 | n/a | n/a | n/a | n/a | 103 |
| TG/628772 | 1.7 | 2.7 | n/a | n/a | n/a | n/a | 264 |
| TG/628775 | 1.4 | 2.1 | n/a | n/a | n/a | n/a | 31 |
| TG/628785 | 1.3 | 1.6 | 0.3 | 2.3 | 1.0 | 1.3 | 112 |

Example 4: Effect of Gradual Infusion of Antisense Oligonucleotide Targeting MECP2 In Vivo In order to gradually infuse antisense oligonucleotide into the right ventricle of the brain, micro-osmotic pumps (Alzet model 1004, Durect, Cupertino, Calif.) were filled with 500 µg of Isis No. 628785 or a control oligonucleotide that is not targeted to MECP2, dissolved in 1000 saline. The pump was then connected through a plastic catheter to a cannula (Alzet Brain Infusion Kit 3, Durect, Cupertino, Calif.). The pump was designed to deliver the drug at a rate of 0.110 per hour for 28 days. The cannula and pump assembly was primed in sterile saline for two days at 37° C. Mice were anesthetized with isoflurane and placed on a computer-guided stereotaxic instrument (Angle Two Stereotaxic Instrument, Leica Microsystems, Bannockburn, Ill.). Anesthesia (isoflurane 3%) was continuously delivered via a small face mask. Ketoprofen 5 mg/kg was administered subcutaneously at the initiation of the surgery. After sterilizing the surgical site with betadine and 70% alcohol, a midline incision was made over the skull and a subcutaneous pocket was generated on the back of the animal. Next, the pump was inserted into the pocket and the cannula was stereotactically implanted to deliver the drug in the right ventricle using the following coordinates: AP=−0.2 mm, ML=1 mm, DV=−3 mm. The incision was sutured shut. Carprofen-containing food pellets were provided for 5 days after the surgery. 28 days after the initiation of the treatment the pump was disconnected from the cannula and removed. Two additional weeks were given to the animals to recover.

Isis No. 628785 was gradually infused into the right ventricles of the brains of 7-week old WT or TG mice using the micro-osmotic pumps. Each treatment group consisted of 4 or 5 animals. At the end of the four-week treatment period, western blot was performed as described in Example 3 to analyze MECP2 protein levels at 4, 8, and 12 weeks following the initiation of antisense oligonucleotide treatment. The results are shown in Table 9 below.

TABLE 9

MECP2 protein levels following antisense oligonucleotide infusion

| | MECP2 protein level (relative to WT/Control) | | |
|---|---|---|---|
| Mouse/Isis No. | 4 weeks | 8 weeks | 12 weeks |
| WT/Control | 1.0 | 1.0 | 1.0 |
| TG/Control | 2.9 | 2.7 | 2.3 |
| TG/628785 | 1.6 | 1.8 | 2.2 |

Example 5: Behavioral Effects of Antisense Oligonucleotide Targeting Human MECP2 In Vivo Following infusion of antisense oligonucleotide as described in Example 4, a battery of behavioral assays were performed to assess phenotypic effects of oligonucleotide treatment in TG mice treated with Isis No. 628785 or a control oligonucleotide and WT mice treated with a control oligonucleotide. Each treatment group contained at least 15 animals.

An open field test was performed two weeks and six weeks after the completion of the 4 week infusion by placing mice into the center of an open arena after habituation in the test room (40×40×30 cm). Their behavior was tracked by laser photobeam breaks for 30 min. Horizontal locomotor activity, rearing activity, time spent in the center of the arena, and entries to the center were analyzed using AccuScan Fusion software (Omnitech, Columbus, Ohio). The results are reported in table 10 below. The results show that the TG mice displayed hypoactivity in the open field test relative to WT mice at both time points, and treatment of TG mice with Isis No. 628785 restored activity close to WT levels.

TABLE 10

Open field test

| Mouse/Isis No. | Horizontal activity (activity counts) | | Rearing episodes | | Time in center (s) | | Entries to center | |
|---|---|---|---|---|---|---|---|---|
| | 2 weeks | 6 weeks | 2 weeks | 6 weeks | 2 weeks | 6 weeks | 2 weeks | 6 weeks |
| WT/Control | 7134 | 5632 | 277 | 236 | 179 | n/a | 147 | 103 |
| TG/Control | 4116 | 3493 | 156 | 106 | 105 | n/a | 65 | 45 |
| TG/628785 | 5550 | 6114 | 170 | 205 | 93 | n/a | 75 | 99 |

Mice were tested in an elevated plus maze two weeks and six weeks after the completion of the 4 week infusion. After habituation in the test room, mice were placed in the center part of the maze facing one of the two open arms. Mouse behavior was video-tracked for 10 minutes, and the time the mice spent in the open arms and the entries to the open arms were recorded and analyzed using ANY-maze system (Stoelting, Wood Dale, Ill.). The results are shown in Table 11 below. The results show that the TG mice displayed increased anxiety in the elevated plus maze test relative to WT mice at both time points, and treatment of TG mice with Isis No. 628785 restored anxiety levels close to WT levels.

TABLE 11

Elevated plus maze

| Mouse/Isis No. | Time in open arms (s) | | Entries into open arms | |
| --- | --- | --- | --- | --- |
| | 2 weeks | 6 weeks | 2 weeks | 6 weeks |
| WT/Control | 139 | 81 | 21 | 12 |
| TG/Control | 76 | 13 | 12 | 2 |
| TG/628785 | 91 | 55 | 11 | 7 |

Mice were assessed in a three-chamber social interaction test three weeks and seven weeks after the completion of the 4 week infusion. The apparatus comprised a clear Plexiglas box with removable partitions that separated the box into three chambers: left, central, and right. In the left and right chambers a cylindrical wire cup was placed with the open side down. Age and gender-matched mice were used as novel partners. Two days before the test, the novel partner mice were habituated to the wire cups (3 inches diameter by 4 inches in height) for 1 hour per day. After habituation in the test room, each mouse was placed in the central chamber and allowed to explore the three chambers for 10 minutes (habituation phase). The time spent in each chamber during the habituation phase was recorded automatically and analyzed using ANY-maze system (Stoelting, Wood Dale, Ill.). Next, a novel partner mouse was placed under a wire cup in either the left or the right chamber. An inanimate object was placed as a control under the wire cup of the opposite chamber. The location of the novel mouse was randomized between the left and right chambers for each test mouse to control for side preference. The mouse tested was allowed to explore again for an additional 10 minutes. The time spent investigating the novel partner (defined by rearing, sniffing or pawing at the wire cup) and the time spent investigating the inanimate object were measured manually. The results are shown in Table 12 below. The results show that the TG mice displayed hypoactivity and decreased social interaction in the three-chamber social interaction test relative to WT mice at both time points, and treatment of TG mice with Isis No. 628785 restored social interaction with a novel partner to WT levels at the 6 week time point.

TABLE 12

Three-chamber social interaction test

| Mouse/Isis No. | Time spent investigating chambers during habituation phase (s) | | | | Time spent investigating novel partner or inanimate object (s) | | | |
| --- | --- | --- | --- | --- | --- | --- | --- | --- |
| | Left | | Right | | Novel partner | | Inanimate object | |
| | 2 weeks | 6 weeks | 2 weeks | 6 weeks | 2 weeks | 6 weeks | 2 weeks | 6 weeks |
| WT/Control | 52.4 | n/a | 44.1 | n/a | 141 | 107 | 38 | 37 |
| TG/Control | 35.5 | n/a | 29.9 | n/a | 106 | 59 | 33 | 28 |
| TG/628785 | 37.7 | n/a | 23.0 | n/a | 94 | 106 | 27 | 28 |

Mice were assessed in an accelerating rotarod test three weeks after the completion of the 4 week infusion. After habituation in the test room, motor coordination was measured using an accelerating rotarod apparatus (Ugo Basile, Varese, Italy). Mice were tested 2 consecutive days, 4 trials each, with an interval of 60 minutes between trials to rest. Each trial lasted for a maximum of 10 minutes; mice that never fell were given a measurement of 600 seconds. The rod accelerated from 4 to 40 r.p.m. in the first 5 minutes. The time that it took for each mouse to fall from the rod (latency to fall) was recorded. Results are shown in Table 13 below. The results show that the TG mice displayed increased performance in the rotarod test relative to WT mice, and treatment of TG mice with Isis No. 628785 restored performance to WT levels.

TABLE 13

Accelerating rotarod test

| Mouse/Isis No. | Latency to fall (s) | |
| --- | --- | --- |
| | Day 1 | Day 2 |
| WT/Control | 174 | 300 |
| TG/Control | 275 | 400 |
| TG/628785 | 183 | 282 |

The results in tables 10-13 above show that treatment with Isis No. 628785 targeting MECP2 reversed behavioral phenotypes of the TG mice. The TG mice treated with Isis No. 628785 performed similarly to WT mice in the rotarod test 3-4 weeks after completion of the infusion. By 6-7 weeks after completion of the infusion, the hypoactivity, anxiety-like behaviors and social behavior of the TG mice were reversed, as evidenced by the open field, elevated plus maze and three-chamber tests, respectively.

Example 6: Dose Response of Antisense Oligonucleotide Targeting Human MECP2 in Patient Cells In order to test for a dose dependent effect of Isis No. 628785 on human cells, B-lymphoblast cells from two individuals affected with MECP2-duplication syndrome and age-matched control cells were cultured in suspension in RPMI 1640 medium with L-glutamine, penicillin-streptomycin, and 10% (v/v) fetal bovice serum. A day before transfection, cells were seeded in triplicate for each treatment in 6-well plates at $10^6$ cells per well in a total volume of 2 mL medium. Cells were transfected with Isis No. 628785 or control oligonucleotide at a concentration listed in Table 14 below with TurboFect transfection reagent (Thermo Scientific, Carlsbad, Calif.). Cells were harvested and RNA was extracted 48 hours after transfection, and MECP2 mRNA levels were analyzed as described in Example 1. Results are presented in Table 14 below as average normalized MECP2 mRNA levels for both patients' cells relative to untreated control cells. The results show that Isis No. 628785 inhibited MECP2 expression in human MECP2 duplication patient cells.

TABLE 14

Antisense oligonucleotide treatment of patient lymphoblasts

| Cell type/Isis No. | Concentration (nM) | Total relative MECP2 mRNA |
|---|---|---|
| Control/Control | 600 | 1.0 |
| Patient/Control | 600 | 3.1 |
| Patient/628785 | 150 | 2.2 |
| Patient/628785 | 300 | 1.6 |
| Patient/628785 | 600 | 1.3 |

Example 7: Reduction of Seizure Activity with an Antisense Oligonucleotide Targeting Human MECP2 In Vivo Without treatment, seizures and accompanying abnormal electrographic discharges occur in MECP2-TG1 mice as they age. In order to test the effect of antisense oligonucleotide treatment on seizure activity in MECP2-TG1 mice, electrocephalography recordings were performed and behavioral seizure activity was observed.

25-35 week old MECP2-TG1 mice that had been treated as described in Example 4 were anaesthetized with isoflurane and mounted in a stereotaxic frame for the surgical implantation of three recording electrodes (Teflon-coated silver wire, 125 µm in diameter) in the subdural space of the left frontal cortex, the left parietal cortex, and the right parietal cortex, with a reference electrode placed in the occipital region of the skull. After 3-5 days of surgical recovery, cortical EEG activity and behavior were recorded for 2 h per day over 3-5 days. Strong electrographic seizure events were typically accompanied by behavioral seizures. FIG. 1 displays representative EEG traces for WT mice, MECP2-TG1 mice without Isis No. 628785 treatment, and MECP2-TG1 mice that received treatment with Isis No. 628785. Treatment of MECP2-TG1 mice with Isis No. 628785 eliminated both behavioral seizures and abnormal EEG discharges.

What is claimed is:

1. A method of treating MECP2 duplication syndrome comprising administering an antisense compound complementary to a MECP2 nucleic acid to an animal in need thereof.

2. The method of claim 1, wherein the animal is a human.

3. The method of claim 1, wherein the administering is parenteral administration.

4. The method of claim 1, wherein the administering is any of intracerebroventricular administration or intrathecal administration.

5. The method of claim 1, wherein the administering reduces MECP2 mRNA or MECP2 protein levels.

6. The method of claim 1, wherein the administering improves motor function.

7. The method of claim 1, wherein the administering improves anxiety.

8. The method of claim 1, wherein the administering improves social interaction.

9. The method of claim 1, wherein the administering improves activity.

10. The method of claim 1, wherein the administering reduces seizures.

11. The method of claim 1, wherein the administering normalizes EEG discharges.

12. The method of claim 1, wherein at least one symptom of MECP2 duplication syndrome is ameliorated, treated, prevented, or slowed.

13. The method of claim 1, wherein the antisense compound is a modified antisense oligonucleotide.

14. The method of claim 13, wherein the modified antisense oligonucleotide comprises at least one modified nucleoside comprising a modified sugar moiety.

15. The method of claim 14, wherein the modified sugar moiety comprises a 2'-O-methoxyethyl (2'-MOE) group or a 2'-OMe group.

16. The method of claim 13, wherein the modified antisense oligonucleotide comprises at least one modified nucleoside comprising a bicyclic sugar moiety.

17. The method of claim 14, wherein the bicyclic sugar moiety has a 2'-4' bridge, wherein the 2'-4' bridge is selected from —O—CH$_2$—; —O—CH$_2$—CH$_2$—; and O—CH(CH$_3$)—.

18. The method of claim 13, wherein the modified antisense oligonucleotide comprises at least one modified nucleoside comprising a sugar surrogate.

19. The method of claim 13, wherein the modified antisense oligonucleotide has a motif comprising:
 a 5'-region consisting of 5 linked 5'-region nucleosides;
 a central region consisting of 10 linked central region nucleosides; and
 a 3'-region consisting of 5 linked 3'-region nucleosides;
 wherein each of the 5'-region nucleosides and each of the 3'-region nucleosides comprises a modified sugar moiety and each of the central region nucleosides is a β-D-deoxyribonucleoside.

20. The method of claim 13, wherein the modified antisense oligonucleotide comprises at least one modified internucleoside linkage.

21. The method of claim 20, wherein at least one modified internucleoside linkage is a phosphorothioate internucleoside linkage.

22. The method of claim 13, wherein each internucleoside linkage of the modified antisense oligonucleotide is either an unmodified phosphodiester internucleoside linkage or a phosphorothioate internucleoside linkage.

23. The method of claim 13, wherein the modified antisense oligonucleotide comprises at least one 5-methyl cytosine.

24. The method of claim 1, wherein the nucleobase sequence of the antisense compound is at least 90% complementary to a MECP2 nucleic acid having the nucleobase sequence of SEQ ID NO: 1 or SEQ ID NO: 2.

25. The method of claim 13, wherein the nucleobase sequence of the modified antisense oligonucleotide is at least 90% complementary to a MECP2 nucleic acid having the nucleobase sequence of SEQ ID NO: 1 or SEQ ID NO: 2.

26. The method of claim 1, wherein the nucleobase sequence of the antisense compound is at least 95% complementary to a MECP2 nucleic acid having the nucleobase sequence of SEQ ID NO: 1 or SEQ ID NO: 2.

27. The method of claim 13, wherein the nucleobase sequence of the modified antisense oligonucleotide is at least 95% complementary to a MECP2 nucleic acid having the nucleobase sequence of SEQ ID NO: 1 or SEQ ID NO: 2.

28. The method of claim 1, wherein the nucleobase sequence of the antisense compound is 100% complementary to a MECP2 nucleic acid having the nucleobase sequence of SEQ ID NO: 1 or SEQ ID NO: 2.

29. The method of claim 13, wherein the nucleobase sequence of the modified antisense oligonucleotide is 100% complementary to a MECP2 nucleic acid having the nucleobase sequence of SEQ ID NO: 1 or SEQ ID NO: 2.

* * * * *